US012583889B2

(12) United States Patent
Wood et al.

(10) Patent No.: US 12,583,889 B2
(45) Date of Patent: Mar. 24, 2026

(54) CELL PENETRATING PEPTIDES

(71) Applicants: Oxford University Innovation Limited, Botley Oxford (GB); United Kingdom Research and Innovation, Swindon (GB)

(72) Inventors: Matthew Wood, Oxford (GB); Suzan Hammond, Oxford (GB); Melissa Bowerman, Oxford (GB); Michael Gait, Cambridge (GB); Frank Adendroth, Cambridge (GB); Graham McClorey, Oxford (GB)

(73) Assignees: Oxford University Innovation Limited, Oxford (GB); United Kingdom Research and Innovation, Swindon (GB)

( * ) Notice: Subject to any disclaimer, the term of this patent is extended or adjusted under 35 U.S.C. 154(b) by 0 days.

(21) Appl. No.: 17/238,994

(22) Filed: Apr. 23, 2021

(65) Prior Publication Data

US 2022/0041662 A1 Feb. 10, 2022

Related U.S. Application Data

(63) Continuation of application No. 16/486,671, filed as application No. PCT/GB2018/050423 on Feb. 16, 2018, now abandoned.

(30) Foreign Application Priority Data

| | | |
|---|---|---|
| Feb. 17, 2017 | (GB) | 1702631 |
| Mar. 28, 2017 | (GB) | 1704947 |
| Jul. 14, 2017 | (GB) | 1711372 |

(51) Int. Cl.

| | |
|---|---|
| ***C07K 14/16*** | (2006.01) |
| ***A61K 47/64*** | (2017.01) |
| ***C07K 9/00*** | (2006.01) |

(52) U.S. Cl.
CPC .......... *C07K 14/163* (2013.01); *A61K 47/645* (2017.08); *C07K 9/00* (2013.01); *C07K 2319/10* (2013.01); *C07K 2319/91* (2013.01)

(58) Field of Classification Search
None
See application file for complete search history.

(56) References Cited

U.S. PATENT DOCUMENTS

| | | | | |
|---|---|---|---|---|
| 7,838,657 | B2 | 11/2010 | Singh et al. | |
| 8,324,371 | B2 | 12/2012 | Popplewell et al. | |
| 8,361,979 | B2 | 1/2013 | Aartsma-Rus et al. | |
| 8,575,305 | B2 | 11/2013 | Gait et al. | |
| 8,637,483 | B2 | 1/2014 | Wilton et al. | |
| 8,741,863 | B2 | 6/2014 | Moulton et al. | |
| 8,835,402 | B2 | 9/2014 | Kole et al. | |
| 9,018,368 | B2 | 4/2015 | Wilton et al. | |
| 9,079,934 | B2 | 7/2015 | Watanabe et al. | |
| 9,161,948 | B2 | 10/2015 | Hanson | |
| 9,238,052 | B2 | 1/2016 | Kameyama et al. | |
| 9,302,014 | B2 * | 4/2016 | Gait | C12N 15/00 |
| 9,447,417 | B2 | 9/2016 | Sazani et al. | |
| 9,528,109 | B2 | 12/2016 | De Kimpe et al. | |
| 9,582,637 | B1 | 2/2017 | Fernandez et al. | |
| 9,926,557 | B2 | 3/2018 | De Kimpe et al. | |
| 10,160,969 | B2 | 12/2018 | Meena et al. | |
| 10,385,092 | B2 | 8/2019 | Watanabe et al. | |
| 10,781,450 | B2 | 9/2020 | Wilton et al. | |
| 10,876,114 | B2 | 12/2020 | Van Deutekom | |
| 2008/0306001 | A1 | 12/2008 | Liik et al. | |
| 2009/0099066 | A1 | 4/2009 | Moulton et al. | |
| 2010/0016215 | A1 | 1/2010 | Moulton et al. | |
| 2011/0105403 | A1 | 5/2011 | Gait et al. | |
| 2011/0269665 | A1 | 11/2011 | Kole | |
| 2012/0289457 | A1 | 11/2012 | Hanson | |
| 2014/0051646 | A1 | 2/2014 | Gait et al. | |
| 2014/0315977 | A1 | 10/2014 | Bestwick et al. | |
| 2014/0342992 | A1 * | 11/2014 | Gait | C12N 15/00 514/17.7 |
| 2015/0183827 | A1 | 7/2015 | Milletti | |
| 2015/0238627 | A1 | 8/2015 | Leger et al. | |
| 2015/0246958 | A1 | 9/2015 | Han | |
| 2016/0237426 | A1 | 8/2016 | Hanson | |
| 2019/0177723 | A1 | 6/2019 | Dickson | |

(Continued)

FOREIGN PATENT DOCUMENTS

| | | |
|---|---|---|
| CN | 103619356 A | 3/2014 |
| CN | 103998458 A | 8/2014 |

(Continued)

OTHER PUBLICATIONS

Bahal et al., "In vivo correction of anaemia in β-thalassemic mice by γPNA-mediated gene editing with nanoparticle delivery," Nature Communications, 7:13304 (2016).
Betts et al., "Pip6-PMO, A New Generation of Peptide-oligonucleotide Conjugates With Improved Cardiac Exon Skipping Activity for DMD Treatment," Molecular Therapy-Nucleic Acids, 1:e38 (2012).
Dutot et al., "Glycosylated cell penetrating peptides and their conjugates to a proapoptotic peptide. Preparation by click chemistry and cell viability studties," Journal of Chemical Biology, 3(1):51-65 (2010).

(Continued)

*Primary Examiner* — Christina Bradley
(74) *Attorney, Agent, or Firm* — Clark & Elbing LLP

(57) ABSTRACT

The present invention relates to peptides, in particular cell penetrating peptides, of 40 amino acid residues or less comprising at least one directly glycosylated amino residue and one or more arginine rich arm domains, and to conjugates of such cell penetrating peptides with a therapeutic molecule. The present invention further relates to the use of the peptides or conjugates in methods of treatment or as a medicament, especially in the treatment of genetic disorders of the central nervous system.

21 Claims, 7 Drawing Sheets

Specification includes a Sequence Listing.

(56) References Cited

U.S. PATENT DOCUMENTS

| | | | |
|---|---|---|---|
| 2019/0241892 A1 | 8/2019 | Van Deutekom | |
| 2020/0131231 A1 | 4/2020 | Wood et al. | |
| 2021/0024922 A1 | 1/2021 | Zain-Lugman et al. | |
| 2021/0299263 A1 | 9/2021 | Wood et al. | |
| 2021/0299264 A1 | 9/2021 | Wood et al. | |
| 2021/0388353 A1 | 12/2021 | Popplewell et al. | |
| 2022/0090066 A1 | 3/2022 | Wood et al. | |
| 2022/0125934 A1 | 4/2022 | Raz et al. | |
| 2022/0275372 A1 | 9/2022 | Wood et al. | |
| 2022/0288218 A1 | 9/2022 | Yokota et al. | |
| 2024/0189434 A1 | 6/2024 | Godfrey et al. | |
| 2024/0200062 A1 | 6/2024 | Godfrey et al. | |
| 2024/0299563 A1 | 9/2024 | Wood et al. | |

FOREIGN PATENT DOCUMENTS

| | | | | |
|---|---|---|---|---|
| CN | 104837997 A | 8/2015 | | |
| EP | 2394665 A1 | 12/2011 | | |
| EP | 3034074 A1 | 6/2016 | | |
| EP | 2344637 B2 | 2/2018 | | |
| EP | 3443976 A1 | 2/2019 | | |
| EP | 3031920 B1 | 8/2019 | | |
| GB | 2563964 A | 1/2019 | | |
| JP | 2006-514602 A | 5/2006 | | |
| JP | 2007-509978 A | 4/2007 | | |
| JP | 2009-544749 A | 12/2009 | | |
| JP | 2010-532168 A | 10/2010 | | |
| JP | 2011-523557 A | 8/2011 | | |
| JP | 2013-531988 A | 8/2013 | | |
| JP | 2014-515762 A | 7/2014 | | |
| JP | 2014-526238 A | 10/2014 | | |
| JP | 2015-522264 A | 8/2015 | | |
| JP | 2015-532264 A | 11/2015 | | |
| JP | 2018-532695 A | 11/2018 | | |
| KR | 10-2015-0032265 A | 3/2015 | | |
| RU | 2556800 C2 | 7/2015 | | |
| WO | WO-1999/67284 A2 | 12/1999 | | |
| WO | WO-2000/39139 A1 | 7/2000 | | |
| WO | WO-2003/106491 A2 | 12/2003 | | |
| WO | WO-2004/097017 A2 | 11/2004 | | |
| WO | WO-2005/042539 A1 | 5/2005 | | |
| WO | WO-2006/000057 A1 | 1/2006 | | |
| WO | WO-2008/012365 A2 | 1/2008 | | |
| WO | WO-2008/109105 A2 | 9/2008 | | |
| WO | WO-2009/005793 A2 | 1/2009 | | |
| WO | WO-2009/144481 A2 | 12/2009 | | |
| WO | WO-2009/147368 A1 | 12/2009 | | |
| WO | WO-2011/157713 A2 | 12/2011 | | |
| WO | WO-2012012443 A2 | 1/2012 | | |
| WO | WO-2012/072088 A1 | 6/2012 | | |
| WO | WO-2012/090150 A2 | 7/2012 | | |
| WO | WO-2012/150960 A1 | 11/2012 | | |
| WO | WO-2013/040429 A1 | 3/2013 | | |
| WO | WO-2013030569 A2 * | 3/2013 | .............. | A61P 43/00 |
| WO | WO-2014/001229 A2 | 1/2014 | | |
| WO | WO-2014/041505 A1 | 3/2014 | | |
| WO | WO-2014/043544 A1 | 3/2014 | | |
| WO | WO-2014/052276 A1 | 4/2014 | | |
| WO | WO-2015/022504 A2 | 2/2015 | | |
| WO | WO-2015/113922 A1 | 8/2015 | | |
| WO | WO-2015/155753 A2 | 10/2015 | | |
| WO | WO-2015/161255 A1 | 10/2015 | | |
| WO | WO-2016/028187 A1 | 2/2016 | | |
| WO | WO-2016/154328 A2 | 9/2016 | | |
| WO | WO-2017/027848 A1 | 2/2017 | | |
| WO | WO-2018/017190 A2 | 1/2018 | | |
| WO | WO-2018/053316 A1 | 3/2018 | | |
| WO | WO-2019/067975 A1 | 4/2019 | | |
| WO | WO-2019/067979 A1 | 4/2019 | | |
| WO | WO-2019/067981 A1 | 4/2019 | | |
| WO | WO-2020/030927 A1 | 2/2020 | | |
| WO | WO-2020/030928 A1 | 2/2020 | | |
| WO | WO-2020/115494 A1 | 6/2020 | | |
| WO | WO-2020/214763 A1 | 10/2020 | | |
| WO | WO-2020/257489 A1 | 12/2020 | | |
| WO | WO-2021/003573 A1 | 1/2021 | | |
| WO | WO-2021/028666 A1 | 2/2021 | | |
| WO | WO-2022/172019 A1 | 8/2022 | | |
| WO | WO-2022/192749 A2 | 9/2022 | | |
| WO | WO-2022/192754 A2 | 9/2022 | | |

OTHER PUBLICATIONS

Egleton et al., "Improved bioavailability to the brain of glycosylated Met-enkephalin analogs," Brain Research, 881(1):37-46 (2000).

Futaki et al., "Translocation of branched chain arginine peptides through cell membranes: Flexibility in the spatial disposition of positive charges in membrane-permeable peptides," Biochemistry, 41:7926-7930 (2002).

Hammond et al., "Systemic peptide-mediated oligonucleotide therapy improves long-term survival in spinal muscular atrophy," PNAS, 113(39):10962-10967 (2016).

International Preliminary Report on Patentability for International Application No. PCT/GB2018/050423 mailed Aug. 29, 2019.

International Search Report and Written Opinion for International Application No. PCT/GB2018/050423 mailed Jun. 15, 2018.

Lechorche et al., "Cellular uptake and biophysical properties of galactose and/or tryptophan containing cell-penetrating peptides," Biochimica et Biophysica Acta, 1818(3):448-457 (2012).

Osman et al., "Morpholino antisense oligonucleotides targeting intronic repressor Element1 improve phenotype in SMA mouse models," Human Molecular Genetics, 23(18):4832-4845 (2014).

Rothbard et al., "Arginine-rich molecular transporters for drug delivery: Role of backbone spacing in cellular uptake," Journal of Medicinal Chemistry, 45:3612-3618 (2002).

Shabanpoor et al., "Identification of a peptide for systemic brain delivery of a morpholino oligonucleotide in mouse models of spinal muscular atrophy," Nucleic Acid Therapeutics, 27(3):130-144 (2017).

Wermuth et al., "Glossary of Terms used in Medicinal Chemistry," Pure and Applied Chemistry, 70(5): 1129-1143 (1998).

Witt et al., "Peptide drug modifications to enhance bioavailability and blood-brain barrier permeability," Peptides, 22(12):2329-2343 (2001).

Yin et al., "Pip5 Transduction Peptides Direct High Efficiency Oligonucleotide-mediated Dystrophin Exon Skipping in Heart and Phenotypic Correction in mdx Mice," Molecular Therapy, 19(7):1295-1303 (2011).

Zhou et al., "A Novel Morpholino Oligomer Targeting ISS-N1 Improves Rescue of Severe Spinal Muscular Atrophy Transgenic Mice," Human Gene Therapy, 24:331-342 (2013).

"Peptide Design," ThermoFisher Scientific, <https://www.thermofisher.com/us/en/home/life-science/protein-biology/protein-biology-learning-center/protein-biology-resource-library/pierce-protein-methods/peptide-design.html>, retrieved on Oct. 18, 2022 (9 pages).

Ablan et al., "Charge Distribution Fine-Tunes the Translocation of [alpha]-Helical Amphipathic Peptides across Membranes," Biophys J. 111(8):1738-49 (2016).

Alaybeyoglu et al., "Insights into membrane translocation of the cell-penetrating peptide pVEC from molecular dynamics calculations." Journal of Biomolecular Structure and Dynamics. 34(11): 2387-2398 (2016) (14 pages).

Amantana et al., "Pharmacokinetics, biodistribution, stability and toxicity of a cell-penetrating peptide-morpholino oligomer conjugate," Bioconjug Chem. 18(4): 1325-31 (Jun. 2007).

Borrelli et al., "Cell Penetrating Peptides as Molecular Carriers for Anti-Cancer Agents," Molecules. 23(2):295 (Jan. 2018) (28 pages).

Chan et al., "The complexity of antisense transcription revealed by the study of developing male germ cells," Genomics. 87(6):681-92 (2006).

Deuss et al., "Parallel synthesis and splicing redirection activity of cell-penetrating peptide conjugate libraries of a PNA cargo." Organic & Biomolecular Chemistry. 11:7621-7630 (2013) (10 pages).

Dyson et al. "Himia sinteticeskih lekarstvennyh vesestv," Chemistry of Synthetic Drugs. (1964) (9 pages).

Godfrey et al., "How much dystrophin is enough: the physiological consequences of different levels of dystrophin in the mdx mouse." Human Molecular Genetics. 24(15):4225-4237 (May 1, 2015) (13 pages).

(56) References Cited

OTHER PUBLICATIONS

González-Barriga et al., "Design and analysis of effects of triplet repeat oligonucleotides in cell models for myotonic dystrophy," Mol Ther Nucleic Acids. 2(3): 1-12 (Mar. 2013).
Ibraheem et al., "Gene therapy and DNA delivery systems," Int J Pharm. 459(1-2): 70-83 (Jan. 2014).
Jahn et al., "How to systematically evaluate immunogenicity of therapeutic proteins—regulatory considerations," N Biotechnol. 25(5):280-6 (2009).
Kalafatovic et al., "Cell-Penetrating Peptides: Design Strategies beyond Primary Structure and Amphipathicity," Molecules. 22(11):1929 (2017) (38 pages).
Kontermann et al., "Bispecific antibodies," Drug Discov Today. 20(7):838-47 (Jul. 2015) (12 pages).
Kuznetsova, "Brackets in text of a legal document as a linguistic and cognitive phenomenon," Vestnik Mgou. N3:37-43 (2015).
Lapidot et al., "Genome-wide natural antisense transcription: coupling its regulation to its different regulatory mechanisms," EMBO Rep. 7(12):1216-22 (2006).
Lehto et al., "Cellular trafficking determines the exon skipping activity of Pip6a-PMO in mdx skeletal and cardiac muscle cells." Nucleic Acids Res. 42(5):3207-3217 (Dec. 23, 2013) (11 pages).
Lehto et al., "Peptides for nucleic acid delivery," Adv Drug Deliv Rev. 106(Pt A):172-182 (2016).
Marks et al., "Spontaneous Membrane-Translocating Peptides by Orthogonal High-Throughput Screening." Journal of the American Chemical Society. 133: 8995-9004 (May 5, 2011) (10 pages).
Mcclorey et al., "Cell-Penetrating Peptides to Enhance Delivery of Oligonucleotide-Based Therapeutics," Biomedicines. 6(2):51. doi: 10.3390/biomedicines6020051 (May 2018) (15 pages).
Milletti, "Cell-penetrating peptides: classes, origin, and current landscape," Drug Discov Today. 17(15-16):850-860 (2012).
Nan et al., "Antisense Phosphorodiamidate Morpholino Oligomers as Novel Antiviral Compounds," Front Microbiol. 9: 1-15 (Apr. 2018).
Pinto et al., "Impeding Transcription of Expanded Microsatellite Repeats by Deactivated Cas9," Mol Cell. 68(3): 479-490 (Nov. 2017).
Pokrovskij V. I. "Populârnaâ medicinskaâ enciklopedia [Popular Medical Encyclopedia]," Ul'ânovsk "KNIGOCEJ", 4th ed., 1997, p. 317 (drugs) (2 pages).
Rihácek et al. [New Indings in Methotrexate Pharmacology—Diagnostic Possibilities and Impact on Clinical Care] Klin Onkol. 2015;28(3):163-70. doi: 10.14735/amko2015163. (abstract only) (1 page).
Rydberg et al. "Effects of Tryptophan Content and Backbone Spacing on the Uptake Efficiency of Cell-Penetrating Peptides," Biochemistry. 51(27):5531-5539 (Jun. 28, 2021) (9 pages).
Rydberg et al., "Effects of tryptophan content and backbone spacing on the uptake efficiency of cell-penetrating peptides," Biophysical Journal, Board B253. 102(3):487a (2012).
Shabanpoor et al., "Bi-specific splice-switching PMO oligonucleotides conjugated via a single peptide active in a mouse model of Duchenne muscular dystrophy," Nucleic Acids Res. 43(1):29-39 (2015).
Shabanpoor et al., "Development of a general methodology for labelling peptide-morpholino oligonucleotide conjugates using alkyne-azide click chemistry," Chem Commun (Camb). 49(87):10260-2 (2013) (9 pages).
Shen et al., "Single variable domain-IgG fusion. A novel recombinant approach to Fc domain-containing bispecific antibodies," J Biol Chem. 281(16):10706-14 (2006).
Swenson et al., "Chemical modifications of antisense morpholino oligomers enhance their efficacy against Ebola virus infection," Antimicrob Agents Chemother. 53(5):2089-99 (May 2015).
Torres et al., "The immunoglobulin constant region contributes to affinity and specificity," Trends Immunol. 29(2):91-7 (2008).
Wu et al., "Cell-penetrating peptides as transporters for morpholino oligomers: effects of amino acid composition on intracellular delivery and cytotoxicity," Nucleic Acids Res. 35(15):5182-91 (2007).
Wu et al., "Long-term rescue of dystrophin expression and improvement in muscle pathology and function in dystrophic mdx mice by peptide-conjugated morpholino," Am J Pathol. 181(2): 392-400. (Aug. 2012).
Zorko et al., "Cell-penetrating peptides: mechanism and kinetics of cargo delivery," Adv Drug Deliv Rev. 57(4):529-45 (2005).
Haurum et al., "Presentation of Cytosolic Glycosylated Peptides by Human Class I Major Histocompatibility Complex Molecules In Vivo". Journal of Experimental Medicine. 190(1): 145-150 (Jul. 5, 1999) (6 pages).
U.S. Appl. No. 18/913,474, Wood et al.
Berezov T. T. et al., Biologieskaâ himiâ [Biological Chemistry], Moscow, "Medicine", 1998, p. 34 third para., p. 59 last para (3 pages).
Dimachkie et al., "Distal myopathies," available in PMC Aug. 1, 2015, published in final edited form as: Neurol Clin. 32(3):817-42 (Aug. 2014) (Epub May 2014) (32 pages).
Nikolenko et al., "Rehabilitation of children with progressive muscular dystrophy Duchenne," Russian Bulletin of Perinatology and Pediatrics. 4:28-31 (2014).

* cited by examiner

SEQUENCE LISTING

```
<160> NUMBER OF SEQ ID NOS: 191

<210> SEQ ID NO 1
<211> LENGTH: 21
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MISC_FEATURE
<222> LOCATION: (8)..(8)
<223> OTHER INFORMATION: aminohexanoic acid
<220> FEATURE:
<221> NAME/KEY: MISC_FEATURE
<222> LOCATION: (16)..(16)
<223> OTHER INFORMATION: aminohexanoic acid
<220> FEATURE:
<221> NAME/KEY: MOD_RES
<222> LOCATION: (18)..(18)
<223> OTHER INFORMATION: bAla
<220> FEATURE:
<221> NAME/KEY: MISC_FEATURE
<222> LOCATION: (20)..(20)
<223> OTHER INFORMATION: aminohexanoic acid

<400> SEQUENCE: 1

Arg Xaa Arg Arg Xaa Arg Arg Xaa Arg Tyr Gln Phe Leu Ile Arg Xaa
1               5                   10                  15

Arg Xaa Arg Xaa Arg
            20


<210> SEQ ID NO 2
<211> LENGTH: 19
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MISC_FEATURE
<222> LOCATION: (8)..(8)
<223> OTHER INFORMATION: aminohexanoic acid
```

-continued

<220> FEATURE:
<221> NAME/KEY: MISC_FEATURE
<222> LOCATION: (14)..(14)
<223> OTHER INFORMATION: aminohexanoic acid
<220> FEATURE:
<221> NAME/KEY: MOD_RES
<222> LOCATION: (16)..(16)
<223> OTHER INFORMATION: bAla
<220> FEATURE:
<221> NAME/KEY: MISC_FEATURE
<222> LOCATION: (18)..(18)
<223> OTHER INFORMATION: aminohexanoic acid

<400> SEQUENCE: 2

Arg Xaa Arg Arg Xaa Arg Arg Xaa Arg Gln Phe Leu Arg Xaa Arg Xaa
1 5 10 15

Arg Xaa Arg

<210> SEQ ID NO 3
<211> LENGTH: 17
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (14)..(14)
<223> OTHER INFORMATION: bAla
<220> FEATURE:
<221> NAME/KEY: MISC_FEATURE
<222> LOCATION: (16)..(16)
<223> OTHER INFORMATION: aminohexanoic acid

<400> SEQUENCE: 3

Arg Xaa Arg Arg Xaa Arg Arg Phe Gln Ile Leu Tyr Arg Xaa Arg Xaa
1 5 10 15

Arg

<210> SEQ ID NO 4
<211> LENGTH: 17
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (14)..(14)
<223> OTHER INFORMATION: bAla
<220> FEATURE:
<221> NAME/KEY: MISC_FEATURE
<222> LOCATION: (16)..(16)
<223> OTHER INFORMATION: aminohexanoic acid

<400> SEQUENCE: 4

Arg Xaa Arg Arg Xaa Arg Arg Tyr Gln Phe Leu Ile Arg Xaa Arg Xaa
1 5 10 15

-continued

Arg

<210> SEQ ID NO 5
<211> LENGTH: 15
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (12)..(12)
<223> OTHER INFORMATION: bAla
<220> FEATURE:
<221> NAME/KEY: MISC_FEATURE
<222> LOCATION: (14)..(14)
<223> OTHER INFORMATION: aminohexanoic acid

<400> SEQUENCE: 5

Arg Xaa Arg Arg Xaa Arg Arg Gln Phe Leu Arg Xaa Arg Xaa Arg
1               5                   10                  15

<210> SEQ ID NO 6
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (11)..(11)
<223> OTHER INFORMATION: bAla
<220> FEATURE:
<221> NAME/KEY: MISC_FEATURE
<222> LOCATION: (13)..(13)
<223> OTHER INFORMATION: aminohexanoic acid

<400> SEQUENCE: 6

Arg Xaa Arg Arg Xaa Arg Arg Phe Leu Arg Xaa Arg Xaa Arg
1               5                   10

<210> SEQ ID NO 7
<211> LENGTH: 16
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (13)..(13)

<223> OTHER INFORMATION: bAla
<220> FEATURE:
<221> NAME/KEY: MISC_FEATURE
<222> LOCATION: (15)..(15)
<223> OTHER INFORMATION: aminohexanoic acid

<400> SEQUENCE: 7

Arg Xaa Arg Arg Xaa Arg Phe Gln Ile Leu Tyr Arg Xaa Arg Xaa Arg
1               5                   10                  15

<210> SEQ ID NO 8
<211> LENGTH: 20
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MISC_FEATURE
<222> LOCATION: (8)..(8)
<223> OTHER INFORMATION: aminohexanoic acid
<220> FEATURE:
<221> NAME/KEY: MISC_FEATURE
<222> LOCATION: (14)..(14)
<223> OTHER INFORMATION: aminohexanoic acid
<220> FEATURE:
<221> NAME/KEY: MOD_RES
<222> LOCATION: (16)..(16)
<223> OTHER INFORMATION: bAla
<220> FEATURE:
<221> NAME/KEY: MISC_FEATURE
<222> LOCATION: (18)..(18)
<223> OTHER INFORMATION: aminohexanoic acid
<220> FEATURE:
<221> NAME/KEY: CARBOHYD
<222> LOCATION: (20)..(20)
<223> OTHER INFORMATION: L-serine glycosylated with D-Glucose sugar

<400> SEQUENCE: 8

Arg Xaa Arg Arg Xaa Arg Arg Xaa Arg Gln Phe Leu Arg Xaa Arg Xaa
1               5                   10                  15

Arg Xaa Arg Ser
            20

<210> SEQ ID NO 9
<211> LENGTH: 19
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MISC_FEATURE
<222> LOCATION: (8)..(8)
<223> OTHER INFORMATION: aminohexanoic acid
<220> FEATURE:
<221> NAME/KEY: MISC_FEATURE
<222> LOCATION: (14)..(14)
<223> OTHER INFORMATION: aminohexanoic acid
<220> FEATURE:

<221> NAME/KEY: CARBOHYD
<222> LOCATION: (16)..(16)
<223> OTHER INFORMATION: L-serine glycosylated with D-Glucose sugar
<220> FEATURE:
<221> NAME/KEY: MISC_FEATURE
<222> LOCATION: (18)..(18)
<223> OTHER INFORMATION: aminohexanoic acid

<400> SEQUENCE: 9

Arg Xaa Arg Arg Xaa Arg Arg Xaa Arg Gln Phe Leu Arg Xaa Arg Ser
1               5                   10                  15

Arg Xaa Arg

<210> SEQ ID NO 10
<211> LENGTH: 19
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: CARBOHYD
<222> LOCATION: (5)..(5)
<223> OTHER INFORMATION: L-serine glycosylated with D-Glucose sugar
<220> FEATURE:
<221> NAME/KEY: MISC_FEATURE
<222> LOCATION: (8)..(8)
<223> OTHER INFORMATION: aminohexanoic acid
<220> FEATURE:
<221> NAME/KEY: MISC_FEATURE
<222> LOCATION: (14)..(14)
<223> OTHER INFORMATION: aminohexanoic acid
<220> FEATURE:
<221> NAME/KEY: MOD_RES
<222> LOCATION: (16)..(16)
<223> OTHER INFORMATION: bAla
<220> FEATURE:
<221> NAME/KEY: MISC_FEATURE
<222> LOCATION: (18)..(18)
<223> OTHER INFORMATION: aminohexanoic acid

<400> SEQUENCE: 10

Arg Xaa Arg Arg Ser Arg Arg Xaa Arg Gln Phe Leu Arg Xaa Arg Xaa
1               5                   10                  15

Arg Xaa Arg

<210> SEQ ID NO 11
<211> LENGTH: 20
<212> TYPE: PRT
<213> ORGANISM: Artificial Sequence
<220> FEATURE:
<223> OTHER INFORMATION: Carrier peptide
<220> FEATURE:
<221> NAME/KEY: CARBOHYD
<222> LOCATION: (1)..(1)
<223> OTHER INFORMATION: L-serine glycosylated with D-Glucose sugar
<220> FEATURE:
<221> NAME/KEY: MISC_FEATURE
<222> LOCATION: (3)..(3)
<223> OTHER INFORMATION: aminohexanoic acid
<220> FEATURE:
<221> NAME/KEY: MOD_RES
<222> LOCATION: (6)..(6)
<223> OTHER INFORMATION: bAla
<220> FEATURE:
<221> NAME/KEY: MISC_FEATURE
<222> LOCATION: (9)..(9)
<223> OTHER INFORMATION: aminohexanoic acid
<220> FEATURE:
<221> NAME/KEY: MISC_FEATURE
<222> LOCATION: (15)..(15)
<223> OTHER INFORMATION: aminohexanoic acid
<220> FEATURE:
<221> NAME/KEY: MOD_RES
<222> LOCATION: (17)..(17)
<223> OTHER INFORMATION: bAla
<220> FEATURE:
<221> NAME/KEY: MISC_FEATURE
<222> LOCATION: (19)..(19)
<223> OTHER INFORMATION: aminohexanoic acid

<400> SEQUENCE: 11

Ser Arg Xaa Arg Arg Xaa Arg Arg Xaa Arg Gln Phe Leu Arg Xaa Arg
1               5                   10                  15

Xaa Arg Xaa Arg
            20

<210> SEQ ID NO 12
<211> LENGTH: 21
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MISC_FEATURE
<222> LOCATION: (8)..(8)
<223> OTHER INFORMATION: aminohexanoic acid
<220> FEATURE:
<221> NAME/KEY: CARBOHYD
<222> LOCATION: (10)..(10)
<223> OTHER INFORMATION: L-serine glycosylated with D-Glucose sugar
<220> FEATURE:
<221> NAME/KEY: CARBOHYD
<222> LOCATION: (14)..(14)
<223> OTHER INFORMATION: L-serine glycosylated with D-Glucose sugar
<220> FEATURE:
<221> NAME/KEY: MISC_FEATURE
<222> LOCATION: (16)..(16)
<223> OTHER INFORMATION: aminohexanoic acid
<220> FEATURE:
<221> NAME/KEY: MOD_RES
<222> LOCATION: (18)..(18)
<223> OTHER INFORMATION: bAla
<220> FEATURE:
<221> NAME/KEY: MISC_FEATURE
<222> LOCATION: (20)..(20)
<223> OTHER INFORMATION: aminohexanoic acid

<400> SEQUENCE: 12

Arg Xaa Arg Arg Xaa Arg Arg Xaa Arg Ser Gln Phe Leu Ser Arg Xaa
1               5                   10                  15

Arg Xaa Arg Xaa Arg
            20

<210> SEQ ID NO 13
<211> LENGTH: 20
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:

-continued

<221> NAME/KEY: MOD_RES
<222> LOCATION: (5)..(5)
<223> OTHER INFORMATION: bAla
<220> FEATURE:
<221> NAME/KEY: MISC_FEATURE
<222> LOCATION: (8)..(8)
<223> OTHER INFORMATION: aminohexanoic acid
<220> FEATURE:
<221> NAME/KEY: CARBOHYD
<222> LOCATION: (10)..(10)
<223> OTHER INFORMATION: L-serine glycosylated with D-Glucose sugar
<220> FEATURE:
<221> NAME/KEY: MISC_FEATURE
<222> LOCATION: (15)..(15)
<223> OTHER INFORMATION: aminohexanoic acid
<220> FEATURE:
<221> NAME/KEY: MOD_RES
<222> LOCATION: (17)..(17)
<223> OTHER INFORMATION: bAla
<220> FEATURE:
<221> NAME/KEY: MISC_FEATURE
<222> LOCATION: (19)..(19)
<223> OTHER INFORMATION: aminohexanoic acid

<400> SEQUENCE: 13

```
Arg Xaa Arg Arg Xaa Arg Arg Xaa Arg Ser Gln Phe Leu Arg Xaa Arg
1               5                   10                  15

Xaa Arg Xaa Arg
            20
```

<210> SEQ ID NO 14
<211> LENGTH: 19
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MISC_FEATURE
<222> LOCATION: (8)..(8)
<223> OTHER INFORMATION: aminohexanoic acid
<220> FEATURE:
<221> NAME/KEY: CARBOHYD
<222> LOCATION: (10)..(10)
<223> OTHER INFORMATION: L-serine glycosylated with D-Glucose sugar
<220> FEATURE:
<221> NAME/KEY: MISC_FEATURE
<222> LOCATION: (14)..(14)
<223> OTHER INFORMATION: aminohexanoic acid
<220> FEATURE:
<221> NAME/KEY: MOD_RES
<222> LOCATION: (16)..(16)
<223> OTHER INFORMATION: bAla
<220> FEATURE:
<221> NAME/KEY: MISC_FEATURE
<222> LOCATION: (18)..(18)
<223> OTHER INFORMATION: aminohexanoic acid

<400> SEQUENCE: 14

```
Arg Xaa Arg Arg Xaa Arg Arg Xaa Arg Ser Phe Leu Arg Xaa Arg Xaa
1               5                   10                  15

Arg Xaa Arg
```

<210> SEQ ID NO 15
<211> LENGTH: 23
<212> TYPE: PRT

-continued

<213> ORGANISM: Artificial Sequence
<220> FEATURE:
<223> OTHER INFORMATION: Carrier peptide
<220> FEATURE:
<221> NAME/KEY: CARBOHYD
<222> LOCATION: (1)..(1)
<223> OTHER INFORMATION: L-serine glycosylated with D-Glucose sugar
<220> FEATURE:
<221> NAME/KEY: MOD_RES
<222> LOCATION: (2)..(2)
<223> OTHER INFORMATION: bAla
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (9)..(10)
<223> OTHER INFORMATION: bAla
<220> FEATURE:
<221> NAME/KEY: CARBOHYD
<222> LOCATION: (12)..(12)
<223> OTHER INFORMATION: L-serine glycosylated with D-Glucose sugar
<220> FEATURE:
<221> NAME/KEY: MOD_RES
<222> LOCATION: (13)..(13)
<223> OTHER INFORMATION: bAla
<220> FEATURE:
<221> NAME/KEY: MOD_RES
<222> LOCATION: (16)..(16)
<223> OTHER INFORMATION: bAla
<220> FEATURE:
<221> NAME/KEY: MOD_RES
<222> LOCATION: (20)..(21)
<223> OTHER INFORMATION: bAla

<400> SEQUENCE: 15

```
Ser Xaa Arg Lys Xaa Arg Lys Arg Xaa Xaa Arg Ser Xaa Arg Lys Xaa
1               5                   10                  15

Arg Lys Arg Xaa Xaa Arg Lys
            20
```

<210> SEQ ID NO 16
<211> LENGTH: 35
<212> TYPE: PRT
<213> ORGANISM: Artificial Sequence
<220> FEATURE:
<223> OTHER INFORMATION: Carrier peptide
<220> FEATURE:
<221> NAME/KEY: CARBOHYD
<222> LOCATION: (7)..(7)
<223> OTHER INFORMATION: L-serine glycosylated with D-Glucose sugar
<220> FEATURE:
<221> NAME/KEY: MOD_RES
<222> LOCATION: (8)..(8)
<223> OTHER INFORMATION: bAla
<220> FEATURE:
<221> NAME/KEY: MOD_RES
<222> LOCATION: (11)..(11)
<223> OTHER INFORMATION: bAla
<220> FEATURE:
<221> NAME/KEY: MOD_RES
<222> LOCATION: (15)..(16)
<223> OTHER INFORMATION: bAla
<220> FEATURE:
<221> NAME/KEY: CARBOHYD
<222> LOCATION: (24)..(24)
<223> OTHER INFORMATION: L-serine glycosylated with D-Glucose sugar
<220> FEATURE:
<221> NAME/KEY: MOD_RES
<222> LOCATION: (25)..(25)
<223> OTHER INFORMATION: bAla
<220> FEATURE:
<221> NAME/KEY: MOD_RES
<222> LOCATION: (28)..(28)
<223> OTHER INFORMATION: bAla

```
<220> FEATURE:
<221> NAME/KEY: MOD_RES
<222> LOCATION: (32)..(33)
<223> OTHER INFORMATION: bAla

<400> SEQUENCE: 16

Gly Phe Thr Gly Pro Leu Ser Xaa Arg Lys Xaa Arg Lys Arg Xaa Xaa
1               5                   10                  15

Arg Gly Phe Thr Gly Pro Leu Ser Xaa Arg Lys Xaa Arg Lys Arg Xaa
            20                  25                  30

Xaa Arg Lys
        35


<210> SEQ ID NO 17
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (9)..(9)
<223> OTHER INFORMATION: L-serine glycosylated with D-Glucose sugar
<220> FEATURE:
<221> NAME/KEY: MOD_RES
<222> LOCATION: (11)..(11)
<223> OTHER INFORMATION: bAla
<220> FEATURE:
<221> NAME/KEY: MISC_FEATURE
<222> LOCATION: (13)..(13)
<223> OTHER INFORMATION: aminohexanoic acid

<400> SEQUENCE: 17

Arg Xaa Arg Arg Xaa Arg Arg Phe Ser Arg Xaa Arg Xaa Arg
1               5                   10


<210> SEQ ID NO 18
<211> LENGTH: 19
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (2)..(2)
<223> OTHER INFORMATION: bAla
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (8)..(8)
<223> OTHER INFORMATION: bAla
<220> FEATURE:
<221> NAME/KEY: CARBOHYD
<222> LOCATION: (10)..(10)
<223> OTHER INFORMATION: L-serine glycosylated with D-Glucose sugar
<220> FEATURE:
<221> NAME/KEY: MOD_RES
<222> LOCATION: (14)..(14)
<223> OTHER INFORMATION: bAla
<220> FEATURE:
<221> NAME/KEY: MOD_RES
<222> LOCATION: (16)..(16)
```

<223> OTHER INFORMATION: bAla
<220> FEATURE:
<221> NAME/KEY: MOD_RES
<222> LOCATION: (18)..(18)
<223> OTHER INFORMATION: bAla

<400> SEQUENCE: 18

Arg Xaa Arg Arg Xaa Arg Arg Xaa Arg Ser Phe Leu Arg Xaa Arg Xaa
1               5                   10                  15

Arg Xaa Arg

<210> SEQ ID NO 19
<211> LENGTH: 19
<212> TYPE: PRT
<213> ORGANISM: Artificial Sequence
<220> FEATURE:
<223> OTHER INFORMATION: Carrier peptide
<220> FEATURE:
<221> NAME/KEY: CARBOHYD
<222> LOCATION: (10)..(10)
<223> OTHER INFORMATION: L-serine glycosylated with D-Glucose sugar

<400> SEQUENCE: 19

Arg Gly Arg Arg Gly Arg Arg Gly Arg Ser Phe Leu Arg Gly Arg Gly
1               5                   10                  15

Arg Gly Arg

<210> SEQ ID NO 20
<211> LENGTH: 19
<212> TYPE: PRT
<213> ORGANISM: Artificial Sequence
<220> FEATURE:
<223> OTHER INFORMATION: Carrier peptide
<220> FEATURE:
<221> NAME/KEY: CARBOHYD
<222> LOCATION: (10)..(10)
<223> OTHER INFORMATION: L-serine glycosylated with D-Glucose sugar

<400> SEQUENCE: 20

Arg Pro Arg Arg Pro Arg Arg Pro Arg Ser Phe Leu Arg Pro Arg Pro
1               5                   10                  15

Arg Pro Arg

<210> SEQ ID NO 21
<211> LENGTH: 19
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: Hydroxyproline
<220> FEATURE:
<221> NAME/KEY: MISC_FEATURE
<222> LOCATION: (5)..(5)
<223> OTHER INFORMATION: Hydroxyproline
<220> FEATURE:
<221> NAME/KEY: MISC_FEATURE
<222> LOCATION: (8)..(8)
<223> OTHER INFORMATION: Hydroxyproline
<220> FEATURE:
<221> NAME/KEY: CARBOHYD
<222> LOCATION: (10)..(10)
<223> OTHER INFORMATION: L-serine glycosylated with D-Glucose sugar
<220> FEATURE:
<221> NAME/KEY: MISC_FEATURE
<222> LOCATION: (14)..(14)
<223> OTHER INFORMATION: Hydroxyproline
<220> FEATURE:

<221> NAME/KEY: MISC_FEATURE
<222> LOCATION: (16)..(16)
<223> OTHER INFORMATION: Hydroxyproline
<220> FEATURE:
<221> NAME/KEY: MISC_FEATURE
<222> LOCATION: (18)..(18)
<223> OTHER INFORMATION: Hydroxyproline

<400> SEQUENCE: 21

Arg Pro Arg Arg Pro Arg Arg Pro Arg Ser Phe Leu Arg Pro Arg Pro
1 5 10 15

Arg Pro Arg

<210> SEQ ID NO 22
<211> LENGTH: 19
<212> TYPE: PRT
<213> ORGANISM: Artificial Sequence
<220> FEATURE:
<223> OTHER INFORMATION: Carrier peptide
<220> FEATURE:
<221> NAME/KEY: CARBOHYD
<222> LOCATION: (10)..(10)
<223> OTHER INFORMATION: L-serine glycosylated with D-Glucose sugar.

<400> SEQUENCE: 22

Arg Ala Arg Arg Ala Arg Arg Ala Arg Ser Phe Leu Arg Ala Arg Ala
1 5 10 15

Arg Ala Arg

<210> SEQ ID NO 23
<211> LENGTH: 19
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: the non-natural amino acid
1-(amino)cyclohexanecarboxylic acid
<220> FEATURE:
<221> NAME/KEY: MISC_FEATURE
<222> LOCATION: (5)..(5)
<223> OTHER INFORMATION: the non-natural amino acid
1-(amino)cyclohexanecarboxylic acid
<220> FEATURE:
<221> NAME/KEY: MISC_FEATURE
<222> LOCATION: (8)..(8)
<223> OTHER INFORMATION: the non-natural amino acid
1-(amino)cyclohexanecarboxylic acid
<220> FEATURE:
<221> NAME/KEY: CARBOHYD
<222> LOCATION: (10)..(10)
<223> OTHER INFORMATION: L-serine glycosylated with D-Glucose sugar
<220> FEATURE:
<221> NAME/KEY: MISC_FEATURE
<222> LOCATION: (14)..(14)
<223> OTHER INFORMATION: the non-natural amino acid
1-(amino)cyclohexanecarboxylic acid
<220> FEATURE:
<221> NAME/KEY: MISC_FEATURE
<222> LOCATION: (16)..(16)
<223> OTHER INFORMATION: the non-natural amino acid
1-(amino)cyclohexanecarboxylic acid
<220> FEATURE:
<221> NAME/KEY: MISC_FEATURE
<222> LOCATION: (18)..(18)
<223> OTHER INFORMATION: the non-natural amino acid
1-(amino)cyclohexanecarboxylic acid

<400> SEQUENCE: 23

Arg Xaa Arg Arg Xaa Arg Arg Xaa Arg Ser Phe Leu Arg Xaa Arg Xaa

-continued 1 5 10 15

Arg Xaa Arg

<210> SEQ ID NO 24
<211> LENGTH: 17
<212> TYPE: PRT
<213> ORGANISM: Artificial Sequence
<220> FEATURE:
<223> OTHER INFORMATION: Carrier protein
<220> FEATURE:
<221> NAME/KEY: MOD_RES
<222> LOCATION: (3)..(3)
<223> OTHER INFORMATION: bAla
<220> FEATURE:
<221> NAME/KEY: MOD_RES
<222> LOCATION: (6)..(6)
<223> OTHER INFORMATION: bAla
<220> FEATURE:
<221> NAME/KEY: CARBOHYD
<222> LOCATION: (8)..(8)
<223> OTHER INFORMATION: L-serine glycosylated with D-Glucose sugar.
<220> FEATURE:
<221> NAME/KEY: MOD_RES
<222> LOCATION: (12)..(12)
<223> OTHER INFORMATION: bAla
<220> FEATURE:
<221> NAME/KEY: MOD_RES
<222> LOCATION: (14)..(14)
<223> OTHER INFORMATION: bAla
<220> FEATURE:
<221> NAME/KEY: MOD_RES
<222> LOCATION: (16)..(16)
<223> OTHER INFORMATION: bAla

<400> SEQUENCE: 24

Arg Arg Xaa Arg Arg Xaa Arg Ser Phe Leu Arg Xaa Arg Xaa Arg Xaa
1 5 10 15

Arg

<210> SEQ ID NO 25
<211> LENGTH: 16
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (2)..(2)
<223> OTHER INFORMATION: bAla
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (7)..(7)
<223> OTHER INFORMATION: L-serine glycosylated with D-Glucose sugar.
<220> FEATURE:
<221> NAME/KEY: MOD_RES
<222> LOCATION: (11)..(11)
<223> OTHER INFORMATION: bAla
<220> FEATURE:
<221> NAME/KEY: MOD_RES
<222> LOCATION: (13)..(13)
<223> OTHER INFORMATION: bAla
<220> FEATURE:
<221> NAME/KEY: MOD_RES
<222> LOCATION: (15)..(15)
<223> OTHER INFORMATION: bAla

<400> SEQUENCE: 25

Arg Xaa Arg Arg Xaa Arg Ser Phe Leu Arg Xaa Arg Xaa Arg Xaa Arg
1 5 10 15

<210> SEQ ID NO 26
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (3)..(3)
<223> OTHER INFORMATION: bAla
<220> FEATURE:
<221> NAME/KEY: CARBOHYD
<222> LOCATION: (5)..(5)
<223> OTHER INFORMATION: L-serine glycosylated with D-Glucose sugar
<220> FEATURE:
<221> NAME/KEY: MOD_RES
<222> LOCATION: (9)..(9)
<223> OTHER INFORMATION: bAla
<220> FEATURE:
<221> NAME/KEY: MOD_RES
<222> LOCATION: (11)..(11)
<223> OTHER INFORMATION: bAla
<220> FEATURE:
<221> NAME/KEY: MOD_RES
<222> LOCATION: (13)..(13)
<223> OTHER INFORMATION: bAla

<400> SEQUENCE: 26

Arg Arg Xaa Arg Ser Phe Leu Arg Xaa Arg Xaa Arg Xaa Arg
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (2)..(2)
<223> OTHER INFORMATION: bAla
<220> FEATURE:
<221> NAME/KEY: CARBOHYD
<222> LOCATION: (4)..(4)
<223> OTHER INFORMATION: L-serine glycosylated with D-Glucose suga
<220> FEATURE:
<221> NAME/KEY: MOD_RES
<222> LOCATION: (8)..(8)
<223> OTHER INFORMATION: bAla
<220> FEATURE:
<221> NAME/KEY: MOD_RES
<222> LOCATION: (10)..(10)
<223> OTHER INFORMATION: bAla
<220> FEATURE:
<221> NAME/KEY: MOD_RES
<222> LOCATION: (12)..(12)
<223> OTHER INFORMATION: bAla

<400> SEQUENCE: 27

Arg Xaa Arg Ser Phe Leu Arg Xaa Arg Xaa Arg Xaa Arg
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Carrier peptide
<220> FEATURE:
<221> NAME/KEY: CARBOHYD
<222> LOCATION: (2)..(2)
<223> OTHER INFORMATION: L-serine glycosylated with D-Glucose sugar
<220> FEATURE:

-continued

<221> NAME/KEY: MOD_RES
<222> LOCATION: (6)..(6)
<223> OTHER INFORMATION: bAla
<220> FEATURE:
<221> NAME/KEY: MOD_RES
<222> LOCATION: (8)..(8)
<223> OTHER INFORMATION: bAla
<220> FEATURE:
<221> NAME/KEY: MOD_RES
<222> LOCATION: (10)..(10)
<223> OTHER INFORMATION: bAla

<400> SEQUENCE: 28

Arg Ser Phe Leu Arg Xaa Arg Xaa Arg Xaa Arg
1 5 10

<210> SEQ ID NO 29
<211> LENGTH: 17
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (2)..(2)
<223> OTHER INFORMATION: bAla
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (8)..(8)
<223> OTHER INFORMATION: bAla
<220> FEATURE:
<221> NAME/KEY: CARBOHYD
<222> LOCATION: (10)..(10)
<223> OTHER INFORMATION: L-serine glycosylated with D-Glucose sugar
<220> FEATURE:
<221> NAME/KEY: MOD_RES
<222> LOCATION: (14)..(14)
<223> OTHER INFORMATION: bAla
<220> FEATURE:
<221> NAME/KEY: MOD_RES
<222> LOCATION: (16)..(16)
<223> OTHER INFORMATION: bAla

<400> SEQUENCE: 29

Arg Xaa Arg Arg Xaa Arg Arg Xaa Arg Ser Phe Leu Arg Xaa Arg Xaa
1 5 10 15

Arg

<210> SEQ ID NO 30
<211> LENGTH: 15
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (2)..(2)
<223> OTHER INFORMATION: bAla
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (8)..(8)
<223> OTHER INFORMATION: bAla
<220> FEATURE:
<221> NAME/KEY: CARBOHYD
<222> LOCATION: (10)..(10)
<223> OTHER INFORMATION: L-serine glycosylated with D-Glucose sugar
<220> FEATURE:
<221> NAME/KEY: MOD_RES
<222> LOCATION: (14)..(14)
<223> OTHER INFORMATION: bAla

<400> SEQUENCE: 30

Arg Xaa Arg Arg Xaa Arg Arg Xaa Arg Ser Phe Leu Arg Xaa Arg
1 5 10 15

<210> SEQ ID NO 31
<211> LENGTH: 13
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (2)..(2)
<223> OTHER INFORMATION: bAla
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (8)..(8)
<223> OTHER INFORMATION: bAla
<220> FEATURE:
<221> NAME/KEY: CARBOHYD
<222> LOCATION: (10)..(10)
<223> OTHER INFORMATION: L-serine glycosylated with D-Glucose sugar

<400> SEQUENCE: 31

Arg Xaa Arg Arg Xaa Arg Arg Xaa Arg Ser Phe Leu Arg
1 5 10

<210> SEQ ID NO 32
<211> LENGTH: 12
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (2)..(2)
<223> OTHER INFORMATION: bAla
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (8)..(8)
<223> OTHER INFORMATION: bAla
<220> FEATURE:
<221> NAME/KEY: CARBOHYD
<222> LOCATION: (10)..(10)
<223> OTHER INFORMATION: L-serine glycosylated with D-Glucose sugar

<400> SEQUENCE: 32

Arg Xaa Arg Arg Xaa Arg Arg Xaa Arg Ser Phe Leu
1 5 10

<210> SEQ ID NO 33
<211> LENGTH: 18
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (2)..(2)
<223> OTHER INFORMATION: bAla -continued
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (8)..(8)
<223> OTHER INFORMATION: bAla
<220> FEATURE:
<221> NAME/KEY: CARBOHYD
<222> LOCATION: (10)..(10)
<223> OTHER INFORMATION: L-serine glycosylated with D-Glucose sugar
<220> FEATURE:
<221> NAME/KEY: MOD_RES
<222> LOCATION: (14)..(14)
<223> OTHER INFORMATION: bAla
<220> FEATURE:
<221> NAME/KEY: MOD_RES
<222> LOCATION: (16)..(16)
<223> OTHER INFORMATION: bAla

<400> SEQUENCE: 33

Arg Xaa Arg Arg Xaa Arg Arg Xaa Arg Ser Phe Leu Arg Xaa Arg Xaa
1 5 10 15

Arg Arg

<210> SEQ ID NO 34
<211> LENGTH: 17
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (2)..(2)
<223> OTHER INFORMATION: bAla
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (8)..(8)
<223> OTHER INFORMATION: bAla
<220> FEATURE:
<221> NAME/KEY: CARBOHYD
<222> LOCATION: (10)..(10)
<223> OTHER INFORMATION: L-serine glycosylated with D-Glucose sugar
<220> FEATURE:
<221> NAME/KEY: MOD_RES
<222> LOCATION: (14)..(14)
<223> OTHER INFORMATION: bAla

<400> SEQUENCE: 34

Arg Xaa Arg Arg Xaa Arg Arg Xaa Arg Ser Phe Leu Arg Xaa Arg Arg
1 5 10 15

Arg

<210> SEQ ID NO 35
<211> LENGTH: 16
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (2)..(2)
<223> OTHER INFORMATION: bAla
<220> FEATURE:
<221> NAME/KEY: MOD_RES
<222> LOCATION: (5)..(5)
<223> OTHER INFORMATION: bAla
<220> FEATURE:

-continued

<221> NAME/KEY: MOD_RES
<222> LOCATION: (8)..(8)
<223> OTHER INFORMATION: bAla
<220> FEATURE:
<221> NAME/KEY: CARBOHYD
<222> LOCATION: (10)..(10)
<223> OTHER INFORMATION: L-serine glycosylated with D-Glucose sugar

<400> SEQUENCE: 35

Arg Xaa Arg Arg Xaa Arg Arg Xaa Arg Ser Phe Leu Arg Arg Arg Arg
1 5 10 15

<210> SEQ ID NO 36
<211> LENGTH: 18
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (2)..(2)
<223> OTHER INFORMATION: bAla
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (9)..(9)
<223> OTHER INFORMATION: L-serine glycosylated with D-Glucose sugar
<220> FEATURE:
<221> NAME/KEY: MOD_RES
<222> LOCATION: (13)..(13)
<223> OTHER INFORMATION: bAla
<220> FEATURE:
<221> NAME/KEY: MOD_RES
<222> LOCATION: (15)..(15)
<223> OTHER INFORMATION: bAla
<220> FEATURE:
<221> NAME/KEY: MOD_RES
<222> LOCATION: (17)..(17)
<223> OTHER INFORMATION: bAla

<400> SEQUENCE: 36

Arg Xaa Arg Arg Xaa Arg Arg Arg Ser Phe Leu Arg Xaa Arg Xaa Arg
1 5 10 15

Xaa Arg

<210> SEQ ID NO 37
<211> LENGTH: 17
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (2)..(2)
<223> OTHER INFORMATION: bAla
<220> FEATURE:
<221> NAME/KEY: CARBOHYD
<222> LOCATION: (8)..(8)
<223> OTHER INFORMATION: L-serine glycosylated with D-Glucose sugar
<220> FEATURE:
<221> NAME/KEY: MOD_RES
<222> LOCATION: (12)..(12)
<223> OTHER INFORMATION: bAla
<220> FEATURE:
<221> NAME/KEY: MOD_RES
<222> LOCATION: (14)..(14)
<223> OTHER INFORMATION: bAla
<220> FEATURE:
<221> NAME/KEY: MOD_RES
<222> LOCATION: (16)..(16)
<223> OTHER INFORMATION: bAla

<400> SEQUENCE: 37

```
Arg Xaa Arg Arg Arg Arg Arg Ser Phe Leu Arg Xaa Arg Xaa Arg Xaa
1               5                   10                  15

Arg
```

<210> SEQ ID NO 38
<211> LENGTH: 16
<212> TYPE: PRT
<213> ORGANISM: Artificial Sequence
<220> FEATURE:
<223> OTHER INFORMATION: Carrier peptide
<220> FEATURE:
<221> NAME/KEY: CARBOHYD
<222> LOCATION: (7)..(7)
<223> OTHER INFORMATION: L-serine glycosylated with D-Glucose sugar
<220> FEATURE:
<221> NAME/KEY: MOD_RES
<222> LOCATION: (11)..(11)
<223> OTHER INFORMATION: bAla
<220> FEATURE:
<221> NAME/KEY: MOD_RES
<222> LOCATION: (13)..(13)
<223> OTHER INFORMATION: bAla
<220> FEATURE:
<221> NAME/KEY: MOD_RES
<222> LOCATION: (15)..(15)
<223> OTHER INFORMATION: bAla

<400> SEQUENCE: 38

```
Arg Arg Arg Arg Arg Arg Ser Phe Leu Arg Xaa Arg Xaa Arg Xaa Arg
1               5                   10                  15
```

<210> SEQ ID NO 39
<211> LENGTH: 16
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (2)..(2)
<223> OTHER INFORMATION: bAla
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (9)..(9)
<223> OTHER INFORMATION: L-serine glycosylated with D-Glucose sugar
<220> FEATURE:
<221> NAME/KEY: MOD_RES
<222> LOCATION: (14)..(14)
<223> OTHER INFORMATION: bAla

<400> SEQUENCE: 39

```
Arg Xaa Arg Arg Xaa Arg Arg Arg Ser Phe Leu Arg Arg Xaa Arg Arg
1               5                   10                  15
```

<210> SEQ ID NO 40
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (2)..(2)
<223> OTHER INFORMATION: bAla
<220> FEATURE:
<221> NAME/KEY: CARBOHYD -continued
<222> LOCATION: (8)..(8)
<223> OTHER INFORMATION: L-serine glycosylated with D-Glucose sugar

<400> SEQUENCE: 40

Arg Xaa Arg Arg Arg Arg Arg Ser Phe Leu Arg Arg Arg Arg
1 5 10

<210> SEQ ID NO 41
<211> LENGTH: 13
<212> TYPE: PRT
<213> ORGANISM: Artificial Sequence
<220> FEATURE:
<223> OTHER INFORMATION: Carrier peptide
<220> FEATURE:
<221> NAME/KEY: CARBOHYD
<222> LOCATION: (7)..(7)
<223> OTHER INFORMATION: L-serine glycosylated with D-Glucose sugar

<400> SEQUENCE: 41

Arg Arg Arg Arg Arg Arg Ser Phe Leu Arg Arg Arg Arg
1 5 10

<210> SEQ ID NO 42
<211> LENGTH: 22
<212> TYPE: PRT
<213> ORGANISM: Artificial Sequence
<220> FEATURE:
<223> OTHER INFORMATION: Carrier peptide
<220> FEATURE:
<221> NAME/KEY: CARBOHYD
<222> LOCATION: (5)..(5)
<223> OTHER INFORMATION: L-serine glycosylated with D-Glucose sugar
<220> FEATURE:
<221> NAME/KEY: CARBOHYD
<222> LOCATION: (11)..(11)
<223> OTHER INFORMATION: L-serine glycosylated with D-Glucose sugar
<220> FEATURE:
<221> NAME/KEY: MOD_RES
<222> LOCATION: (18)..(18)
<223> OTHER INFORMATION: bAla

<400> SEQUENCE: 42

Arg Gly Arg Arg Ser Gly Arg Arg Gly Arg Ser Phe Leu Arg Gly Gly
1 5 10 15

Arg Xaa Arg Gly Gly Arg
20

<210> SEQ ID NO 43
<211> LENGTH: 18
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MISC_FEATURE
<222> LOCATION: (8)..(8)
<223> OTHER INFORMATION: aminohexanoic acid
<220> FEATURE:
<221> NAME/KEY: CARBOHYD
<222> LOCATION: (10)..(10)
<223> OTHER INFORMATION: L-serine glycosylated with D-Glucose sugar
<220> FEATURE:
<221> NAME/KEY: MISC_FEATURE
<222> LOCATION: (13)..(13)

<223> OTHER INFORMATION: aminohexanoic acid
<220> FEATURE:
<221> NAME/KEY: MOD_RES
<222> LOCATION: (15)..(15)
<223> OTHER INFORMATION: bAla
<220> FEATURE:
<221> NAME/KEY: MISC_FEATURE
<222> LOCATION: (17)..(17)
<223> OTHER INFORMATION: aminohexanoic acid

<400> SEQUENCE: 43

Arg Xaa Arg Arg Xaa Arg Arg Xaa Arg Ser Phe Arg Xaa Arg Xaa Arg
1               5                   10                  15

Xaa Arg

<210> SEQ ID NO 44
<211> LENGTH: 17
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MISC_FEATURE
<222> LOCATION: (8)..(8)
<223> OTHER INFORMATION: aminohexanoic acid
<220> FEATURE:
<221> NAME/KEY: CARBOHYD
<222> LOCATION: (10)..(10)
<223> OTHER INFORMATION: L-serine glycosylated with D-Glucose sugar
<220> FEATURE:
<221> NAME/KEY: MISC_FEATURE
<222> LOCATION: (12)..(12)
<223> OTHER INFORMATION: aminohexanoic acid
<220> FEATURE:
<221> NAME/KEY: MOD_RES
<222> LOCATION: (14)..(14)
<223> OTHER INFORMATION: bAla
<220> FEATURE:
<221> NAME/KEY: MISC_FEATURE
<222> LOCATION: (16)..(16)
<223> OTHER INFORMATION: aminohexanoic acid

<400> SEQUENCE: 44

Arg Xaa Arg Arg Xaa Arg Arg Xaa Arg Ser Arg Xaa Arg Xaa Arg Xaa
1               5                   10                  15

Arg

<210> SEQ ID NO 45
<211> LENGTH: 18
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (8)..(8)
<223> OTHER INFORMATION: L-serine glycosylated with D-Glucose sugar
<220> FEATURE:
<221> NAME/KEY: MOD_RES
<222> LOCATION: (15)..(15)
<223> OTHER INFORMATION: bAla
<220> FEATURE:
<221> NAME/KEY: MISC_FEATURE
<222> LOCATION: (17)..(17)
<223> OTHER INFORMATION: aminohexanoic acid

<400> SEQUENCE: 45

Arg Xaa Arg Arg Xaa Arg Arg Ser Phe Gln Ile Leu Tyr Arg Xaa Arg
1 5 10 15

Xaa Arg

<210> SEQ ID NO 46
<211> LENGTH: 15
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (8)..(8)
<223> OTHER INFORMATION: L-serine glycosylated with D-Glucose sugar
<220> FEATURE:
<221> NAME/KEY: MOD_RES
<222> LOCATION: (12)..(12)
<223> OTHER INFORMATION: bAla
<220> FEATURE:
<221> NAME/KEY: MISC_FEATURE
<222> LOCATION: (14)..(14)
<223> OTHER INFORMATION: aminohexanoic acid

<400> SEQUENCE: 46

Arg Xaa Arg Arg Xaa Arg Arg Ser Phe Leu Arg Xaa Arg Xaa Arg
1 5 10 15

<210> SEQ ID NO 47
<211> LENGTH: 22
<212> TYPE: PRT
<213> ORGANISM: Artificial Sequence
<220> FEATURE:
<223> OTHER INFORMATION: carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MISC_FEATURE
<222> LOCATION: (8)..(8)
<223> OTHER INFORMATION: aminohexanoic acid
<220> FEATURE:
<221> NAME/KEY: CARBOHYD
<222> LOCATION: (10)..(10)
<223> OTHER INFORMATION: L-serine glycosylated with D-Glucose sugar
<220> FEATURE:
<221> NAME/KEY: MISC_FEATURE
<222> LOCATION: (14)..(14)
<223> OTHER INFORMATION: aminohexanoic acid
<220> FEATURE:
<221> NAME/KEY: MOD_RES
<222> LOCATION: (16)..(16)

<223> OTHER INFORMATION: bAla
<220> FEATURE:
<221> NAME/KEY: MISC_FEATURE
<222> LOCATION: (18)..(18)
<223> OTHER INFORMATION: aminohexanoic acid
<220> FEATURE:
<221> NAME/KEY: CARBOHYD
<222> LOCATION: (20)..(20)
<223> OTHER INFORMATION: L-serine glycosylated with D-Glucose sugar

<400> SEQUENCE: 47

```
Arg Xaa Arg Arg Xaa Arg Arg Xaa Arg Ser Phe Leu Arg Xaa Arg Xaa
1               5                   10                  15

Arg Xaa Arg Ser Phe Leu
            20
```

<210> SEQ ID NO 48
<211> LENGTH: 19
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MISC_FEATURE
<222> LOCATION: (8)..(8)
<223> OTHER INFORMATION: aminohexanoic acid
<220> FEATURE:
<221> NAME/KEY: MISC_FEATURE
<222> LOCATION: (11)..(11)
<223> OTHER INFORMATION: aminohexanoic acid
<220> FEATURE:
<221> NAME/KEY: MOD_RES
<222> LOCATION: (13)..(13)
<223> OTHER INFORMATION: bAla
<220> FEATURE:
<221> NAME/KEY: MISC_FEATURE
<222> LOCATION: (15)..(15)
<223> OTHER INFORMATION: aminohexanoic acid
<220> FEATURE:
<221> NAME/KEY: CARBOHYD
<222> LOCATION: (17)..(17)
<223> OTHER INFORMATION: L-serine glycosylated with D-Glucose sugar

<400> SEQUENCE: 48

```
Arg Xaa Arg Arg Xaa Arg Arg Xaa Arg Arg Xaa Arg Xaa Arg Xaa Arg
1               5                   10                  15

Ser Phe Leu
```

<210> SEQ ID NO 49
<211> LENGTH: 19
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: CARBOHYD
<222> LOCATION: (5)..(5)
<223> OTHER INFORMATION: L-serine glycosylated with D-Glucose sugar
<220> FEATURE:
<221> NAME/KEY: MISC_FEATURE
<222> LOCATION: (8)..(8)

<223> OTHER INFORMATION: aminohexanoic acid
<220> FEATURE:
<221> NAME/KEY: CARBOHYD
<222> LOCATION: (10)..(10)
<223> OTHER INFORMATION: L-serine glycosylated with D-Glucose sugar
<220> FEATURE:
<221> NAME/KEY: MISC_FEATURE
<222> LOCATION: (14)..(14)
<223> OTHER INFORMATION: aminohexanoic acid
<220> FEATURE:
<221> NAME/KEY: CARBOHYD
<222> LOCATION: (16)..(16)
<223> OTHER INFORMATION: L-serine glycosylated with D-Glucose sugar
<220> FEATURE:
<221> NAME/KEY: MISC_FEATURE
<222> LOCATION: (18)..(18)
<223> OTHER INFORMATION: aminohexanoic acid

<400> SEQUENCE: 49

Arg Xaa Arg Arg Ser Arg Arg Xaa Arg Ser Phe Leu Arg Xaa Arg Ser
1 5 10 15

Arg Xaa Arg

<210> SEQ ID NO 50
<211> LENGTH: 19
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MISC_FEATURE
<222> LOCATION: (8)..(8)
<223> OTHER INFORMATION: aminohexanoic acid
<220> FEATURE:
<221> NAME/KEY: CARBOHYD
<222> LOCATION: (10)..(10)
<223> OTHER INFORMATION: L-serine glycosylated with D-Glucose sugar
<220> FEATURE:
<221> NAME/KEY: MISC_FEATURE
<222> LOCATION: (14)..(14)
<223> OTHER INFORMATION: aminohexanoic acid
<220> FEATURE:
<221> NAME/KEY: MOD_RES
<222> LOCATION: (16)..(16)
<223> OTHER INFORMATION: bAla
<220> FEATURE:
<221> NAME/KEY: MISC_FEATURE
<222> LOCATION: (18)..(18)
<223> OTHER INFORMATION: aminohexanoic acid

<400> SEQUENCE: 50

Arg Xaa Arg Arg Xaa Arg Arg Xaa Arg Ser Phe Gln Arg Xaa Arg Xaa
1 5 10 15

Arg Xaa Arg

<210> SEQ ID NO 51
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid -continued
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (9)..(9)
<223> OTHER INFORMATION: D-serine glycosylated with D-Glucose sugar
<220> FEATURE:
<221> NAME/KEY: MISC_FEATURE
<222> LOCATION: (11)..(11)
<223> OTHER INFORMATION: aminohexanoic acid
<220> FEATURE:
<221> NAME/KEY: MOD_RES
<222> LOCATION: (13)..(13)
<223> OTHER INFORMATION: bAla

<400> SEQUENCE: 51

```
Arg Xaa Arg Arg Xaa Arg Arg Phe Ser Arg Xaa Arg Xaa Arg
1               5                   10
```

<210> SEQ ID NO 52
<211> LENGTH: 19
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MISC_FEATURE
<222> LOCATION: (8)..(8)
<223> OTHER INFORMATION: aminohexanoic acid
<220> FEATURE:
<221> NAME/KEY: CARBOHYD
<222> LOCATION: (10)..(10)
<223> OTHER INFORMATION: L-serine glycosylated with D-Glucose sugar
<220> FEATURE:
<221> NAME/KEY: MISC_FEATURE
<222> LOCATION: (14)..(14)
<223> OTHER INFORMATION: aminohexanoic acid
<220> FEATURE:
<221> NAME/KEY: MOD_RES
<222> LOCATION: (16)..(16)
<223> OTHER INFORMATION: bAla
<220> FEATURE:
<221> NAME/KEY: MISC_FEATURE
<222> LOCATION: (18)..(18)
<223> OTHER INFORMATION: aminohexanoic acid

<400> SEQUENCE: 52

```
Arg Xaa Arg Arg Xaa Arg Arg Xaa Arg Ser Trp Phe Arg Xaa Arg Xaa
1               5                   10                  15

Arg Xaa Arg
```

<210> SEQ ID NO 53
<211> LENGTH: 19
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)

<223> OTHER INFORMATION: bAla
<220> FEATURE:
<221> NAME/KEY: MISC_FEATURE
<222> LOCATION: (8)..(8)
<223> OTHER INFORMATION: aminohexanoic acid
<220> FEATURE:
<221> NAME/KEY: CARBOHYD
<222> LOCATION: (10)..(10)
<223> OTHER INFORMATION: L-serine glycosylated with D-Glucose sugar
<220> FEATURE:
<221> NAME/KEY: MISC_FEATURE
<222> LOCATION: (14)..(14)
<223> OTHER INFORMATION: aminohexanoic acid
<220> FEATURE:
<221> NAME/KEY: MOD_RES
<222> LOCATION: (16)..(16)
<223> OTHER INFORMATION: bAla
<220> FEATURE:
<221> NAME/KEY: MISC_FEATURE
<222> LOCATION: (18)..(18)
<223> OTHER INFORMATION: aminohexanoic acid

<400> SEQUENCE: 53

```
Arg Xaa Arg Arg Xaa Arg Arg Xaa Arg Ser Gln Phe Arg Xaa Arg Xaa
1               5                   10                  15

Arg Xaa Arg
```

<210> SEQ ID NO 54
<211> LENGTH: 25
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MISC_FEATURE
<222> LOCATION: (8)..(8)
<223> OTHER INFORMATION: aminohexanoic acid
<220> FEATURE:
<221> NAME/KEY: CARBOHYD
<222> LOCATION: (10)..(10)
<223> OTHER INFORMATION: L-serine glycosylated with D-Glucose sugar
<220> FEATURE:
<221> NAME/KEY: MISC_FEATURE
<222> LOCATION: (14)..(14)
<223> OTHER INFORMATION: aminohexanoic acid
<220> FEATURE:
<221> NAME/KEY: MOD_RES
<222> LOCATION: (16)..(16)
<223> OTHER INFORMATION: bAla
<220> FEATURE:
<221> NAME/KEY: CARBOHYD
<222> LOCATION: (17)..(17)
<223> OTHER INFORMATION: L-serine glycosylated with D-Glucose sugar
<220> FEATURE:
<221> NAME/KEY: MISC_FEATURE
<222> LOCATION: (24)..(24)
<223> OTHER INFORMATION: aminohexanoic acid

<400> SEQUENCE: 54

```
Arg Xaa Arg Arg Xaa Arg Arg Xaa Arg Ser Phe Gln Arg Xaa Arg Xaa
1               5                   10                  15

Ser Tyr Gln Phe Leu Ile Arg Xaa Arg
            20                  25
```

<210> SEQ ID NO 55

<211> LENGTH: 13
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (8)..(8)
<223> OTHER INFORMATION: L-serine glycosylated with D-Glucose sugar
<220> FEATURE:
<221> NAME/KEY: MOD_RES
<222> LOCATION: (10)..(10)
<223> OTHER INFORMATION: bAla
<220> FEATURE:
<221> NAME/KEY: MISC_FEATURE
<222> LOCATION: (12)..(12)
<223> OTHER INFORMATION: aminohexanoic acid

<400> SEQUENCE: 55

```
Arg Xaa Arg Arg Xaa Arg Arg Ser Arg Xaa Arg Xaa Arg
1               5                   10
```

<210> SEQ ID NO 56
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: CARBOHYD
<222> LOCATION: (6)..(6)
<223> OTHER INFORMATION: L-serine glycosylated with D-Glucose sugar
<220> FEATURE:
<221> NAME/KEY: MOD_RES
<222> LOCATION: (9)..(9)
<223> OTHER INFORMATION: bAla
<220> FEATURE:
<221> NAME/KEY: MOD_RES
<222> LOCATION: (11)..(11)
<223> OTHER INFORMATION: bAla
<220> FEATURE:
<221> NAME/KEY: MISC_FEATURE
<222> LOCATION: (13)..(13)
<223> OTHER INFORMATION: aminohexanoic acid

<400> SEQUENCE: 56

```
Arg Xaa Arg Arg Phe Ser Arg Arg Xaa Arg Xaa Arg Xaa Arg
1               5                   10
```

<210> SEQ ID NO 57
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: CARBOHYD
<222> LOCATION: (3)..(3)
<223> OTHER INFORMATION: L-serine glycosylated with D-Glucose sugar
<220> FEATURE:
<221> NAME/KEY: MOD_RES
<222> LOCATION: (6)..(6)
<223> OTHER INFORMATION: bAla
<220> FEATURE:
<221> NAME/KEY: MOD_RES
<222> LOCATION: (9)..(9)
<223> OTHER INFORMATION: bAla
<220> FEATURE:
<221> NAME/KEY: MOD_RES
<222> LOCATION: (11)..(11)
<223> OTHER INFORMATION: bAla
<220> FEATURE:
<221> NAME/KEY: MISC_FEATURE
<222> LOCATION: (13)..(13)
<223> OTHER INFORMATION: aminohexanoic acid

<400> SEQUENCE: 57

Arg Phe Ser Arg Arg Xaa Arg Arg Xaa Arg Xaa Arg Xaa Arg
1 5 10

<210> SEQ ID NO 58
<211> LENGTH: 13
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: CARBOHYD
<222> LOCATION: (5)..(5)
<223> OTHER INFORMATION: L-serine glycosylated with D-Glucose sugar
<220> FEATURE:
<221> NAME/KEY: MOD_RES
<222> LOCATION: (8)..(8)
<223> OTHER INFORMATION: bAla
<220> FEATURE:
<221> NAME/KEY: MOD_RES
<222> LOCATION: (10)..(10)
<223> OTHER INFORMATION: bAla
<220> FEATURE:
<221> NAME/KEY: MISC_FEATURE
<222> LOCATION: (12)..(12)
<223> OTHER INFORMATION: aminohexanoic acid

<400> SEQUENCE: 58

Arg Xaa Arg Arg Ser Arg Arg Xaa Arg Xaa Arg Xaa Arg
1 5 10

<210> SEQ ID NO 59
<211> LENGTH: 13
<212> TYPE: PRT
<213> ORGANISM: Artificial Sequence
<220> FEATURE:
<223> OTHER INFORMATION: Carrier peptide
<220> FEATURE:
<221> NAME/KEY: CARBOHYD
<222> LOCATION: (2)..(2)
<223> OTHER INFORMATION: L-serine glycosylated with D-Glucose sugar
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (8)..(8)
<223> OTHER INFORMATION: bAla
<220> FEATURE:
<221> NAME/KEY: MOD_RES
<222> LOCATION: (10)..(10)
<223> OTHER INFORMATION: bAla
<220> FEATURE:
<221> NAME/KEY: MISC_FEATURE
<222> LOCATION: (12)..(12)
<223> OTHER INFORMATION: aminohexanoic acid

<400> SEQUENCE: 59

Arg Ser Arg Arg Xaa Arg Arg Xaa Arg Xaa Arg Xaa Arg
1 5 10

<210> SEQ ID NO 60
<211> LENGTH: 13
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (8)..(8)
<223> OTHER INFORMATION: bAla
<220> FEATURE:
<221> NAME/KEY: CARBOHYD
<222> LOCATION: (10)..(10)
<223> OTHER INFORMATION: L-serine glycosylated with D-Glucose sugar
<220> FEATURE:
<221> NAME/KEY: MISC_FEATURE
<222> LOCATION: (12)..(12)
<223> OTHER INFORMATION: aminohexanoic acid

<400> SEQUENCE: 60

Arg Xaa Arg Arg Xaa Arg Arg Xaa Arg Ser Arg Xaa Arg
1 5 10

<210> SEQ ID NO 61
<211> LENGTH: 13
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (8)..(8)
<223> OTHER INFORMATION: bAla
<220> FEATURE:
<221> NAME/KEY: MOD_RES
<222> LOCATION: (10)..(10)
<223> OTHER INFORMATION: bAla
<220> FEATURE:
<221> NAME/KEY: CARBOHYD
<222> LOCATION: (12)..(12)
<223> OTHER INFORMATION: L-serine glycosylated with D-Glucose sugar

<400> SEQUENCE: 61

Arg Xaa Arg Arg Xaa Arg Arg Xaa Arg Xaa Arg Ser Arg
1 5 10

<210> SEQ ID NO 62
<211> LENGTH: 11
<212> TYPE: PRT
<213> ORGANISM: Artificial Sequence
<220> FEATURE:
<223> OTHER INFORMATION: Carrier peptide
<220> FEATURE:

<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (8)..(8)
<223> OTHER INFORMATION: L-serine glycosylated with D-Glucose sugar
<220> FEATURE:
<221> NAME/KEY: MOD_RES
<222> LOCATION: (10)..(10)
<223> OTHER INFORMATION: bAla

<400> SEQUENCE: 62

Arg Xaa Arg Arg Xaa Arg Phe Ser Arg Xaa Arg
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (7)..(7)
<223> OTHER INFORMATION: L-serine glycosylated with D-Glucose sugar
<220> FEATURE:
<221> NAME/KEY: MOD_RES
<222> LOCATION: (9)..(9)
<223> OTHER INFORMATION: bAla

<400> SEQUENCE: 63

Arg Xaa Arg Arg Xaa Arg Ser Arg Xaa Arg
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (4)..(4)
<223> OTHER INFORMATION: bAla
<220> FEATURE:
<221> NAME/KEY: CARBOHYD
<222> LOCATION: (7)..(7)
<223> OTHER INFORMATION: L-serine glycosylated with D-Glucose sugar
<220> FEATURE:
<221> NAME/KEY: MOD_RES
<222> LOCATION: (9)..(9)
<223> OTHER INFORMATION: bAla

<400> SEQUENCE: 64

Arg Xaa Arg Xaa Arg Arg Ser Arg Xaa Arg
1               5                   10

<210> SEQ ID NO 65
<211> LENGTH: 9
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (3)..(3)
<223> OTHER INFORMATION: bAla
<220> FEATURE:
<221> NAME/KEY: CARBOHYD
<222> LOCATION: (6)..(6)
<223> OTHER INFORMATION: L-serine glycosylated with D-Glucose sugar
<220> FEATURE:
<221> NAME/KEY: MOD_RES
<222> LOCATION: (8)..(8)
<223> OTHER INFORMATION: bAla

<400> SEQUENCE: 65

Arg Arg Xaa Arg Arg Ser Arg Xaa Arg
1               5

<210> SEQ ID NO 66
<211> LENGTH: 17
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MISC_FEATURE
<222> LOCATION: (8)..(8)
<223> OTHER INFORMATION: aminohexanoic acid
<220> FEATURE:
<221> NAME/KEY: CARBOHYD
<222> LOCATION: (10)..(10)
<223> OTHER INFORMATION: L-serine glycosylated with D-Glucose sugar
<220> FEATURE:
<221> NAME/KEY: MISC_FEATURE
<222> LOCATION: (12)..(12)
<223> OTHER INFORMATION: aminohexanoic acid
<220> FEATURE:
<221> NAME/KEY: MOD_RES
<222> LOCATION: (14)..(14)
<223> OTHER INFORMATION: bAla
<220> FEATURE:
<221> NAME/KEY: MISC_FEATURE
<222> LOCATION: (16)..(16)
<223> OTHER INFORMATION: aminohexanoic acid

<400> SEQUENCE: 66

His Xaa His Arg Xaa Arg Arg Xaa Arg Ser Arg Xaa His Xaa His Xaa
1               5                   10                  15

Arg

<210> SEQ ID NO 67
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid -continued
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (8)..(8)
<223> OTHER INFORMATION: L-serine glycosylated with D-Glucose sugar
<220> FEATURE:
<221> NAME/KEY: CARBOHYD
<222> LOCATION: (9)..(9)
<223> OTHER INFORMATION: L-serine glycosylated with D-Glucose sugar
<220> FEATURE:
<221> NAME/KEY: MOD_RES
<222> LOCATION: (11)..(11)
<223> OTHER INFORMATION: bAla
<220> FEATURE:
<221> NAME/KEY: MISC_FEATURE
<222> LOCATION: (13)..(13)
<223> OTHER INFORMATION: aminohexanoic acid

<400> SEQUENCE: 67

```
Arg Xaa Arg Arg Xaa Arg Arg Ser Ser Arg Xaa Arg Xaa Arg
1               5                   10
```

<210> SEQ ID NO 68
<211> LENGTH: 15
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (8)..(8)
<223> OTHER INFORMATION: L-serine glycosylated with D-Glucose sugar
<220> FEATURE:
<221> NAME/KEY: CARBOHYD
<222> LOCATION: (9)..(9)
<223> OTHER INFORMATION: L-serine glycosylated with D-Glucose sugar
<220> FEATURE:
<221> NAME/KEY: CARBOHYD
<222> LOCATION: (10)..(10)
<223> OTHER INFORMATION: L-serine glycosylated with D-Glucose sugar
<220> FEATURE:
<221> NAME/KEY: MOD_RES
<222> LOCATION: (12)..(12)
<223> OTHER INFORMATION: bAla
<220> FEATURE:
<221> NAME/KEY: MISC_FEATURE
<222> LOCATION: (14)..(14)
<223> OTHER INFORMATION: aminohexanoic acid

<400> SEQUENCE: 68

```
Arg Xaa Arg Arg Xaa Arg Arg Ser Ser Ser Arg Xaa Arg Xaa Arg
1               5                   10                  15
```

<210> SEQ ID NO 69
<211> LENGTH: 13
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:

<221> NAME/KEY: CARBOHYD
<222> LOCATION: (5)..(5)
<223> OTHER INFORMATION: L-serine glycosylated with D-Glucose sugar
<220> FEATURE:
<221> NAME/KEY: CARBOHYD
<222> LOCATION: (8)..(8)
<223> OTHER INFORMATION: L-serine glycosylated with D-Glucose sugar
<220> FEATURE:
<221> NAME/KEY: CARBOHYD
<222> LOCATION: (10)..(10)
<223> OTHER INFORMATION: L-serine glycosylated with D-Glucose sugar
<220> FEATURE:
<221> NAME/KEY: MISC_FEATURE
<222> LOCATION: (12)..(12)
<223> OTHER INFORMATION: aminohexanoic acid

<400> SEQUENCE: 69

```
Arg Xaa Arg Arg Ser Arg Arg Ser Arg Ser Arg Xaa Arg
1               5                   10
```

<210> SEQ ID NO 70
<211> LENGTH: 11
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (2)..(2)
<223> OTHER INFORMATION: bAla
<220> FEATURE:
<221> NAME/KEY: MOD_RES
<222> LOCATION: (4)..(4)
<223> OTHER INFORMATION: bAla
<220> FEATURE:
<221> NAME/KEY: CARBOHYD
<222> LOCATION: (6)..(6)
<223> OTHER INFORMATION: L-serine glycosylated with D-Glucose sugar
<220> FEATURE:
<221> NAME/KEY: MOD_RES
<222> LOCATION: (8)..(8)
<223> OTHER INFORMATION: bAla
<220> FEATURE:
<221> NAME/KEY: MOD_RES
<222> LOCATION: (10)..(10)
<223> OTHER INFORMATION: bAla

<400> SEQUENCE: 70

```
Arg Xaa Arg Xaa Arg Ser Arg Xaa Arg Xaa Arg
1               5                   10
```

<210> SEQ ID NO 71
<211> LENGTH: 11
<212> TYPE: PRT
<213> ORGANISM: Artificial Sequence
<220> FEATURE:
<223> OTHER INFORMATION: carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MISC_FEATURE
<222> LOCATION: (4)..(4)
<223> OTHER INFORMATION: aminohexanoic acid
<220> FEATURE:
<221> NAME/KEY: CARBOHYD
<222> LOCATION: (6)..(6)
<223> OTHER INFORMATION: L-serine glycosylated with D-Glucose sugar
<220> FEATURE:
<221> NAME/KEY: MISC_FEATURE
<222> LOCATION: (8)..(8)
<223> OTHER INFORMATION: aminohexanoic acid
<220> FEATURE:
<221> NAME/KEY: MISC_FEATURE
<222> LOCATION: (10)..(10)
<223> OTHER INFORMATION: aminohexanoic acid

<400> SEQUENCE: 71

Arg Xaa Arg Xaa Arg Ser Arg Xaa Arg Xaa Arg
1 5 10

<210> SEQ ID NO 72
<211> LENGTH: 12
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (6)..(6)
<223> OTHER INFORMATION: L-serine glycosylated with D-Glucose sugar
<220> FEATURE:
<221> NAME/KEY: MOD_RES
<222> LOCATION: (7)..(7)
<223> OTHER INFORMATION: bAla
<220> FEATURE:
<221> NAME/KEY: MOD_RES
<222> LOCATION: (9)..(9)
<223> OTHER INFORMATION: bAla
<220> FEATURE:
<221> NAME/KEY: MOD_RES
<222> LOCATION: (11)..(11)
<223> OTHER INFORMATION: bAla

<400> SEQUENCE: 72

Arg Xaa Arg Arg Xaa Ser Xaa Arg Xaa Arg Xaa Arg
1 5 10

<210> SEQ ID NO 73
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MISC_FEATURE
<222> LOCATION: (8)..(8)
<223> OTHER INFORMATION: non-natural amino acid tetrahydroisoquinoline-
3-carboxylic acid (TIC
<220> FEATURE:
<221> NAME/KEY: CARBOHYD
<222> LOCATION: (9)..(9)
<223> OTHER INFORMATION: L-serine glycosylated with D-Glucose sugar
<220> FEATURE:
<221> NAME/KEY: MOD_RES
<222> LOCATION: (11)..(11)
<223> OTHER INFORMATION: bAla
<220> FEATURE:
<221> NAME/KEY: MISC_FEATURE
<222> LOCATION: (13)..(13)
<223> OTHER INFORMATION: aminohexanoic acid

<400> SEQUENCE: 73

-continued

Arg Xaa Arg Arg Xaa Arg Arg Xaa Ser Arg Xaa Arg Xaa Arg
1 5 10

<210> SEQ ID NO 74
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (9)..(9)
<223> OTHER INFORMATION: D-serine glycosylated with D-Glucose sugar
<220> FEATURE:
<221> NAME/KEY: MOD_RES
<222> LOCATION: (11)..(11)
<223> OTHER INFORMATION: bAla
<220> FEATURE:
<221> NAME/KEY: MISC_FEATURE
<222> LOCATION: (13)..(13)
<223> OTHER INFORMATION: aminohexanoic acid

<400> SEQUENCE: 74

Arg Xaa Arg Arg Xaa Arg Arg Phe Ser Arg Xaa Arg Xaa Arg
1 5 10

<210> SEQ ID NO 75
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (9)..(9)
<223> OTHER INFORMATION: L-serine glycosylated with an L-Glucose sugar
<220> FEATURE:
<221> NAME/KEY: MOD_RES
<222> LOCATION: (11)..(11)
<223> OTHER INFORMATION: bAla
<220> FEATURE:
<221> NAME/KEY: MISC_FEATURE
<222> LOCATION: (13)..(13)
<223> OTHER INFORMATION: aminohexanoic acid

<400> SEQUENCE: 75

Arg Xaa Arg Arg Xaa Arg Arg Phe Ser Arg Xaa Arg Xaa Arg
1 5 10

<210> SEQ ID NO 76
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (9)..(9)
<223> OTHER INFORMATION: L-serine glycosylated with a D-Mannose sugar
<220> FEATURE:
<221> NAME/KEY: MOD_RES
<222> LOCATION: (11)..(11)
<223> OTHER INFORMATION: bAla
<220> FEATURE:
<221> NAME/KEY: MISC_FEATURE
<222> LOCATION: (13)..(13)
<223> OTHER INFORMATION: aminohexanoic acid

<400> SEQUENCE: 76

Arg Xaa Arg Arg Xaa Arg Arg Phe Ser Arg Xaa Arg Xaa Arg
1               5                   10

<210> SEQ ID NO 77
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (9)..(9)
<223> OTHER INFORMATION: L-serine glycosylated with a D-Lactose sugar
<220> FEATURE:
<221> NAME/KEY: MOD_RES
<222> LOCATION: (11)..(11)
<223> OTHER INFORMATION: bAla
<220> FEATURE:
<221> NAME/KEY: MISC_FEATURE
<222> LOCATION: (13)..(13)
<223> OTHER INFORMATION: aminohexanoic acid

<400> SEQUENCE: 77

Arg Xaa Arg Arg Xaa Arg Arg Phe Ser Arg Xaa Arg Xaa Arg
1               5                   10

<210> SEQ ID NO 78
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (9)..(9)
<223> OTHER INFORMATION: L-asparagine glycosylated with a
      D-2-Acetylamino Glucose sugar
<220> FEATURE:
<221> NAME/KEY: MOD_RES -continued
<222> LOCATION: (11)..(11)
<223> OTHER INFORMATION: bAla
<220> FEATURE:
<221> NAME/KEY: MISC_FEATURE
<222> LOCATION: (13)..(13)
<223> OTHER INFORMATION: aminohexanoic acid

<400> SEQUENCE: 78

Arg Xaa Arg Arg Xaa Arg Arg Phe Asn Arg Xaa Arg Xaa Arg
1 5 10

<210> SEQ ID NO 79
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (9)..(9)
<223> OTHER INFORMATION: L-serine glycosylated with a Galactose sugar
<220> FEATURE:
<221> NAME/KEY: MOD_RES
<222> LOCATION: (11)..(11)
<223> OTHER INFORMATION: bAla
<220> FEATURE:
<221> NAME/KEY: MISC_FEATURE
<222> LOCATION: (13)..(13)
<223> OTHER INFORMATION: aminohexanoic acid

<400> SEQUENCE: 79

Arg Xaa Arg Arg Xaa Arg Arg Phe Ser Arg Xaa Arg Xaa Arg
1 5 10

<210> SEQ ID NO 80
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: non-natural amino acid 3-azetidine-carboxylic acid
<220> FEATURE:
<221> NAME/KEY: MISC_FEATURE
<222> LOCATION: (5)..(5)
<223> OTHER INFORMATION: non-natural amino acid 3-azetidine-carboxylic acid
<220> FEATURE:
<221> NAME/KEY: MISC_FEATURE
<222> LOCATION: (8)..(8)
<223> OTHER INFORMATION: non-natural amino acid tetrahydroisoquinoline-3-carboxylic acid (TIC)
<220> FEATURE:
<221> NAME/KEY: CARBOHYD
<222> LOCATION: (9)..(9)
<223> OTHER INFORMATION: L-serine glycosylated with D-Glucose sugar
<220> FEATURE:
<221> NAME/KEY: MISC_FEATURE
<222> LOCATION: (11)..(11)
<223> OTHER INFORMATION: non-natural amino acid 3-azetidine-carboxylic acid
<220> FEATURE:
<221> NAME/KEY: MISC_FEATURE
<222> LOCATION: (13)..(13)

<223> OTHER INFORMATION: non-natural amino acid 3-azetidine-carboxylic
      acid

<400> SEQUENCE: 80

Arg Xaa Arg Arg Xaa Arg Arg Xaa Ser Arg Xaa Arg Xaa Arg
1               5                   10

<210> SEQ ID NO 81
<211> LENGTH: 9
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MISC_FEATURE
<222> LOCATION: (8)..(8)
<223> OTHER INFORMATION: aminohexanoic acid

<400> SEQUENCE: 81

Arg Xaa Arg Arg Xaa Arg Arg Xaa Arg
1               5

<210> SEQ ID NO 82
<211> LENGTH: 7
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (4)..(4)
<223> OTHER INFORMATION: bAla
<220> FEATURE:
<221> NAME/KEY: MISC_FEATURE
<222> LOCATION: (6)..(6)
<223> OTHER INFORMATION: aminohexanoic acid

<400> SEQUENCE: 82

Arg Xaa Arg Xaa Arg Xaa Arg
1               5

<210> SEQ ID NO 83
<211> LENGTH: 7
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla

<400> SEQUENCE: 83

Arg Xaa Arg Arg Xaa Arg Arg
1               5

-continued

<210> SEQ ID NO 84
<211> LENGTH: 5
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (2)..(2)
<223> OTHER INFORMATION: bAla
<220> FEATURE:
<221> NAME/KEY: MISC_FEATURE
<222> LOCATION: (4)..(4)
<223> OTHER INFORMATION: aminohexanoic acid

<400> SEQUENCE: 84

Arg Xaa Arg Xaa Arg
1               5

<210> SEQ ID NO 85
<211> LENGTH: 9
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (2)..(2)
<223> OTHER INFORMATION: bAla
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (8)..(8)
<223> OTHER INFORMATION: bAla

<400> SEQUENCE: 85

Arg Xaa Arg Arg Xaa Arg Arg Xaa Arg
1               5

<210> SEQ ID NO 86
<211> LENGTH: 7
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (2)..(2)
<223> OTHER INFORMATION: bAla
<220> FEATURE:
<221> NAME/KEY: MOD_RES
<222> LOCATION: (4)..(4)
<223> OTHER INFORMATION: bAla
<220> FEATURE:
<221> NAME/KEY: MOD_RES
<222> LOCATION: (6)..(6)
<223> OTHER INFORMATION: bAla

<400> SEQUENCE: 86

Arg Xaa Arg Xaa Arg Xaa Arg
1               5

<210> SEQ ID NO 87
<211> LENGTH: 9
<212> TYPE: PRT
<213> ORGANISM: Artificial Sequence
<220> FEATURE:
<223> OTHER INFORMATION: Carrier peptide

<400> SEQUENCE: 87

Arg Gly Arg Arg Gly Arg Arg Gly Arg
1               5

<210> SEQ ID NO 88
<211> LENGTH: 7
<212> TYPE: PRT
<213> ORGANISM: Artificial Sequence
<220> FEATURE:
<223> OTHER INFORMATION: Carrier peptide

<400> SEQUENCE: 88

Arg Gly Arg Gly Arg Gly Arg
1               5

<210> SEQ ID NO 89
<211> LENGTH: 9
<212> TYPE: PRT
<213> ORGANISM: Artificial Sequence
<220> FEATURE:
<223> OTHER INFORMATION: Carrier peptide

<400> SEQUENCE: 89

Arg Pro Arg Arg Pro Arg Arg Pro Arg
1               5

<210> SEQ ID NO 90
<211> LENGTH: 7
<212> TYPE: PRT
<213> ORGANISM: Artificial Sequence
<220> FEATURE:
<223> OTHER INFORMATION: Carrier peptide

<400> SEQUENCE: 90

Arg Pro Arg Pro Arg Pro Arg
1               5

<210> SEQ ID NO 91
<211> LENGTH: 9
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: hydroxyproline
<220> FEATURE:
<221> NAME/KEY: MISC_FEATURE
<222> LOCATION: (5)..(5)
<223> OTHER INFORMATION: hydroxyproline
<220> FEATURE:
<221> NAME/KEY: MISC_FEATURE
<222> LOCATION: (8)..(8)
<223> OTHER INFORMATION: hydroxyproline

<400> SEQUENCE: 91

Arg Pro Arg Arg Pro Arg Arg Pro Arg
1               5

<210> SEQ ID NO 92
<211> LENGTH: 7
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)

<223> OTHER INFORMATION: hydroxyproline
<220> FEATURE:
<221> NAME/KEY: MISC_FEATURE
<222> LOCATION: (4)..(4)
<223> OTHER INFORMATION: hydroxyproline
<220> FEATURE:
<221> NAME/KEY: MISC_FEATURE
<222> LOCATION: (6)..(6)
<223> OTHER INFORMATION: hydroxyproline

<400> SEQUENCE: 92

Arg Pro Arg Pro Arg Pro Arg
1 5

<210> SEQ ID NO 93
<211> LENGTH: 9
<212> TYPE: PRT
<213> ORGANISM: Artificial Sequence
<220> FEATURE:
<223> OTHER INFORMATION: Carrier peptide

<400> SEQUENCE: 93

Arg Ala Arg Arg Ala Arg Arg Ala Arg
1 5

<210> SEQ ID NO 94
<211> LENGTH: 7
<212> TYPE: PRT
<213> ORGANISM: Artificial Sequence
<220> FEATURE:
<223> OTHER INFORMATION: Carrier peptide

<400> SEQUENCE: 94

Arg Ala Arg Ala Arg Ala Arg
1 5

<210> SEQ ID NO 95
<211> LENGTH: 9
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: non-natural amino acid
1-(amino)cyclohexanecarboxylic acid
<220> FEATURE:
<221> NAME/KEY: CARBOHYD
<222> LOCATION: (2)..(2)
<223> OTHER INFORMATION: glycosylation
<220> FEATURE:
<221> NAME/KEY: MISC_FEATURE
<222> LOCATION: (5)..(5)
<223> OTHER INFORMATION: non-natural amino acid
1-(amino)cyclohexanecarboxylic acid
<220> FEATURE:
<221> NAME/KEY: CARBOHYD
<222> LOCATION: (5)..(5)
<223> OTHER INFORMATION: glycosylation
<220> FEATURE:
<221> NAME/KEY: MISC_FEATURE
<222> LOCATION: (8)..(8)
<223> OTHER INFORMATION: non-natural amino acid
1-(amino)cyclohexanecarboxylic acid
<220> FEATURE:
<221> NAME/KEY: CARBOHYD
<222> LOCATION: (8)..(8)
<223> OTHER INFORMATION: glycosylation

<400> SEQUENCE: 95

Arg Xaa Arg Arg Xaa Arg Arg Xaa Arg 1 5

<210> SEQ ID NO 96
<211> LENGTH: 7
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: non-natural amino acid
1-(amino)cyclohexanecarboxylic acid
<220> FEATURE:
<221> NAME/KEY: CARBOHYD
<222> LOCATION: (2)..(2)
<223> OTHER INFORMATION: glycosylation
<220> FEATURE:
<221> NAME/KEY: MISC_FEATURE
<222> LOCATION: (4)..(4)
<223> OTHER INFORMATION: non-natural amino acid
1-(amino)cyclohexanecarboxylic acid
<220> FEATURE:
<221> NAME/KEY: CARBOHYD
<222> LOCATION: (4)..(4)
<223> OTHER INFORMATION: glycosylation
<220> FEATURE:
<221> NAME/KEY: MISC_FEATURE
<222> LOCATION: (6)..(6)
<223> OTHER INFORMATION: non-natural amino acid
1-(amino)cyclohexanecarboxylic acid
<220> FEATURE:
<221> NAME/KEY: CARBOHYD
<222> LOCATION: (6)..(6)
<223> OTHER INFORMATION: glycosylation

<400> SEQUENCE: 96

Arg Xaa Arg Xaa Arg Xaa Arg
1 5

<210> SEQ ID NO 97
<211> LENGTH: 7
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (3)..(3)
<223> OTHER INFORMATION: bAla
<220> FEATURE:
<221> NAME/KEY: MOD_RES
<222> LOCATION: (6)..(6)
<223> OTHER INFORMATION: bAla

<400> SEQUENCE: 97

Arg Arg Xaa Arg Arg Xaa Arg
1 5

<210> SEQ ID NO 98
<211> LENGTH: 6
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (2)..(2)
<223> OTHER INFORMATION: bAla
<220> FEATURE:
<221> NAME/KEY: MOD_RES
<222> LOCATION: (5)..(5)
<223> OTHER INFORMATION: bAla

<400> SEQUENCE: 98

Arg Xaa Arg Arg Xaa Arg
1 5

<210> SEQ ID NO 99
<211> LENGTH: 4
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (3)..(3)
<223> OTHER INFORMATION: bAla

<400> SEQUENCE: 99

Arg Arg Xaa Arg
1

<210> SEQ ID NO 100
<211> LENGTH: 5
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (2)..(2)
<223> OTHER INFORMATION: bAla
<220> FEATURE:
<221> NAME/KEY: MOD_RES
<222> LOCATION: (4)..(4)
<223> OTHER INFORMATION: bAla

<400> SEQUENCE: 100

Arg Xaa Arg Xaa Arg
1 5

<210> SEQ ID NO 101
<211> LENGTH: 6
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (2)..(2)
<223> OTHER INFORMATION: bAla
<220> FEATURE:
<221> NAME/KEY: MOD_RES
<222> LOCATION: (4)..(4)
<223> OTHER INFORMATION: bAla

<400> SEQUENCE: 101

Arg Xaa Arg Xaa Arg Arg
1 5

<210> SEQ ID NO 102
<211> LENGTH: 5
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (2)..(2)
<223> OTHER INFORMATION: bAla

<400> SEQUENCE: 102

Arg Xaa Arg Arg Arg 1 5

<210> SEQ ID NO 103
<211> LENGTH: 4
<212> TYPE: PRT
<213> ORGANISM: Artificial Sequence
<220> FEATURE:
<223> OTHER INFORMATION: Carrier peptide

<400> SEQUENCE: 103

Arg Arg Arg Arg
1

<210> SEQ ID NO 104
<211> LENGTH: 8
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (2)..(2)
<223> OTHER INFORMATION: bAla
<220> FEATURE:
<221> NAME/KEY: MOD_RES
<222> LOCATION: (5)..(5)
<223> OTHER INFORMATION: bAla

<400> SEQUENCE: 104

Arg Xaa Arg Arg Xaa Arg Arg Arg
1 5

<210> SEQ ID NO 105
<211> LENGTH: 7
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (2)..(2)
<223> OTHER INFORMATION: bAla

<400> SEQUENCE: 105

Arg Xaa Arg Arg Arg Arg Arg
1 5

<210> SEQ ID NO 106
<211> LENGTH: 6
<212> TYPE: PRT
<213> ORGANISM: Artificial Sequence
<220> FEATURE:
<223> OTHER INFORMATION: Carrier peptide

<400> SEQUENCE: 106

Arg Arg Arg Arg Arg Arg
1 5

<210> SEQ ID NO 107
<211> LENGTH: 5
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (3)..(3)
<223> OTHER INFORMATION: bAla

<400> SEQUENCE: 107

-continued

Arg Arg Xaa Arg Arg
1 5

<210> SEQ ID NO 108
<211> LENGTH: 4
<212> TYPE: PRT
<213> ORGANISM: Artificial Sequence
<220> FEATURE:
<223> OTHER INFORMATION: Carrier peptide

<400> SEQUENCE: 108

Arg Gly Arg Arg
1

<210> SEQ ID NO 109
<211> LENGTH: 5
<212> TYPE: PRT
<213> ORGANISM: Artificial Sequence
<220> FEATURE:
<223> OTHER INFORMATION: Carrier peptide

<400> SEQUENCE: 109

Gly Arg Arg Gly Arg
1 5

<210> SEQ ID NO 110
<211> LENGTH: 9
<212> TYPE: PRT
<213> ORGANISM: Artificial Sequence
<220> FEATURE:
<223> OTHER INFORMATION: Carrier Peptide
<220> FEATURE:
<221> NAME/KEY: MOD_RES
<222> LOCATION: (5)..(5)
<223> OTHER INFORMATION: bAla

<400> SEQUENCE: 110

Arg Gly Gly Arg Xaa Arg Gly Gly Arg
1 5

<210> SEQ ID NO 111
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (9)..(9)
<223> OTHER INFORMATION: L-serine glycosylated with an L-Glucose sugar
<220> FEATURE:
<221> NAME/KEY: MISC_FEATURE
<222> LOCATION: (11)..(11)
<223> OTHER INFORMATION: aminohexanoic acid
<220> FEATURE:
<221> NAME/KEY: MOD_RES
<222> LOCATION: (13)..(13)
<223> OTHER INFORMATION: bAla

<400> SEQUENCE: 111

Arg Xaa Arg Arg Xaa Arg Arg Phe Ser Arg Xaa Arg Xaa Arg
1 5 10

<210> SEQ ID NO 112
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (9)..(9)
<223> OTHER INFORMATION: L-serine glycosylated with a D-Mannose sugar
<220> FEATURE:
<221> NAME/KEY: MISC_FEATURE
<222> LOCATION: (11)..(11)
<223> OTHER INFORMATION: aminohexanoic acid
<220> FEATURE:
<221> NAME/KEY: MOD_RES
<222> LOCATION: (13)..(13)
<223> OTHER INFORMATION: bAla

<400> SEQUENCE: 112

```
Arg Xaa Arg Arg Xaa Arg Arg Phe Ser Arg Xaa Arg Xaa Arg
1               5                   10
```

<210> SEQ ID NO 113
<211> LENGTH: 16
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MISC_FEATURE
<222> LOCATION: (8)..(8)
<223> OTHER INFORMATION: aminohexanoic acid
<220> FEATURE:
<221> NAME/KEY: MISC_FEATURE
<222> LOCATION: (11)..(11)
<223> OTHER INFORMATION: aminohexanoic acid
<220> FEATURE:
<221> NAME/KEY: MOD_RES
<222> LOCATION: (13)..(13)
<223> OTHER INFORMATION: bAla
<220> FEATURE:
<221> NAME/KEY: MISC_FEATURE
<222> LOCATION: (15)..(15)
<223> OTHER INFORMATION: aminohexanoic acid

<400> SEQUENCE: 113

```
Arg Xaa Arg Arg Xaa Arg Arg Xaa Arg Arg Xaa Arg Xaa Arg Xaa Arg
1               5                   10                  15
```

<210> SEQ ID NO 114
<211> LENGTH: 4
<212> TYPE: PRT
<213> ORGANISM: Artificial Sequence
<220> FEATURE:
<223> OTHER INFORMATION: Carrier peptide
<220> FEATURE:

<221> NAME/KEY: MISC_FEATURE
<222> LOCATION: (2)..(2)
<223> OTHER INFORMATION: aminohexanoic acid

<400> SEQUENCE: 114

Arg Xaa Arg Arg
1

<210> SEQ ID NO 115
<211> LENGTH: 4
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (3)..(3)
<223> OTHER INFORMATION: aminohexanoic acid

<400> SEQUENCE: 115

Arg Arg Xaa Arg
1

<210> SEQ ID NO 116
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MISC_FEATURE
<222> LOCATION: (8)..(8)
<223> OTHER INFORMATION: non-natural amino acid tetrahydroisoquinoline-
3-carboxylic acid (TIC)
<220> FEATURE:
<221> NAME/KEY: CARBOHYD
<222> LOCATION: (9)..(9)
<223> OTHER INFORMATION: L-serine glycosylated with D-Glucose sugar
<220> FEATURE:
<221> NAME/KEY: MISC_FEATURE
<222> LOCATION: (11)..(11)
<223> OTHER INFORMATION: aminohexanoic acid
<220> FEATURE:
<221> NAME/KEY: MOD_RES
<222> LOCATION: (13)..(13)
<223> OTHER INFORMATION: bAla

<400> SEQUENCE: 116

Arg Xaa Arg Arg Xaa Arg Arg Xaa Ser Arg Xaa Arg Xaa Arg
1 5 10

<210> SEQ ID NO 117
<211> LENGTH: 8
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (3)..(3)
<223> OTHER INFORMATION: bAla
<220> FEATURE:
<221> NAME/KEY: MOD_RES
<222> LOCATION: (5)..(5)
<223> OTHER INFORMATION: bAla
<220> FEATURE:
<221> NAME/KEY: MISC_FEATURE
<222> LOCATION: (7)..(7)
<223> OTHER INFORMATION: aminohexanoic acid

<400> SEQUENCE: 117

Arg Arg Xaa Arg Xaa Arg Xaa Arg
1 5

<210> SEQ ID NO 118
<211> LENGTH: 11
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (3)..(3)
<223> OTHER INFORMATION: bAla
<220> FEATURE:
<221> NAME/KEY: MOD_RES
<222> LOCATION: (6)..(6)
<223> OTHER INFORMATION: bAla
<220> FEATURE:
<221> NAME/KEY: MOD_RES
<222> LOCATION: (8)..(8)
<223> OTHER INFORMATION: bAla
<220> FEATURE:
<221> NAME/KEY: MISC_FEATURE
<222> LOCATION: (10)..(10)
<223> OTHER INFORMATION: aminohexanoic acid

<400> SEQUENCE: 118

Arg Arg Xaa Arg Arg Xaa Arg Xaa Arg Xaa Arg
1 5 10

<210> SEQ ID NO 119
<211> LENGTH: 9
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (8)..(8)
<223> OTHER INFORMATION: bAla

<400> SEQUENCE: 119

Arg Xaa Arg Arg Asx Arg Arg Asx Arg
1 5

<210> SEQ ID NO 120
<211> LENGTH: 11
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MOD_RES
<222> LOCATION: (8)..(8)
<223> OTHER INFORMATION: bAla
<220> FEATURE:
<221> NAME/KEY: MOD_RES
<222> LOCATION: (10)..(10)
<223> OTHER INFORMATION: bAla

<400> SEQUENCE: 120

Arg Xaa Arg Arg Xaa Arg Arg Xaa Arg Xaa Arg
1 5 10

<210> SEQ ID NO 121
<211> LENGTH: 6
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla

<400> SEQUENCE: 121

Arg Xaa Arg Arg Xaa Arg
1 5

<210> SEQ ID NO 122
<211> LENGTH: 6
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (4)..(4)
<223> OTHER INFORMATION: bAla

<400> SEQUENCE: 122

Arg Xaa Arg Xaa Arg Arg
1 5

<210> SEQ ID NO 123
<211> LENGTH: 9
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MISC_FEATURE
<222> LOCATION: (8)..(8)
<223> OTHER INFORMATION: aminohexanoic acid

<400> SEQUENCE: 123

His Xaa His Arg Xaa Arg Arg Xaa Arg

-continued 1 5

<210> SEQ ID NO 124
<211> LENGTH: 7
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (4)..(4)
<223> OTHER INFORMATION: bAla
<220> FEATURE:
<221> NAME/KEY: MISC_FEATURE
<222> LOCATION: (6)..(6)
<223> OTHER INFORMATION: aminohexanoic acid

<400> SEQUENCE: 124

Arg Xaa His Xaa His Xaa Arg
1 5

<210> SEQ ID NO 125
<211> LENGTH: 5
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MISC_FEATURE
<222> LOCATION: (4)..(4)
<223> OTHER INFORMATION: aminohexanoic acid

<400> SEQUENCE: 125

Arg Xaa Arg Xaa Arg
1 5

<210> SEQ ID NO 126
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: MISC_FEATURE
<222> LOCATION: (9)..(9)
<223> OTHER INFORMATION: L-asparagine glycosylated with a
D-2-Acetylamino Glucose sugar
<220> FEATURE:
<221> NAME/KEY: MISC_FEATURE
<222> LOCATION: (11)..(11)
<223> OTHER INFORMATION: aminohexanoic acid
<220> FEATURE:
<221> NAME/KEY: MOD_RES
<222> LOCATION: (13)..(13)
<223> OTHER INFORMATION: bAla

<400> SEQUENCE: 126

Arg Xaa Arg Arg Xaa Arg Arg Phe Asn Arg Xaa Arg Xaa Arg
1 5 10

<210> SEQ ID NO 127
<211> LENGTH: 6
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (1)..(1)
<223> OTHER INFORMATION: bAla
<220> FEATURE:
<221> NAME/KEY: MOD_RES
<222> LOCATION: (3)..(3)
<223> OTHER INFORMATION: bAla
<220> FEATURE:
<221> NAME/KEY: MOD_RES
<222> LOCATION: (5)..(5)
<223> OTHER INFORMATION: bAla

<400> SEQUENCE: 127

Xaa Arg Xaa Arg Xaa Arg
1 5

<210> SEQ ID NO 128
<211> LENGTH: 10
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (1)..(1)
<223> OTHER INFORMATION: bAla
<220> FEATURE:
<221> NAME/KEY: MOD_RES
<222> LOCATION: (4)..(4)
<223> OTHER INFORMATION: bAla
<220> FEATURE:
<221> NAME/KEY: MOD_RES
<222> LOCATION: (8)..(9)
<223> OTHER INFORMATION: bAla

<400> SEQUENCE: 128

Xaa Arg Lys Xaa Arg Lys Arg Xaa Xaa Arg
1 5 10

<210> SEQ ID NO 129
<211> LENGTH: 11
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (1)..(1)
<223> OTHER INFORMATION: bAla
<220> FEATURE:
<221> NAME/KEY: MOD_RES
<222> LOCATION: (4)..(4)
<223> OTHER INFORMATION: bAla
<220> FEATURE:
<221> NAME/KEY: MOD_RES
<222> LOCATION: (8)..(9)
<223> OTHER INFORMATION: bAla

<400> SEQUENCE: 129

Xaa Arg Lys Xaa Arg Lys Arg Xaa Xaa Arg Lys
1 5 10

-continued

<210> SEQ ID NO 130
<211> LENGTH: 7
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: non-natural amino acid 3-azetidine-carboxylic
acid
<220> FEATURE:
<221> NAME/KEY: MISC_FEATURE
<222> LOCATION: (5)..(5)
<223> OTHER INFORMATION: non-natural amino acid 3-azetidine-carboxylic
acid

<400> SEQUENCE: 130

Arg Xaa Arg Arg Xaa Arg Arg
1               5

<210> SEQ ID NO 131
<211> LENGTH: 5
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: non-natural amino acid 3-azetidine-carboxylic
acid
<220> FEATURE:
<221> NAME/KEY: MISC_FEATURE
<222> LOCATION: (4)..(4)
<223> OTHER INFORMATION: non-natural amino acid 3-azetidine-carboxylic
acid

<400> SEQUENCE: 131

Arg Xaa Arg Xaa Arg
1               5

<210> SEQ ID NO 132
<211> LENGTH: 5
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (4)..(4)
<223> OTHER INFORMATION: bAla

<400> SEQUENCE: 132

Arg Xaa Arg Xaa Arg
1               5

<210> SEQ ID NO 133
<211> LENGTH: 6
<212> TYPE: PRT
<213> ORGANISM: Artificial Sequence
<220> FEATURE:
<223> OTHER INFORMATION: Carrier peptide

<400> SEQUENCE: 133

Gly Phe Thr Gly Pro Leu
1               5

-continued

<210> SEQ ID NO 134
<211> LENGTH: 5
<212> TYPE: PRT
<213> ORGANISM: Artificial Sequence
<220> FEATURE:
<223> OTHER INFORMATION: Carrier peptide

<400> SEQUENCE: 134

Phe Gln Ile Leu Tyr
1               5

<210> SEQ ID NO 135
<211> LENGTH: 5
<212> TYPE: PRT
<213> ORGANISM: Artificial Sequence
<220> FEATURE:
<223> OTHER INFORMATION: Carrier peptide

<400> SEQUENCE: 135

Tyr Gln Phe Leu Ile
1               5

<210> SEQ ID NO 136
<211> LENGTH: 7
<212> TYPE: PRT
<213> ORGANISM: Artificial Sequence
<220> FEATURE:
<223> OTHER INFORMATION: Carrier peptide

<400> SEQUENCE: 136

Arg Arg Arg Arg Arg Arg Arg
1               5

<210> SEQ ID NO 137
<211> LENGTH: 7
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: any non-natural amino acid

<400> SEQUENCE: 137

Arg Xaa Arg Arg Arg Arg Arg
1               5

<210> SEQ ID NO 138
<211> LENGTH: 7
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (3)..(3)
<223> OTHER INFORMATION: any non-natural amino acid

<400> SEQUENCE: 138

Arg Arg Xaa Arg Arg Arg Arg
1               5

<210> SEQ ID NO 139
<211> LENGTH: 7
<212> TYPE: PRT
<213> ORGANISM: Artificial Sequence
<220> FEATURE:

-continued

<223> OTHER INFORMATION: Carrier peptide
<220> FEATURE:
<221> NAME/KEY: MISC_FEATURE
<222> LOCATION: (4)..(4)
<223> OTHER INFORMATION: any non-natural amino acid

<400> SEQUENCE: 139

Arg Arg Arg Xaa Arg Arg Arg
1 5

<210> SEQ ID NO 140
<211> LENGTH: 7
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (5)..(5)
<223> OTHER INFORMATION: any non-natural amino acid

<400> SEQUENCE: 140

Arg Arg Arg Arg Xaa Arg Arg
1 5

<210> SEQ ID NO 141
<211> LENGTH: 7
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (6)..(6)
<223> OTHER INFORMATION: any non-natural amino acid

<400> SEQUENCE: 141

Arg Arg Arg Arg Arg Xaa Arg
1 5

<210> SEQ ID NO 142
<211> LENGTH: 8
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: any non-natural amino acid
<220> FEATURE:
<221> NAME/KEY: MISC_FEATURE
<222> LOCATION: (5)..(5)
<223> OTHER INFORMATION: any non-natural amino acid

<400> SEQUENCE: 142

Arg Xaa Arg Arg Xaa Arg Arg Arg
1 5

<210> SEQ ID NO 143
<211> LENGTH: 8
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (3)..(3)
<223> OTHER INFORMATION: any non-natural amino acid
<220> FEATURE:
<221> NAME/KEY: MISC_FEATURE -continued
<222> LOCATION: (6)..(6)
<223> OTHER INFORMATION: any non-natural amino acid

<400> SEQUENCE: 143

Arg Arg Xaa Arg Arg Xaa Arg Arg
1               5

<210> SEQ ID NO 144
<211> LENGTH: 8
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (4)..(4)
<223> OTHER INFORMATION: any non-natural amino acid
<220> FEATURE:
<221> NAME/KEY: MISC_FEATURE
<222> LOCATION: (7)..(7)
<223> OTHER INFORMATION: any non-natural amino acid

<400> SEQUENCE: 144

Arg Arg Arg Xaa Arg Arg Xaa Arg
1               5

<210> SEQ ID NO 145
<211> LENGTH: 8
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: any non-natural amino acid
<220> FEATURE:
<221> NAME/KEY: MISC_FEATURE
<222> LOCATION: (6)..(6)
<223> OTHER INFORMATION: any non-natural amino acid

<400> SEQUENCE: 145

Arg Xaa Arg Arg Arg Xaa Arg Arg
1               5

<210> SEQ ID NO 146
<211> LENGTH: 8
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: non-natural amino acid
<220> FEATURE:
<221> NAME/KEY: MISC_FEATURE
<222> LOCATION: (7)..(7)
<223> OTHER INFORMATION: non-natural amino acid

<400> SEQUENCE: 146

Arg Xaa Arg Arg Arg Arg Xaa Arg
1               5

<210> SEQ ID NO 147
<211> LENGTH: 20
<212> TYPE: DNA
<213> ORGANISM: Artificial Sequence
<220> FEATURE:
<223> OTHER INFORMATION: PMO antisense sequences targeting the human
SMN2-gene

<400> SEQUENCE: 147
attcactttc ataatgctgg 20

<210> SEQ ID NO 148
<211> LENGTH: 25
<212> TYPE: DNA
<213> ORGANISM: Artificial Sequence
<220> FEATURE:
<223> OTHER INFORMATION: PMO antisense sequences targeting the human SMN2-gene

<400> SEQUENCE: 148
gtaagattca ctttcataat gctgg 25

<210> SEQ ID NO 149
<211> LENGTH: 23
<212> TYPE: DNA
<213> ORGANISM: Artificial Sequence
<220> FEATURE:
<223> OTHER INFORMATION: Forward primer

<400> SEQUENCE: 149
ctcccatatg tccagattct ctt 23

<210> SEQ ID NO 150
<211> LENGTH: 20
<212> TYPE: DNA
<213> ORGANISM: Artificial Sequence
<220> FEATURE:
<223> OTHER INFORMATION: Reverse primer

<400> SEQUENCE: 150
ctacaacacc cttctcacag 20

<210> SEQ ID NO 151
<211> LENGTH: 24
<212> TYPE: DNA
<213> ORGANISM: Artificial Sequence
<220> FEATURE:
<223> OTHER INFORMATION: Primer Exon 6 Fwd:

<400> SEQUENCE: 151
gctttgggaa gtatgttaat ttca 24

<210> SEQ ID NO 152
<211> LENGTH: 24
<212> TYPE: DNA
<213> ORGANISM: Artificial Sequence
<220> FEATURE:
<223> OTHER INFORMATION: Primer Exons 7-8 Rev

<400> SEQUENCE: 152
ctatgccagc atttctcctt aatt 24

<210> SEQ ID NO 153
<211> LENGTH: 20
<212> TYPE: DNA
<213> ORGANISM: Artificial Sequence
<220> FEATURE:
<223> OTHER INFORMATION: Primer Exon 2a Fwd

<400> SEQUENCE: 153
gcgatgattc tgacatttgg 20

<210> SEQ ID NO 154
<211> LENGTH: 20
<212> TYPE: DNA
<213> ORGANISM: Artificial Sequence
<220> FEATURE:
<223> OTHER INFORMATION: primer Exon 2b Rev

<400> SEQUENCE: 154
ggaagctgca gtattcttct 20

<210> SEQ ID NO 155
<211> LENGTH: 20
<212> TYPE: DNA
<213> ORGANISM: Artificial Sequence
<220> FEATURE:
<223> OTHER INFORMATION: PolJ Forward Primer

<400> SEQUENCE: 155
accacactct ggggaacatc 20

<210> SEQ ID NO 156
<211> LENGTH: 20
<212> TYPE: DNA
<213> ORGANISM: Artificial Sequence
<220> FEATURE:
<223> OTHER INFORMATION: PolJ Reverse Primer

<400> SEQUENCE: 156
ctcgctgatg aggtctgtga 20

<210> SEQ ID NO 157
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (9)..(9)
<223> OTHER INFORMATION: L-serine glycosylated with a D-Lactose sugar
<220> FEATURE:
<221> NAME/KEY: MISC_FEATURE
<222> LOCATION: (11)..(11)
<223> OTHER INFORMATION: aminohexanoic acid
<220> FEATURE:
<221> NAME/KEY: MOD_RES
<222> LOCATION: (13)..(13)
<223> OTHER INFORMATION: bAla

<400> SEQUENCE: 157

Arg Xaa Arg Arg Xaa Arg Arg Phe Ser Arg Xaa Arg Xaa Arg
1 5 10

<210> SEQ ID NO 158
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (9)..(9)
<223> OTHER INFORMATION: L-serine glycosylated with a Galactose sugar
<220> FEATURE:
<221> NAME/KEY: MISC_FEATURE
<222> LOCATION: (11)..(11)
<223> OTHER INFORMATION: aminohexanoic acid
<220> FEATURE:
<221> NAME/KEY: MOD_RES
<222> LOCATION: (13)..(13)
<223> OTHER INFORMATION: bAla

<400> SEQUENCE: 158

Arg Xaa Arg Arg Xaa Arg Arg Phe Ser Arg Xaa Arg Xaa Arg
1 5 10

<210> SEQ ID NO 159
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (9)..(9)
<223> OTHER INFORMATION: L-serine glycosylated with a D-2-Acetylamino Glucose sugar
<220> FEATURE:
<221> NAME/KEY: MOD_RES
<222> LOCATION: (11)..(11)
<223> OTHER INFORMATION: bAla
<220> FEATURE:
<221> NAME/KEY: MISC_FEATURE
<222> LOCATION: (13)..(13)
<223> OTHER INFORMATION: aminohexanoic acid

<400> SEQUENCE: 159

Arg Xaa Arg Arg Xaa Arg Arg Phe Ser Arg Xaa Arg Xaa Arg
1 5 10

<210> SEQ ID NO 160
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (9)..(9)
<223> OTHER INFORMATION: L-serine glycosylated with a D-2-Acetylamino Glucose sugar
<220> FEATURE:
<221> NAME/KEY: MISC_FEATURE
<222> LOCATION: (11)..(11)

<223> OTHER INFORMATION: aminohexanoic acid
<220> FEATURE:
<221> NAME/KEY: MOD_RES
<222> LOCATION: (13)..(13)
<223> OTHER INFORMATION: bAla

<400> SEQUENCE: 160

Arg Xaa Arg Arg Xaa Arg Arg Phe Ser Arg Xaa Arg Xaa Arg
1 5 10

<210> SEQ ID NO 161
<211> LENGTH: 12
<212> TYPE: PRT
<213> ORGANISM: Artificial Sequence
<220> FEATURE:
<223> OTHER INFORMATION: Carrier peptide
<220> FEATURE:
<221> NAME/KEY: MOD_RES
<222> LOCATION: (2)..(2)
<223> OTHER INFORMATION: bAla
<220> FEATURE:
<221> NAME/KEY: MOD_RES
<222> LOCATION: (4)..(4)
<223> OTHER INFORMATION: bAla
<220> FEATURE:
<221> NAME/KEY: CARBOHYD
<222> LOCATION: (6)..(6)
<223> OTHER INFORMATION: L-serine glycosylated with D-Glucose sugar
<220> FEATURE:
<221> NAME/KEY: MOD_RES
<222> LOCATION: (8)..(8)
<223> OTHER INFORMATION: bAla
<220> FEATURE:
<221> NAME/KEY: MOD_RES
<222> LOCATION: (11)..(11)
<223> OTHER INFORMATION: bAla

<400> SEQUENCE: 161

Arg Xaa Arg Xaa Arg Ser Arg Xaa Arg Arg Xaa Arg
1 5 10

<210> SEQ ID NO 162
<211> LENGTH: 13
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (8)..(8)
<223> OTHER INFORMATION: D-serine glycosylated with D-Glucose sugar
<220> FEATURE:
<221> NAME/KEY: MOD_RES
<222> LOCATION: (10)..(10)
<223> OTHER INFORMATION: bAla
<220> FEATURE:
<221> NAME/KEY: MISC_FEATURE
<222> LOCATION: (12)..(12)
<223> OTHER INFORMATION: aminohexanoic acid

<400> SEQUENCE: 162

Arg Xaa Arg Arg Xaa Arg Arg Ser Arg Xaa Arg Xaa Arg
1 5 10

<210> SEQ ID NO 163

<211> LENGTH: 13
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (8)..(8)
<223> OTHER INFORMATION: L-serine glycosylated with an L-Glucose sugar
<220> FEATURE:
<221> NAME/KEY: MOD_RES
<222> LOCATION: (10)..(10)
<223> OTHER INFORMATION: bAla
<220> FEATURE:
<221> NAME/KEY: MISC_FEATURE
<222> LOCATION: (12)..(12)
<223> OTHER INFORMATION: aminohexanoic acid

<400> SEQUENCE: 163

Arg Xaa Arg Arg Xaa Arg Arg Ser Arg Xaa Arg Xaa Arg
1               5                   10

<210> SEQ ID NO 164
<211> LENGTH: 13
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (8)..(8)
<223> OTHER INFORMATION: L-serine glycosylated with a D-Mannose sugar
<220> FEATURE:
<221> NAME/KEY: MOD_RES
<222> LOCATION: (10)..(10)
<223> OTHER INFORMATION: bAla
<220> FEATURE:
<221> NAME/KEY: MISC_FEATURE
<222> LOCATION: (12)..(12)
<223> OTHER INFORMATION: aminohexanoic acid

<400> SEQUENCE: 164

Arg Xaa Arg Arg Xaa Arg Arg Ser Arg Xaa Arg Xaa Arg
1               5                   10

<210> SEQ ID NO 165
<211> LENGTH: 13
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (8)..(8)
<223> OTHER INFORMATION: L-serine glycosylated with a D-Lactose sugar
<220> FEATURE:
<221> NAME/KEY: MOD_RES
<222> LOCATION: (10)..(10)
<223> OTHER INFORMATION: bAla
<220> FEATURE:
<221> NAME/KEY: MISC_FEATURE
<222> LOCATION: (12)..(12)
<223> OTHER INFORMATION: aminohexanoic acid

<400> SEQUENCE: 165

Arg Xaa Arg Arg Xaa Arg Arg Ser Arg Xaa Arg Xaa Arg
1 5 10

<210> SEQ ID NO 166
<211> LENGTH: 13
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (8)..(8)
<223> OTHER INFORMATION: L-asparagine glycosylated with a
D-2-Acetylamino Glucose sugar
<220> FEATURE:
<221> NAME/KEY: MOD_RES
<222> LOCATION: (10)..(10)
<223> OTHER INFORMATION: bAla
<220> FEATURE:
<221> NAME/KEY: MISC_FEATURE
<222> LOCATION: (12)..(12)
<223> OTHER INFORMATION: aminohexanoic acid

<400> SEQUENCE: 166

Arg Xaa Arg Arg Xaa Arg Arg Asn Arg Xaa Arg Xaa Arg
1 5 10

<210> SEQ ID NO 167
<211> LENGTH: 13
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (8)..(8)
<223> OTHER INFORMATION: L-serine glycosylated with a Galactose sugar
<220> FEATURE:
<221> NAME/KEY: MOD_RES
<222> LOCATION: (10)..(10)
<223> OTHER INFORMATION: bAla
<220> FEATURE:
<221> NAME/KEY: MISC_FEATURE
<222> LOCATION: (12)..(12)
<223> OTHER INFORMATION: aminohexanoic acid

<400> SEQUENCE: 167

Arg Xaa Arg Arg Xaa Arg Arg Ser Arg Xaa Arg Xaa Arg
1 5 10

<210> SEQ ID NO 168
<211> LENGTH: 13
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (8)..(8)
<223> OTHER INFORMATION: D-serine glycosylated with D-Glucose sugar
<220> FEATURE:
<221> NAME/KEY: MISC_FEATURE
<222> LOCATION: (10)..(10)
<223> OTHER INFORMATION: aminohexanoic acid
<220> FEATURE:
<221> NAME/KEY: MOD_RES
<222> LOCATION: (12)..(12)
<223> OTHER INFORMATION: bAla

<400> SEQUENCE: 168

Arg Xaa Arg Arg Xaa Arg Arg Ser Arg Xaa Arg Xaa Arg
1 5 10

<210> SEQ ID NO 169
<211> LENGTH: 13
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (8)..(8)
<223> OTHER INFORMATION: L-serine glycosylated with an L-Glucose sugar
<220> FEATURE:
<221> NAME/KEY: MISC_FEATURE
<222> LOCATION: (10)..(10)
<223> OTHER INFORMATION: aminohexanoic acid
<220> FEATURE:
<221> NAME/KEY: MOD_RES
<222> LOCATION: (12)..(12)
<223> OTHER INFORMATION: bAla

<400> SEQUENCE: 169

Arg Xaa Arg Arg Xaa Arg Arg Ser Arg Xaa Arg Xaa Arg
1 5 10

<210> SEQ ID NO 170
<211> LENGTH: 13
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (8)..(8)
<223> OTHER INFORMATION: L-serine glycosylated with a D-Mannose sugar
<220> FEATURE:
<221> NAME/KEY: MISC_FEATURE
<222> LOCATION: (10)..(10)
<223> OTHER INFORMATION: aminohexanoic acid
<220> FEATURE:
<221> NAME/KEY: MOD_RES
<222> LOCATION: (12)..(12)
<223> OTHER INFORMATION: bAla

<400> SEQUENCE: 170

Arg Xaa Arg Arg Xaa Arg Arg Ser Arg Xaa Arg Xaa Arg
1 5 10

<210> SEQ ID NO 171
<211> LENGTH: 13
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (8)..(8)
<223> OTHER INFORMATION: L-serine glycosylated with a D-Lactose sugar
<220> FEATURE:
<221> NAME/KEY: MISC_FEATURE
<222> LOCATION: (10)..(10)
<223> OTHER INFORMATION: aminohexanoic acid
<220> FEATURE:
<221> NAME/KEY: MOD_RES
<222> LOCATION: (12)..(12)
<223> OTHER INFORMATION: bAla

<400> SEQUENCE: 171

Arg Xaa Arg Arg Xaa Arg Arg Ser Arg Xaa Arg Xaa Arg
1 5 10

<210> SEQ ID NO 172
<211> LENGTH: 13
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (8)..(8)
<223> OTHER INFORMATION: L-asparagine glycosylated with a
D-2-Acetylamino Glucose sugar

```
<220> FEATURE:
<221> NAME/KEY: MISC_FEATURE
<222> LOCATION: (10)..(10)
<223> OTHER INFORMATION: aminohexanoic acid
<220> FEATURE:
<221> NAME/KEY: MOD_RES
<222> LOCATION: (12)..(12)
<223> OTHER INFORMATION: bAla

<400> SEQUENCE: 172

Arg Xaa Arg Arg Xaa Arg Arg Asn Arg Xaa Arg Xaa Arg
1               5                   10


<210> SEQ ID NO 173
<211> LENGTH: 13
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (8)..(8)
<223> OTHER INFORMATION: L-serine glycosylated with a Galactose sugar
<220> FEATURE:
<221> NAME/KEY: MISC_FEATURE
<222> LOCATION: (10)..(10)
<223> OTHER INFORMATION: aminohexanoic acid
<220> FEATURE:
<221> NAME/KEY: MOD_RES
<222> LOCATION: (12)..(12)
<223> OTHER INFORMATION: bAla

<400> SEQUENCE: 173

Arg Xaa Arg Arg Xaa Arg Arg Ser Arg Xaa Arg Xaa Arg
1               5                   10


<210> SEQ ID NO 174
<211> LENGTH: 13
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (8)..(8)
<223> OTHER INFORMATION: L-serine glycosylated with a D-2-Acetylamino
      Glucose sugar
<220> FEATURE:
<221> NAME/KEY: MOD_RES
<222> LOCATION: (10)..(10)
<223> OTHER INFORMATION: bAla
<220> FEATURE:
<221> NAME/KEY: MISC_FEATURE
<222> LOCATION: (12)..(12)
<223> OTHER INFORMATION: aminohexanoic acid

<400> SEQUENCE: 174

Arg Xaa Arg Arg Xaa Arg Arg Ser Arg Xaa Arg Xaa Arg
```

1 5 10

<210> SEQ ID NO 175
<211> LENGTH: 13
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: aminohexanoic acid
<220> FEATURE:
<221> NAME/KEY: MOD_RES
<222> LOCATION: (5)..(5)
<223> OTHER INFORMATION: bAla
<220> FEATURE:
<221> NAME/KEY: CARBOHYD
<222> LOCATION: (8)..(8)
<223> OTHER INFORMATION: L-serine glycosylated with a D-2-Acetylamino
Glucose sugar
<220> FEATURE:
<221> NAME/KEY: MISC_FEATURE
<222> LOCATION: (10)..(10)
<223> OTHER INFORMATION: aminohexanoic acid
<220> FEATURE:
<221> NAME/KEY: MOD_RES
<222> LOCATION: (12)..(12)
<223> OTHER INFORMATION: bAla

<400> SEQUENCE: 175

Arg Xaa Arg Arg Xaa Arg Arg Ser Arg Xaa Arg Xaa Arg
1 5 10

<210> SEQ ID NO 176
<211> LENGTH: 11
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: any non-natural amino acid
<220> FEATURE:
<221> NAME/KEY: MISC_FEATURE
<222> LOCATION: (5)..(5)
<223> OTHER INFORMATION: any non-natural amino acid

<400> SEQUENCE: 176

Arg Xaa Arg Arg Xaa Arg Arg Arg Arg Arg Arg
1 5 10

<210> SEQ ID NO 177
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: any non-natural amino acid
<220> FEATURE:
<221> NAME/KEY: MISC_FEATURE
<222> LOCATION: (5)..(5)
<223> OTHER INFORMATION: any non-natural amino acid

<400> SEQUENCE: 177

Arg Xaa Arg Arg Xaa Arg Arg Arg Arg Arg Arg Arg Arg Arg
1 5 10

<210> SEQ ID NO 178
<211> LENGTH: 17
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: any non-natural amino acid
<220> FEATURE:
<221> NAME/KEY: MISC_FEATURE
<222> LOCATION: (5)..(5)
<223> OTHER INFORMATION: any non-natural amino acid

<400> SEQUENCE: 178

```
Arg Xaa Arg Arg Xaa Arg Arg Arg Arg Arg Arg Arg Arg Arg Arg Arg
1               5                   10                  15

Arg
```

<210> SEQ ID NO 179
<211> LENGTH: 20
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: any non-natural amino acid
<220> FEATURE:
<221> NAME/KEY: MISC_FEATURE
<222> LOCATION: (5)..(5)
<223> OTHER INFORMATION: any non-natural amino acid

<400> SEQUENCE: 179

```
Arg Xaa Arg Arg Xaa Arg Arg Arg Arg Arg Arg Arg Arg Arg Arg Arg
1               5                   10                  15

Arg Arg Arg Arg
            20
```

<210> SEQ ID NO 180
<211> LENGTH: 10
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (3)..(3)
<223> OTHER INFORMATION: any non-natural amino acid
<220> FEATURE:
<221> NAME/KEY: MISC_FEATURE
<222> LOCATION: (6)..(6)
<223> OTHER INFORMATION: any non-natural amino acid

<400> SEQUENCE: 180

```
Arg Arg Xaa Arg Arg Xaa Arg Arg Arg Arg
1               5                   10
```

<210> SEQ ID NO 181
<211> LENGTH: 12
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (3)..(3)
<223> OTHER INFORMATION: any non-natural amino acid
<220> FEATURE:

<221> NAME/KEY: MISC_FEATURE
<222> LOCATION: (6)..(6)
<223> OTHER INFORMATION: any non-natural amino acid

<400> SEQUENCE: 181

Arg Arg Xaa Arg Arg Xaa Arg Arg Arg Arg Arg Arg
1 5 10

<210> SEQ ID NO 182
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (3)..(3)
<223> OTHER INFORMATION: any non-natural amino acid
<220> FEATURE:
<221> NAME/KEY: MISC_FEATURE
<222> LOCATION: (6)..(6)
<223> OTHER INFORMATION: any non-natural amino acid

<400> SEQUENCE: 182

Arg Arg Xaa Arg Arg Xaa Arg Arg Arg Arg Arg Arg Arg Arg
1 5 10

<210> SEQ ID NO 183
<211> LENGTH: 16
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (3)..(3)
<223> OTHER INFORMATION: any non-natural amino acid
<220> FEATURE:
<221> NAME/KEY: MISC_FEATURE
<222> LOCATION: (6)..(6)
<223> OTHER INFORMATION: any non-natural amino acid

<400> SEQUENCE: 183

Arg Arg Xaa Arg Arg Xaa Arg Arg Arg Arg Arg Arg Arg Arg Arg Arg
1 5 10 15

<210> SEQ ID NO 184
<211> LENGTH: 10
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: any non-natural amino acid
<220> FEATURE:
<221> NAME/KEY: MISC_FEATURE
<222> LOCATION: (6)..(6)
<223> OTHER INFORMATION: any non-natural amino acid

<400> SEQUENCE: 184

Arg Xaa Arg Arg Arg Xaa Arg Arg Arg Arg
1 5 10

<210> SEQ ID NO 185
<211> LENGTH: 12
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: any non-natural amino acid
<220> FEATURE:
<221> NAME/KEY: MISC_FEATURE
<222> LOCATION: (6)..(6)
<223> OTHER INFORMATION: any non-natural amino acid

<400> SEQUENCE: 185

Arg Xaa Arg Arg Arg Xaa Arg Arg Arg Arg Arg Arg
1 5 10

<210> SEQ ID NO 186
<211> LENGTH: 14
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: any non-natural amino acid
<220> FEATURE:
<221> NAME/KEY: MISC_FEATURE
<222> LOCATION: (6)..(6)
<223> OTHER INFORMATION: any non-natural amino acid

<400> SEQUENCE: 186

Arg Xaa Arg Arg Arg Xaa Arg Arg Arg Arg Arg Arg Arg Arg
1 5 10

<210> SEQ ID NO 187
<211> LENGTH: 16
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: any non-natural amino acid
<220> FEATURE:
<221> NAME/KEY: MISC_FEATURE
<222> LOCATION: (6)..(6)
<223> OTHER INFORMATION: any non-natural amino acid

<400> SEQUENCE: 187

Arg Xaa Arg Arg Arg Xaa Arg Arg Arg Arg Arg Arg Arg Arg Arg Arg
1 5 10 15

<210> SEQ ID NO 188
<211> LENGTH: 12
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: any non-natural amino acid
<220> FEATURE:
<221> NAME/KEY: MISC_FEATURE
<222> LOCATION: (11)..(11)
<223> OTHER INFORMATION: any non-natural amino acid

<400> SEQUENCE: 188

Arg Xaa Arg Arg Arg Arg Arg Arg Arg Arg Xaa Arg
1 5 10

<210> SEQ ID NO 189

<211> LENGTH: 16
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: any non-natural amino acid
<220> FEATURE:
<221> NAME/KEY: MISC_FEATURE
<222> LOCATION: (15)..(15)
<223> OTHER INFORMATION: any non-natural amino acid

<400> SEQUENCE: 189

Arg Xaa Arg Arg Arg Arg Arg Arg Arg Arg Arg Arg Arg Arg Xaa Arg
1 5 10 15

<210> SEQ ID NO 190
<211> LENGTH: 20
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: any non-natural amino acid
<220> FEATURE:
<221> NAME/KEY: MISC_FEATURE
<222> LOCATION: (19)..(19)
<223> OTHER INFORMATION: any non-natural amino acid

<400> SEQUENCE: 190

Arg Xaa Arg Arg Arg Arg Arg Arg Arg Arg Arg Arg Arg Arg Arg Arg
1 5 10 15

Arg Arg Xaa Arg
20

<210> SEQ ID NO 191
<211> LENGTH: 24
<212> TYPE: PRT
<213> ORGANISM: Artificial Sequence
<220> FEATURE:
<223> OTHER INFORMATION: Carrier peptide
<220> FEATURE:
<221> NAME/KEY: MISC_FEATURE
<222> LOCATION: (2)..(2)
<223> OTHER INFORMATION: any non-natural amino acid
<220> FEATURE:
<221> NAME/KEY: MISC_FEATURE
<222> LOCATION: (23)..(23)
<223> OTHER INFORMATION: any non-natural amino acid

<400> SEQUENCE: 191

Arg Xaa Arg Arg Arg Arg Arg Arg Arg Arg Arg Arg Arg Arg Arg Arg
1 5 10 15

Arg Arg Arg Arg Arg Arg Xaa Arg
20

CELL PENETRATING PEPTIDES

CROSS-REFERENCE TO RELATED APPLICATIONS

This application is a continuation of U.S. application Ser. No. 16/486,671 filed on Aug. 16, 2019, which is a national stage filing under 35 U.S.C. § 371 of PCT Application No. PCT/GB2018/050423, filed Feb. 16, 2018, which claims the benefit of priority to G.B. Application No. 1702631.1, filed Feb. 17, 2017, G.B. Application No. 1704947.9, filed Mar. 28, 2017, and G.B. Application No. 1711372.1, filed Jul. 14, 2017. The entire contents of PCT Application No. PCT/GB2018/050423 is hereby incorporated by reference herein in their entirety.

SEQUENCE LISTING

The instant application contains a Sequence Listing, which has been submitted in ASCII format via EFS-Web and is hereby incorporated by reference in its entirety. Said ASCII copy, created on Jan. 31, 2020, is named Sequence listing final_5021339.txt and is 92,001 bytes in size.

TECHNICAL FIELD

The present invention relates to peptides, in particular cell penetrating peptides, and to conjugates of such cell penetrating peptides with a therapeutic molecule. The present invention further relates to use of such peptides or conjugates in methods of treatment or as a medicament, especially in the treatment of genetic disorders of the central nervous system.

BACKGROUND

Disruption of alternative splicing underlies many diseases, and modulation of splicing using antisense oligonucleotides can have therapeutic implications. Splice-switching antisense oligonucleotides (SSOs) are emerging treatments for neuromuscular diseases, with several SSOs currently undergoing clinical trials for conditions such as spinal muscular atrophy (SMA) and Duchenne muscular dystrophy (DMD), where antisense-mediated exon skipping can restore the open reading frame and allow the synthesis of partly functional proteins instead of non-functional ones.

However, therapeutic development of these promising antisense therapeutics has been hampered by poor tissue penetration and cellular uptake. This is especially the case where crossing of the blood-brain barrier (BBB) to reach targets in the central nervous system (CNS) is required.

In SMA, for example, therapeutic SSOs can be used to target the regulatory elements of splicing. One such target is the intronic splice silencer N1 (ISS-N1) site within intron 7 of the SMN2 gene. SSO targeting of this site enhances exon 7 inclusion to generate a fully functional full length SMN2 (FLSMN2) mRNA and hence up-regulates SMN protein production (1,2). One such 2'-O-methexyethyl phosphorothioate SSO is being developed by Ionis Pharmaceuticals and Biogen for the treatment of SMA in infants and children, which has progressed to phase III clinical trials after promising data from open label phase II studies (3). This drug (Nusinersen) has just been approved for clinical use by the FDA in the USA.

However, currently this type of SSO therapeutic is not able to cross the blood-brain barrier (BBB) to reach the target motor neurons, therefore delivery of the therapeutic must be via intrathecal injection to obtain broad CNS distribution. In addition, the currently available SSO therapeutics are inefficient and require high doses in order to effect any physiological changes.

Furthermore, it has become recognized that restoration of the SMN2 gene is also essential in the peripheral muscles in addition to within the brain and spinal cord compartments in order for long term rescue of a severely affected SMA mouse (4). SSO therapeutic delivery must account for both of these needs.

Thus there is a strong impetus for the development of efficient delivery systems for therapeutic SSOs both to facilitate entry into brain and spinal cord via the circulation and to penetrate target cells better in both periphery and in the CNS, as well as to enhance the efficiency of the therapeutic SSOs in order to reduce drug doses.

The use of viruses as delivery vehicles has been suggested, however this is limited due to the immunotoxicity of the viral coat protein and potential oncogenic effects (5). Alternatively, a range of non-viral CNS delivery vectors have been developed, amongst which peptides have shown the most promise due to their small size, low toxicity, targeting specificity and ability of trans-capillary delivery of large bio-cargoes (6-8). Several peptides have been reported for their ability to permeate cells either alone or carrying a bio-cargo (6, 7).

For several years, cell-penetrating peptides (CPPs) have been used as conjugates of certain types of SSOs (in particular charge neutral phosphorodiamidate morpholino oligomer (PMO) and peptide nucleic acids (PNA)) to enhance their cell delivery by effectively carrying them across cell membranes to reach their pre-mRNA target sites in the cell nucleus. It has been shown that PMO therapeutics conjugated to certain arginine-rich CPPs (known as P-PMOs) can enhance dystrophin production in skeletal muscles following systemic administration in a mdx mouse model of DMD (9-11).

In particular, arginine-rich CPPs known as PNA/PMO internalization peptides (Pips), comprised of two arginine-rich sequences separated by a central short hydrophobic sequence have been developed. These 'Pip' peptides were designed to improve serum stability whilst maintaining a high level of exon skipping, initially by attachment to a PNA cargo (12). Further derivatives of these peptides were designed as conjugates of PMOs, which were shown to lead to high body-wide skeletal muscle dystrophin production, and importantly also including the heart, following systemic administration (13).

More recently, promising results have been obtained from the use of a particular 'Pip' peptide conjugate for the treatment of SMA: Pip6a-PMO. This peptide conjugate was administered by systemic delivery into adult, non-affected mice that maintain a copy of the human SMN2 transgene and the production of full length SMN2 transcript was measured by quantitative polymerase chain reaction (qPCR). This experiment showed that use of a Pip6a-PMO conjugate was able to generate significant exon inclusion of SMN2 exon 7 both in skeletal muscles as well as in the brain and spinal cord. A greater than 30% increase in full-length SMN2 transcripts was observed in all areas of the brain, spinal cord, and skeletal muscles (14).

However, this 'Pip'-PMO conjugate, when systemically injected into mice, requires a high dose which results in insufficient tolerability from the mice and therefore does not provide a large enough dosing range for therapeutic development (14).

The present inventors have now identified, synthesized and tested a number of cell penetrating peptides according to the present invention. These peptides maintain good levels of cell penetration as well as tissue penetration, in skeletal muscles as well as in compartments of the brain and spinal cord. This action of these peptides further gives rise to enhanced levels of exon inclusion in both skeletal muscles as well as in compartments of the brain and spinal cord relative to previously available carrier peptides.

In addition, the present peptides show a shorter recovery time following systemic injection into mice, indicating that the peptides of the invention may be more applicable as a therapeutic treatment for humans than previous cell penetrating peptides. A shorter recovery time is advantageous in having minimal disruption to patient's everyday lives and increasing quality of life. It also reduces the burden on healthcare facilities in accommodating patients whilst they are treated. Furthermore, the present peptides are demonstrated to show reduced toxicity following similar systemic injection into mice when compared with previous cell penetrating peptides. This also indicates that the peptides of the invention are more suitable for use as a therapy for humans that previously available peptides. Reduced toxicity means that the peptides can be used safely as a therapy.

SUMMARY OF THE INVENTION

According to a first aspect of the present invention, there is provided a peptide comprising at least one directly glycosylated amino acid residue and one or more arginine-rich arm domains, wherein the total length of the peptide is 40 amino acid residues or less.

According to a second aspect of the present invention, there is provided a conjugate comprising the peptide of the first aspect covalently linked to a therapeutic molecule.

According to a third aspect of the present invention, there is provided a pharmaceutical composition comprising the conjugate of the second aspect.

According to a fourth aspect of the present invention, there is provided a conjugate according to the second aspect for use as a medicament.

According to a fifth aspect of the present invention, there is provided a method of treating a disease in a subject comprising administering the conjugate of the second aspect to the subject in a therapeutically effective amount.

According to a sixth aspect of the present invention, there is provided an isolated nucleic acid encoding the peptide of the first aspect or the conjugate of the second aspect.

According to an seventh aspect of the present invention, there is provided an expression vector comprising the nucleic acid sequence of the sixth aspect.

According to an eighth aspect of the present invention, there is provided a host cell comprising the expression vector of the seventh aspect.

DETAILED DESCRIPTION

The inventors have produced a series of peptides that are suitable for use as carrier peptides to deliver therapeutic molecules into cells. These peptides of the invention are particularly suited to delivery of therapeutic molecules into cells of the central nervous system in addition to delivery of therapeutic molecules into cells in peripheral tissues.

Surprisingly, the inventors have discovered that the presence of at least one directly glycosylated amino acid residue in combination with short arginine-rich arm sequences produces peptides which, when delivered as a conjugate with an antisense oligonucleotide therapeutic into cells, or when administered in vivo, provide enhanced cell penetration in skeletal muscles, as well as enhanced penetration into many compartments of the brain and spinal cord compared with currently available cell penetrating peptides.

In the context of the disease SMA, enhanced cell penetration by peptides of the invention linked to a suitable therapeutic molecule can be shown by increased exon inclusion, which causes cells to produce more of the full length SMN2 gene transcript instead of the truncated version. The presence of more full length SMN2 enables some level of muscle function to be restored in individuals suffering from this disease. The peptides of the present invention, when used as a conjugate with an antisense oligonucleotide therapeutic designed to target the SMN2 gene, are shown herein to have significantly increased cell penetration when compared with currently available peptides conjugate to the same antisense oligonucleotide therapeutic. This is demonstrated in the present invention by increased exon inclusion in the SMN2 gene in many compartments of the brain and spinal cord, and also skeletal muscle. In vivo, the results described herein show an increase in exon inclusion of up to 60% when using peptide conjugates of the invention compared with the exon inclusion results of the same antisense oligonucleotide therapeutic conjugated to a currently available peptide. This is a significant improvement in the ability of such peptide carriers to penetrate cells of the central nervous system, which has historically been a difficult area in which to target therapeutics to due to the presence of the blood brain barrier. Increased cell penetration may allow the present peptides to carry therapeutic molecules into areas of the brain and central nervous system where direct therapeutic action has thus far not been available. This is of particular interest in the treatment of genetic disorders such as SMA, DMD, Alzheimer's, Parkinson's, etc.

Without wishing to be bound by theory, the inventors believe that the inclusion of at least one glycosylated amino acid residue may allow the peptide carriers to bind to sugar transporters (such as GLUT 1) located in the blood brain barrier. This transporter binding may assist the peptides across the blood brain barrier, thereby facilitating improved delivery of any conjugated therapeutic molecule directly into the central nervous system. Alternatively, it is thought that another property of the glycosylated residue, such as its effect in altering the hydrophobic/hydrophilic balance of the peptide, may result in enhanced blood brain barrier uptake by adsorptive transcytosis.

It was completely unanticipated that such a glycosylation modification direct to the amino acid sequence would boost the ability of an arginine-rich carrier cell-penetrating peptide to transport a therapeutic molecule cargo, such as an oligonucleotide, into both brain and spinal cord. Furthermore, it was unexpected that such transport would be significantly enhanced so as to result in a therapeutic molecule such as an antisense oligonucleotide successfully increasing exon inclusion in brain and spinal cord compartments of the central nervous system as demonstrated herein.

For the avoidance of doubt, and in order to clarify the way in which the present disclosure is to be interpreted, certain terms used in accordance with the present invention will now be defined further.

The invention includes any combination of the aspects and features described except where such a combination is clearly impermissible or expressly avoided.

The section headings used herein are for organisational purposes only and are not to be construed as limiting the subject matter described.

Amino Acid Nomenclature

References to '*' throughout denote direct glycosylation of the relevant amino acid residue.

References to 'X' throughout denote the non-natural amino acid residue aminohexanoic acid.

References to 'B' throughout denote the non-natural amino acid residue beta-alanine.

References to 'Hyp' throughout denote the amino acid residue hydroxyproline.

References to 'Ac' throughout denote acetylation of the relevant amino acid residue.

References to 'Cy' throughout denote the non-natural amino acid 1-(amino)cyclohexanecarboxylic acid.

References to 'Az' throughout denote the non-natural amino acid 3-azetidine-carboxylic acid.

References to 'Z' throughout denote the non-natural amino acid tetrahydroisoquinoline-3-carboxylic acid (TIC).

References to 'non-natural' amino acid denote any amino acid that is not naturally occurring and includes synthetic amino acids, modified amino acids, spacers, and non-peptide bonded spacers. These non-natural amino acids may also be referred to as amino acid analogues, and the term 'amino acid analogue' is used interchangeably with the term 'non-natural amino acid' throughout this specification. Suitable non-natural amino acids that may be used in the present invention are: beta-alanine (B), aminohexanoic acid (X), tetrahydroisoquinoline-3-carboxylic acid (TIC), 4-aminobutyryl (Aib), 1-(amino)cyclohexanecarboxylic acid (Cy), and 3-azetidine-carboxylic acid (Az), for example.

References to other capital letters throughout denote the relevant amino acid residue in accordance with the accepted alphabetic amino acid code.

Glycosylated Amino Acid Residue

The present invention defines a peptide comprising at least one directly glycosylated amino acid residue.

By 'directly glycosylated' it is meant that the sugar is covalently bonded to an atom in the amino acid residue.

Suitably the sugar is covalently bonded to an atom in the amino acid residue without the presence of an intermediate spacer moiety.

By 'spacer moiety' we mean any chemical structure, for example: alkyl, alkenyl, alkynyl, aryl, ether, thioether, triazole, amide, carboxamide, urea, thiourea, semicarbazide, carbazide, hydrazine, oxime, phosphate, phosphoramidate, thiophosphate, boranophosphate or iminophosphate, and the like, which may be placed between the amino acid residue and the sugar.

Suitably, the at least one directly glycosylated amino acid residue is O-linked glycosylated, N-linked glycosylated or S-linked glycosylated.

Suitably, the at least one directly glycosylated amino acid residue is glycosylated at any suitable functional group present in its side chain.

Suitably, the at least one directly glycosylated amino acid residue may be glycosylated at one or more functional groups present in its side chain.

Therefore, suitably the at least one directly glycosylated amino acid residue may be glycosylated at multiple functional groups present in its side chain.

Suitably, the at least one directly glycosylated amino acid residue is glycosylated at an OH, $NH_2$, $NH_3$ or SH functional group present in its side chain.

Suitably the at least one directly glycosylated amino acid residue is selected from serine, cysteine, threonine, asparagine, glutamine, aminoproline, hydroxyproline, tyrosine, lysine, or amino acid analogues thereof.

Suitably, the at least one directly glycosylated amino acid residue is glycosylated at an OH functional group present in its side chain.

Suitably, the at least one directly glycosylated amino acid residue is selected from a glycosylated serine, asparagine, threonine, or tyrosine, or amino acid analogues thereof.

In one embodiment, the at least one directly glycosylated amino acid residue is glycosylated serine. In one embodiment, each of the directly glycosylated amino acid residues is glycosylated serine.

In one embodiment, the at least one directly glycosylated amino acid residue is glycosylated asparagine. In one embodiment, each of the directly glycosylated amino acid residues is glycosylated asparagine.

Suitably, the at least one directly glycosylated amino acid residue may be selected from L or D enantiomers.

Suitably, the glycosylated serine may be selected from glycosylated L-Serine, or glycosylated D-Serine.

Suitably, the glycosylated asparagine may be selected from glycosylated L-Asparagine, or glycosylated D-Asparagine.

Suitably, the peptide comprises 1-3 directly glycosylated amino acid residues. Suitably, the directly glycosylated amino acid residues may be contiguous with one another.

Suitably, the peptide may comprise directly glycosylated amino acid residue sequences selected from the group consisting of: aa*, aa*aa*, and aa*aa*aa* (where "aa" represents an amino acid residue).

In one embodiment, the peptide comprises only 1 directly glycosylated amino acid residue.

The at least one directly glycosylated amino acid residue may be glycosylated with any suitable sugar. Suitably the glycosylating sugar may be a monosaccharide, disaccharide, trisaccharide, tetrasaccharide, oligosaccharide or polysaccharide.

Suitable sugars for glycosylation are, for example; glucose, allose, altrose, idose, gulose, talose, xylose, mannose, galactose, mannoseamine, glucosamine, galactosamine, N-acetylgalactosamine, N-acetylglucosamine, 2-Acetylamino glucose, D-2-Acetylamino Glucose, lactose, maltose, isomaltose, or trehalose or sialic acid.

Suitably, the at least one directly glycosylated amino acid residue is glycosylated with glucose, 2-Acetylamino glucose, D-2-Acetylamino Glucose, mannose, lactose, or galactose.

Suitably, the sugars used for glycosylation of the (or each) glycosylated amino acid residue may be modified or unmodified sugars.

The sugars used for glycosylation of the (or each) glycosylated amino acid residue may be selected from L or D enantiomers, α or β anomers, or any other stereochemical variant.

In one embodiment, the sugar used for glycosylation of the (or each) glycosylated amino acid residue is a D enantiomer.

In one embodiment, the sugar used for glycosylation of the (or each) glycosylated amino acid residue is a β anomer.

In one embodiment, the at least one amino acid residue is directly glycosylated with glucose. Therefore in one embodiment the at least one amino acid residue is directly glucosylated.

In one embodiment, the at least one amino acid residue is directly glucosylated with β-D glucose.

In one embodiment, the at least one amino acid residue is directly glucosylated with D-2-Acetylamino Glucose Suitably the sugar is covalently bonded to an atom of the at least one amino acid residue. Suitably the sugar is covalently bonded to the amino acid residue via an —O— linkage, —S— linkage or —N-linkage.

By the term '—O-linkage' it is meant that the sugar is covalently bonded to an Oxygen atom present in the side chain of the at least one amino acid residue.

By the term '—N-linkage' it is meant that the sugar is covalently bonded to a Nitrogen atom present in the side chain of the at least one amino acid residue.

By the term '—S-linkage' it is meant that the sugar is covalently bonded to a Sulphur atom present in the side chain of the at least one amino acid residue.

In one embodiment, the sugar is covalently bonded to the amino acid residue by via an —O-linkage.

In one embodiment, the sugar is glucose and is covalently bonded to the at least one amino acid residue by and —O-linkage. In one embodiment, the at least one directly glycosylated amino acid residue is β-D-glucosyl serine.

A β-D-glucosyl serine has the following chemical structure:

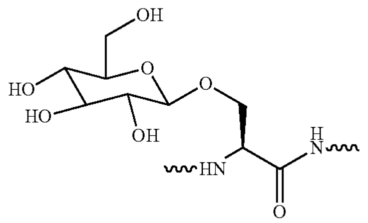

In one embodiment, the glycosylated amino acid residue is L-serine glycosylated with a D-Glucose sugar.

In one embodiment, the glycosylated amino acid residue is D-serine glycosylated with a D-Glucose sugar.

In one embodiment, the at least one directly glycosylated amino acid residue is β-D-2-Acetylamino glucosyl asparagine.

In one embodiment, the glycosylated amino acid residue is L-asparagine glycosylated with a D-2-Acetylamino Glucose sugar.

In one embodiment, the glycosylated amino acid residue is D-asparagine glycosylated with a D-2-Acetylamino Glucose sugar.

In one embodiment, the peptide comprises one directly glycosylated serine residue.

In one embodiment, the peptide comprises one directly glycosylated asparagine residue.

Optionally, the at least one directly glycosylated amino acid residue may be present with, and contiguous with, one or more hydrophobic core domains as defined below.

Suitably, the at least one directly glycosylated amino acid residue is contiguous with one hydrophobic core domain Alternatively, the at least one directly glycosylated amino acid residue may be present without a contiguous hydrophobic core domain.

In a suitable embodiment the at least one directly glycosylated amino acid residue is contiguous with an arginine-rich arm domain.

Suitably, the at least one directly glycosylated amino acid residue, optionally together with one or more hydrophobic core domains, is flanked on both sides by arginine-rich arm domains. Therefore, suitably, the peptide may comprise the following structures:

[arginine-rich arm domain]-[aa*]-[hydrophobic core domain]-[arginine-rich arm domain]

[arginine-rich arm domain]-[hydrophobic core domain]-[aa*]-[arginine-rich arm domain]

Alternatively, or additionally, the peptide may comprise the following structure:

[arginine-rich arm domain]-[aa*]-[arginine-rich arm domain]

Alternatively, the at least one directly glycosylated amino acid residue, optionally together with one or more hydrophobic core domains, is flanked on one side by an arginine-rich arm domain.

Therefore, suitably, the peptide may comprise the following structures:

[aa*]-[hydrophobic core domain]-[arginine-rich arm domain]

[hydrophobic core domain]-[aa*]-[arginine-rich arm domain]

[arginine-rich arm domain]-[aa*]-[hydrophobic core domain]

[arginine-rich arm domain]-[hydrophobic core domain]-[aa*]

Alternatively, or additionally, the peptide may comprise the following structure:

[aa*]-[arginine-rich arm domain]

[arginine-rich arm domain]-[aa*]

Suitably, the peptide may comprise more than one of the above-described structures and in any combination. Further peptide structures within the scope of the present invention are described below.

Arm Domains

The present invention defines a peptide comprising one or more arginine-rich arm domains.

An 'arginine-rich' arm domain may comprise at least 30% arginine residues. For example, an arginine-rich arm domain may comprise at least 35%, at least 40%, at least 45%, or at least 50% arginine residues. Suitably an arginine-rich arm domain may comprise at least 55%, at least 60%, at least 65%, at least 70%, at least 75%, at least 80%, at least 85%, at least 90%, or at least 95%, or more, arginine residues. In a suitable embodiment an arginine-rich arm domain may comprise 100% arginine residues.

An arginine-rich arm domain may comprise more Arginine residues than any other single amino acid residue.

Suitably the arginine-rich arm domains comprise a combined total of between 5-10 Arginine residues, suitably between 8-10 Arginine residues. Thus it will be appreciated that the arginine-rich arm domains present in a peptide of the invention may comprise a combined total of 5 arginine residues, a combined total of 6 arginine residues, a combined total of 7 arginine residues, a combined total of 8 arginine residues, a combined total of 9 arginine residues, or a combined total of 10 arginine residues.

Suitably the arginine-rich arm domains comprise no more than 3 contiguous Arginine residues, suitably no more than 2 contiguous Arginine residues.

Suitably, each arginine-rich arm domain comprises a length of between 1-12 amino acid residues, suitably a length of between 6-9 amino acid residues.

Suitably the arginine-rich arm domains are cationic.

Suitably, the arginine-rich arm domains comprise amino acid residues selected from the group consisting of: arginine, alanine, beta-alanine, histidine, proline, glycine, cysteine, tryptophan, hydroxyproline, aminohexanoic acid, 3-azetidine-carboxylic acid (Az), and 1-(amino)cyclohexanecarboxylic acid (Cy), and amino acid analogues thereof, or any other non-natural amino acid. Suitably, the arginine-rich arm domains comprise amino acid residues selected from the group consisting of: arginine, beta-alanine and aminohexanoic acid.

Suitably, the arginine-rich arm domains consist of amino acid residues selected from the group consisting of: arginine, alanine, beta-alanine, histidine, proline, glycine, cysteine, tryptophan, hydroxyproline, aminohexanoic acid, 3-azetidine-carboxylic acid (Az), and 1-(amino)cyclohexanecarboxylic acid (Cy).

Suitably, the arginine-rich arm domains consist of amino acid residues selected from the group consisting of: arginine, beta-alanine and aminohexanoic acid.

The use of non-natural amino acid residues such as beta-alanine or aminohexanoic acid is advantageous in that it helps minimise the immunogenicity of the peptide and also helps to improve the biostability, particularly to metabolism by protease enzymes.

Suitable non-natural amino acids that may be used in the arginine rich arm domains of the present invention are: beta-alanine (B), aminohexanoic acid (X), 3-azetidine-carboxylic acid (Az), and 1-(amino)cyclohexanecarboxylic acid (Cy).

Suitably, the arginine-rich arm domains are formed of amino acid units selected from: R, RR, RJR, RRJ, JRR in any combination or order. Wherein J represents any non-natural amino acid.

Suitably, the arginine-rich arm domains are formed of amino acid units selected from: R, RR, RBR, RXR, XXR, XRR, RRX, BXR, RXB, XRB, RBB, BRB, BBR, RRB, BRR, and BRX in any combination or order. Suitably, an arginine-rich arm domain may consist of one of these units, or a multiple of these units.

Suitably, the arginine-rich arm domains are formed of amino acid units selected from: RRRRRRR (SEQ ID NO.136), RJRRRRR (SEQ ID NO.137), RRJRRRR (SEQ ID NO.138), RRRJRRR (SEQ ID NO.139), RRRRJRR (SEQ ID NO.140), RRRRRJR (SEQ ID NO.141), RJRRJ [RRR]n (SEQ ID NOs.142, 176, 177, 178, 179), RRJRRJ [RR]n (SEQ ID NOs.143, 180, 181, 182, 183), RRRJRRJR (SEQ ID NOs.144), RJRRRJ[RR]n (SEQ ID NOs.145, 184, 185, 186, 187), RJ[RRRR]nJR (SEQ ID NOs.146, 188, 189, 190, 191);

Wherein J represents any non-natural amino acid and wherein n represents an integer from 1-5.

Suitably, wherein n represents an integer from 1-3, suitably wherein n represents, 1, 2 or 3.

Suitably, each arginine-rich arm domain is selected from one of the following sequences: RXRRBRRXR (SEQ ID NO.81), RXRBRXR (SEQ ID NO.82), RXRRBRR (SEQ ID NO.83), RBRXR (SEQ ID NO.84), RBRRBRRBR (SEQ ID NO.85), RBRBRBR (SEQ ID NO.86), RGRRGRRGR (SEQ ID NO.87), RGRGRGR (SEQ ID NO.88), RPRRPRRPR (SEQ ID NO.89), RPRPRPR (SEQ ID NO.90), RHypRRHypRRHypR (SEQ ID NO.91), RHypRHypRHypR (SEQ ID NO.92), RARRARRAR (SEQ ID NO.93), RARARAR (SEQ ID NO.94), RCy*RRCy*RRCy*R (SEQ ID NO.95), RCy*RCy*RCy*R (SEQ ID NO.96), RRBRRBR (SEQ ID NO.97), RBRRBR (SEQ ID NO.98, RRBR (SEQ ID NO.99), RBR, R, RBRBR (SEQ ID NO.100), RBRBRR (SEQ ID NO.101), RBRRR (SEQ ID NO.102), RRRR (SEQ ID NO.103), RBRRBRRR (SEQ ID NO.104), RBRRRRR (SEQ ID NO.105), RRRRRR (SEQ ID NO.106), RRBRR (SEQ ID NO.107), RGRR (SEQ ID NO.108), GRRGR (SEQ ID NO.109), RGGRBRGGR (SEQ ID NO.110), RXRRBRRXRRXRBRXR (SEQ ID NO.113), RXRR (SEQ ID NO.114, RRXR (SEQ ID NO.115), RXR, RRBRBRXR (SEQ ID NO.117), RRBRRBRBRXR (SEQ ID NO.118), RXRRBRRBR (SEQ ID NO.119), RXRRBRRBRBR (SEQ ID NO.120), RXRRBR (SEQ ID NO.121), RXRBRR (SEQ ID NO.122), HXHRBRRXR (SEQ ID NO.123), RXHBHXR (SEQ ID NO.124), RR, RXRXR (SEQ ID NO.125), BRBRBR (SEQ ID NO.127), BRKBRKRBBR (SEQ ID NO.128), BRKBRKRBBRK (SEQ ID NO.129), RAzRRAzRR (SEQ ID NO.130), RAzRAzR (SEQ ID NO.131), and RXRBR (SEQ ID NO.132).

Suitably, each arginine-rich arm domain is selected from one of the following sequences: RXRRBRRXR (SEQ ID NO.81), RXRBRXR (SEQ ID NO.82), RXRRBRR (SEQ ID NO.83), RBRXR (SEQ ID NO.84), RBRBR (SEQ ID NO.100), RBRRBR (SEQ ID NO.98), RXRBR (SEQ ID NO.132), and RXRXR (SEQ ID NO.125).

Optionally, the amino acid residues of the arginine-rich arm domains may also be glycosylated. Details regarding glycosylation may be found in the section describing the glycosylated amino acid residue.

Suitably, each of the arginine-rich arm domains comprised in the peptide is of similar length. For example, the length of each arginine-rich arm domain may differ from one another by no more than 1, 2, or 3 amino acid residues. In a suitable embodiment each arginine-rich arm domain present in a peptide of the invention may be of equal length to one another.

Suitably, each of the arginine-rich arm domains comprised in the peptide has the same sequence.

Suitably, the peptide comprises up to 4 arginine-rich arm domains, 3 arginine-rich arm domains, or 2 arginine-rich arm domains.

In one embodiment, the peptide comprises 2 arginine-rich arm domains.

Suitably, each of the arginine-rich arm domains comprised in the peptide is separated by a directly glycosylated amino acid residue, optionally together with a hydrophobic core domain.

In one embodiment, the peptide comprises two arginine-rich arm domains flanking one central directly glycosylated amino acid residue.

In one embodiment, the peptide comprises two arginine-rich arm domains flanking one central directly glycosylated amino acid residue contiguous with a hydrophobic core domain.

Suitably, the peptide comprises a first arginine-rich arm domain selected from the following sequences: RXRRBRRXR (SEQ ID NO.81), RXRRBRR (SEQ ID NO.83), RBRBR (SEQ ID NO.100), and RXRXR (SEQ ID NO.125).

Suitably, the peptide comprises a second arginine-rich arm domain selected from the following sequences: RXRBRXR (SEQ ID NO.82), RBRXR (SEQ ID NO.84), RBRRBR (SEQ ID NO.98), RXRBR (SEQ ID NO.132), RBRBR (SEQ ID NO.100), and RXRXR (SEQ ID NO.125).

In one embodiment, the peptide comprises a first arginine-rich arm domain consisting of the sequence RXRRBRRXR (SEQ ID NO.81) and a second arginine-rich arm domain consisting of the sequence RXRBRXR (SEQ ID NO.82).

In one embodiment, the peptide comprises a first arginine-rich arm domain consisting of the sequence RXRRBRR (SEQ ID NO.83) and a second arginine-rich arm domain consisting of the sequence RBRXR (SEQ ID NO.84).

In one embodiment, the peptide comprises a first arginine-rich arm domain consisting of the sequence RXRRBRR (SEQ ID NO.83) and a second arginine-rich arm domain consisting of the sequence RXRBR (SEQ ID NO.132).

In one embodiment, the peptide comprises a first arginine-rich arm domain consisting of the sequence RBRBR (SEQ ID NO.100) and a second arginine-rich arm domain consisting of the sequence RBRBR (SEQ ID NO.100).

In one embodiment, the peptide comprises a first arginine-rich arm domain consisting of the sequence RXRXR (SEQ ID NO.125) and a second arginine-rich arm domain consisting of the sequence RXRXR (SEQ ID NO.125).

Hydrophobic Core Domains

The present invention defines a peptide comprising at least one directly glycosylated amino acid residue and one or more arginine-rich arm domains.

The peptide may further comprise one or more hydrophobic core domains.

By 'hydrophobic' it is meant that a core domain, when taken as a whole, has an overall hydrophobic nature. This may be determined by, for example, hydropathy plot, such as a Kyte-Doolittle hydropathy plot (in which case the hydrophobicity of the core domain will be indicated by an overall positive score). Suitably, a core domain may comprise a majority of hydrophobic amino acid residues.

Suitably the hydrophobic core domains each comprise between 1-4 hydrophobic amino acid residues.

In one embodiment, the hydrophobic core domains each comprise between 1-2 hydrophobic amino acid residues.

Suitable hydrophobic amino acid residues that may be incorporated in the core domains are, for example; glycine, alanine, valine, leucine, isoleucine, proline, phenylalanine, methionine, and tryptophan, or amino acid analogues thereof.

Suitably the hydrophobic amino acid residues of the core domains are selected from phenylalanine or leucine.

Suitably each hydrophobic core domain comprises a total of between 1-6 amino acid residues, suitably 1-5 amino acid residues, suitably 1-4 amino acid residues, suitably 1-3 amino acid residues.

In one embodiment, each hydrophobic core domain comprises a total of between 1-2 amino add residues.

The other amino add residues present in each hydrophobic core domain in addition to the hydrophobic amino acid residues may be any other amino acid, for example; arginine, asparagine, aspartic add, cysteine, glutamic acid, glutamine, glycine, histidine, lysine, serine, threonine, tyrosine, or any amino acid analogues thereof.

Suitably, the other amino acids residues present in each core domain are selected from tyrosine and glutamine.

Optionally the hydrophobic core domain may include one or more non-natural amino acids such as aminohexanoic acid or 3-Alanine or tetrahydroisoquinoline-3-carboxylic acid (TIC) as listed above.

Suitably, the hydrophobic core domain may comprise one of the following sequences: ZAA, ZA, Z, AZA, AZ, ZAZ, ZZA and ZZZ;

Wherein Z represents 1,2,3,4-tetrahydroisoquinoline-3-carboxylic acid (TIC) residue.

Wherein A represents a hydrophobic amino acid residue as defined above.

Suitably the peptide comprises up to 4 hydrophobic core domains. Suitably the peptide comprises 3 hydrophobic core domains, suitably 2 hydrophobic core domains, or suitably only a single hydrophobic core domain.

In one embodiment, the peptide comprises only 1 hydrophobic core domain.

Suitably the hydrophobic core domains are contiguous with the at least one directly glycosylated amino acid residue. Suitably the hydrophobic core domains may be on the C-terminal or N-terminal side of the at least one directly glycosylated amino acid residue.

In one embodiment, the hydrophobic core domains are on the C-terminal side of the at least one directly glycosylated amino acid residue.

Suitably the hydrophobic core domains contiguous with at least one directly glycosylated amino acid residue may be positioned anywhere within the peptide.

In a suitable embodiment a hydrophobic core domain contiguous with at least one directly glycosylated amino acid residue is positioned in the peptide such that the directly glycosylated amino acid residue is contiguous with an arginine-rich arm domain.

Suitably, the hydrophobic core domains contiguous with the directly glycosylated amino acid residue are positioned between two flanking arm domains.

Suitably at least one of the hydrophobic core domains contiguous with a directly glycosylated amino acid residue is positioned at the centre of the peptide.

In one embodiment, the peptide comprises one hydrophobic core domain contiguous with a directly glycosylated amino acid residue positioned at the centre of the peptide between two flanking arm domains.

Suitably the hydrophobic core domains are selected from one of the following sequences: GFTGPL (SEQ ID NO.133), QFL, Z, ZL, F, FL, FQILY (SEQ ID NO.134), FQ, WF, QF, FQ, and YQFLI (SEQ ID NO.135). Suitably, the core domains are selected from one of the following sequences Z, F and FL.

In one embodiment, the peptide comprises one core domain wherein the core domain consists of the sequence F.

In one embodiment, the peptide comprises one core domain wherein the core domain consists of the sequence FL.

In one embodiment, the peptide comprises one core domain wherein the core domain consists of the sequence Z.

Peptide Structure

The present invention defines a peptide comprising at least one directly glycosylated amino acid residue and one or more arginine-rich arm domains, optionally in combination with at least one hydrophobic core domain.

Suitably, the peptides have a sequence that is a contiguous single molecule. Suitably, the peptide comprises several domains and at least one directly glycosylated amino acid residue in a linear arrangement between the N-terminus and the C-terminus. Suitably, the domains are selected from arginine rich arm domains and optional hydrophobic core domains described above.

Suitably, the peptide sequence is comprised of amino acid residues and optional non-natural amino acid residues, or amino acid analogues as defined hereinabove. Accordingly in some case, the peptide may comprise non-peptide bonds. The relevant amino acid residues comprised in the at least one directly glycosylated residue and for the domains of the peptide are described in each section above.

Each domain and the at least one directly glycosylated amino acid residue have common sequence characteristics as described in the sections above, but the exact sequence of each domain is capable of variation and modification. Thus a range of sequences is possible for each domain. The combination of each possible domain sequence and the options for the or each directly glycosylated amino acid residue yields a range of peptide structures, each of which form part of the present invention. Features of the peptide structures are described below.

Suitably, the directly glycosylated amino acid residues separate each arginine-rich arm domain. Suitably, each directly glycosylated amino acid residue is flanked by arginine-rich arm domains on either side thereof.

Suitably no arginine-rich arm domain is contiguous with another arginine-rich arm domain.

In one embodiment, the peptide comprises three directly glycosylated amino acid residues separated by arginine-rich arm domains and flanked on either side by two further arginine-rich arm domains in the following arrangement:

[arginine-rich arm domain]-[aa*]-[arginine-rich arm domain]-[aa*]-[arginine-rich arm domain]-[aa*]-[arginine-rich arm domain]

In one embodiment, the peptide comprises two directly glycosylated amino acid residues separated by one arginine-rich arm domain and flanked on either side by two further arginine-rich arm domains in the following arrangement:

[arginine-rich arm domain]-[aa*]-[arginine-rich arm domain]-[aa*]-[arginine-rich arm domain]

In one embodiment, the peptide comprises one directly glycosylated amino acid residue flanked by two arginine-rich arm domains in the following arrangement:

[arginine-rich arm domain]-[aa*]-[arginine-rich arm domain]

Optionally, more than one contiguous directly glycosylated amino acid residue may be present in the peptide.

Therefore, in one embodiment, the peptide may comprise three contiguous directly glycosylated amino acid residues flanked by two arginine-rich arm domains in the following arrangement:

[arginine-rich arm domain]-[aa*]-[aa*]-[aa*]-[arginine-rich arm domain]

Therefore, in one embodiment, the peptide may comprise two contiguous directly glycosylated amino acid residues flanked by two arginine-rich arm domains in the following arrangement:

[arginine-rich arm domain]-[aa*]-[aa*]-[arginine-rich arm domain]

Optionally, the directly glycosylated amino acid residues may be present in combination with a hydrophobic core domain. If present, suitably the directly glycosylated amino acid residues are contiguous with the hydrophobic core domain. The hydrophobic core domain may be present on the C-terminal or the N-terminal side of the directly glycosylated amino acid residue.

Therefore in one embodiment, the peptide may comprise one directly glycosylated amino acid residue contiguous with one hydrophobic core domain flanked by two arginine-rich arm domains in the following arrangement:

[arginine-rich arm domain]-[aa*]-[hydrophobic core domain]-[arginine-rich arm domain]

In one embodiment, the peptide may comprise two directly glycosylated amino acid residues each contiguous with one hydrophobic core domain separated by one arginine-rich arm domain and flanked on either side by two further arginine-rich arm domains in the following arrangement:

[arginine-rich arm domain]-[aa*]-[hydrophobic core domain]-[arginine-rich arm domain]-[aa*]-[hydrophobic core domain]-[arginine-rich arm domain]

In one embodiment, the peptide may comprise three directly glycosylated amino acid residues each contiguous with one hydrophobic core domain separated by arginine-rich arm domains and flanked on either side by two further arginine-rich arm domains in the following arrangement:

[arginine-rich arm domain]-[aa*]-[hydrophobic core domain]-[arginine-rich arm domain]-[aa*]-[hydrophobic core domain]-[arginine-rich arm domain]-[aa*]-[hydrophobic core domain]-[arginine-rich arm domain]

Suitably, any combination of the above peptide structures is envisaged by the present invention. Each directly glycosylated amino acid residue may be present with or without a contiguous hydrophobic core domain. Multiple contiguous directly glycosylated amino acid residues may be present.

Suitably, the peptide may comprise a first directly glycosylated amino acid residue without a contiguous hydrophobic core domain and a second directly glycosylated amino acid residue contiguous with a hydrophobic core domain, for example.

Therefore, in one embodiment, the peptide may comprise two directly glycosylated amino acid residues, the first without a hydrophobic core domain and the second contiguous with a hydrophobic core domain, each separated by an arginine-rich arm domain and flanked on either side by two further arginine-rich arm domains in the following arrangement:

[arginine-rich arm domain]-[aa*]-[arginine-rich arm domain]-[aa*]-[hydrophobic core domain]-[arginine-rich arm domain]

Therefore, in one embodiment, the peptide may comprise two directly glycosylated amino acid residues, the first contiguous with a hydrophobic core domain and the second without a hydrophobic core domain, each separated by an arginine-rich arm domain and flanked on either side by two further arginine-rich arm domains in the following arrangement:

[arginine-rich arm domain]-[aa*]-[hydrophobic core domain]-[arginine-rich arm domain]-[aa*]-[arginine-rich arm domain]

Therefore, in one embodiment, the peptide may comprise three directly glycosylated amino acid residues, the first and third without a hydrophobic core domain, and the second contiguous with a hydrophobic core domain, each separated by an arginine-rich arm domain and flanked on either side by two further arginine-rich arm domains in the following arrangement:

[arginine-rich arm domain]-[aa*]-[arginine-rich arm domain]-[aa*]-[hydrophobic core domain]-[arginine-rich arm domain]-[aa*]-[arginine-rich arm domain]

Suitably, the peptide is N-terminal modified.

Suitably the peptide is N-acetylated, N-methylated, N-trifluoroacetylated, N-trifluoromethylsulfonylated, or N-methylsulfonylated.

Optionally, the N-terminus of the peptide may be unmodified.

Suitably, the peptide is C-terminal modified.

Suitably, the peptide comprises a C-terminal modification selected from: Carboxy-, Thioacide-, Aminooxy-, Hydrazino-, thioester-, azide, strained alkyne, strained alkene, aldehyde-, thiol or haloacetyl-group.

Advantageously, the C-terminal modification provides a means for linkage of the peptide to the therapeutic molecule.

Accordingly, the C-terminal modification may comprise the linker and vice versa. Suitably, the C-terminal modification may consist of the linker or vice versa. Suitable linkers are described herein elsewhere.

Suitably, the peptide comprises a C-terminal carboxyl group.

Suitably, the C-terminal carboxyl group may be a provided by a glycine, aminohexanoic acid, β-alanine, alanine, glutamic acid side chain or aspartic acid side chain.

Suitably, the C-terminal carboxyl group is provided by a glycine or β-alanine residue.

In one embodiment, the C terminal carboxyl group is provided by a glycine residue.

In one embodiment, the C terminal carboxyl group is provided by a β-alanine residue.

In one embodiment, the C-terminal modification comprises a glycine residue and/or a β-alanine residue.

In one embodiment, the C-terminal modification is a glycine residue.

In one embodiment, the C-terminal modification is a β-alanine residue.

Alternatively, the peptide may be linked to the therapeutic molecule through an N-terminal modification of the peptide.

Suitably, in such embodiments, the peptide comprises an N-terminal modification selected from: succinic acid, a side-chain of aspartic acid or a side chain of glutamic acid.

Suitably, in such embodiments, the C-terminus of the peptide is present as an amide.

The peptide of the present invention is defined as having a total length of 40 amino acid residues or less. The peptide may therefore be regarded as an oligopeptide.

Suitably, the peptide comprises a total length of between 3-30 amino acid residues, suitably of between 5-25 amino acid residues, of between 10-25 amino acid residues, of between 13-23 amino acid residues, of between 15-21 amino acid residues.

Suitably the peptide is capable of penetrating cells. The peptide may therefore be regarded as a cell penetrating peptide.

Suitably, the peptide is for attachment to a therapeutic molecule. Suitably, the peptide is for transporting a therapeutic molecule into a target cell. Suitably, the peptide is for delivering a therapeutic molecule into a target cell. The peptide may therefore be regarded as a carrier peptide.

Suitably, the peptide may be selected from any of the following sequences:

(SEQ ID NO. 8)
RXRRBRRXRQFLRXRBRXRS*

(SEQ ID NO. 9)
RXRRBRRXRQFLRXRS*RXR (SEQ ID NO. 10)
RXRRS*RRXRQFLRXRBRXR (SEQ ID NO. 11)
S*RXRRBRRXR QFL RXRBRXR (SEQ ID NO. 12)
RXRRBRRXR S*QFLS*RXRBRXR (SEQ ID NO. 13)
RXRRBRRXRS*QFLRXRBRXR (SEQ ID NO. 14)
RXRRBRRXRS*FLRXRBRXR (SEQ ID NO. 15)
$(S*BRKBRKRBBR)_2K$ (SEQ ID NO. 16)
$(GFTGPLS*BRKBRKRBBR)_2K$ (SEQ ID NO. 17)
RXRRBRRFS*RBRXR (SEQ ID NO. 18)
RBRRBRRBRS*FLRBRBRBR (SEQ ID NO. 19)
RGRRGRRGRS*FLRGRGRGR (SEQ ID NO. 20)
RPRRPRRPRS*FLRPRPRPR (SEQ ID NO. 21)
RHypRRHypRRHypRS*FLRHypRHypRHypR

-continued (SEQ ID NO. 22)
RARRARRARS*FLRARARAR (SEQ ID NO. 23)
RCyRRCyRRCyRS*FLRCyRCyRCyR (SEQ ID NO. 24)
RRBRRBRS*FLRBRBRBR (SEQ ID NO. 25)
RBRRBRS*FLRBRBRBR (SEQ ID NO. 26)
RRBRS*FLRBRBRBR (SEQ ID NO. 27)
RBRS*FLRBRBRBR (SEQ ID NO. 28)
RS*FLRBRBRBR (SEQ ID NO. 29)
RBRRBRRBRS*FLRBRBR (SEQ ID NO. 30)
RBRRBRRBRS*FLRBR (SEQ ID NO. 31)
RBRRBRRBRS*FLR (SEQ ID NO. 32)
RBRRBRRBRS*FL (SEQ ID NO. 33)
RBRRBRRBRS*FLRBRBRR (SEQ ID NO. 34)
RBRRBRRBRS*FLRBRRR (SEQ ID NO. 35)
RBRRBRRBRS*FLRRRR (SEQ ID NO. 36)
RBRRBRRRS*FLRBRBRBR (SEQ ID NO. 37)
RBRRRRRS*FLRBRBRBR (SEQ ID NO. 38)
RRRRRRS*FLRBRBRBR (SEQ ID NO. 39)
RBRRBRRRS*FLRRBRR (SEQ ID NO. 40)
RBRRRRRS*FLRRRR (SEQ ID NO. 41)
RRRRRRS*FLRRRR (SEQ ID NO. 42)
RGRR S*GRRGRS*FLRGGRBRGGR (SEQ ID NO. 43)
RXRRBRRXRS*FRXRBRXR (SEQ ID NO. 44)
RXRRBRRXRS*RXRBRXR (SEQ ID NO. 45)
RXRRBRRS*FQILYRBRXR (SEQ ID NO. 46)
RXRRBRRS*FLRBRXR (SEQ ID NO. 47)
RXRRBRRXRS*FLRXRBRXRS*FL (SEQ ID NO. 48)
RXRRBRRXRRXRBRXRS*FL -continued (SEQ ID NO. 49)
RXRRS*RRXRS*FLRXRS*RXR (SEQ ID NO. 50)
RXRRBRRXRS*FQRXRBRXR (SEQ ID NO. 52)
RXRRBRRXRS*WFRXRBRXR (SEQ ID NO. 53)
RXRRBRRXRS*QFRXRBRXR (SEQ ID NO. 54)
RXRRBRRXRS*FQRXRBS*YQFLIRXR (SEQ ID NO. 55)
RXRRBRRS*RBRXR (SEQ ID NO. 56)
RXRRFS*RRBRBRXR (SEQ ID NO. 57)
R FS*RRBRRBRBRXR (SEQ ID NO. 58)
RXRRS*RRBRBRXR (SEQ ID NO. 59)
RS*RRBRRBRBRXR (SEQ ID NO. 60)
RXRRBRRBRS*RXR (SEQ ID NO. 61)
RXRRBRRBRBRS*R (SEQ ID NO. 62)
RXRRBRFS*RBR (SEQ ID NO. 63)
RXRRBRS*RBR (SEQ ID NO. 64)
RXRBRRS*RBR (SEQ ID NO. 65)
RRBRRS*RBR (SEQ ID NO. 66)
HXHRBRRXRS*RXHBHXR (SEQ ID NO. 67)
RXRRBRRS*S*RBRXR (SEQ ID NO. 68)
RXRRBRRS*S*S*RBRXR (SEQ ID NO. 69)
RXRRS*RR S*RS*RXR (SEQ ID NO. 70)
RBRBRS*RBRBR (SEQ ID NO. 71)
RXRXRS*RXRXR (SEQ ID NO. 72)
RXRRBS*BRBRBR (SEQ ID NO. 73)
RXRRBRRZS* RBRXR (SEQ ID NO. 74)
RXRRBRRFS$^1$*RBRXR (SEQ ID NO. 75)
RXRRBRRFS$^2$* RBRXR (SEQ ID NO. 76)
RXRRBRRFS$^3$* RBRXR -continued (SEQ ID NO. 77)
RXRRBRRFS$^4$* RBRXR (SEQ ID NO. 78)
RXRRBRRFN* RBRXR (SEQ ID NO. 79)
RXRRBRRFS$^6$* RBRXR (SEQ ID NO. 80)
RAzRRAzRRZS*RAzRAzR Suitably the peptide is selected from the following sequences: RXRRBRRXRS*FLRXRBRXR (SEQ ID NO.14), RXRRBRRFS*RBRXR (SEQ ID NO.17), RXRRBRRZS*RBRXR (SEQ ID NO.73), RXRRBRRFS$^1$*RBRXR (SEQ ID NO.74), RBRBRS*RBRBR (SEQ ID NO.70) and RXRXRS*RXRXR (SEQ ID NO.71).

Wherein Z represents 1,2,3,4-tetrahydroisoquinoline-3-carboxylic acid.

Wherein S* represents L-serine glycosylated with D-Glucose sugar.

Wherein S$^1$* represents D-serine glycosylated with D-Glucose sugar.

Wherein S$^2$* represents L-serine glycosylated with an L-Glucose sugar.

Wherein S$^3$* represents L-serine glycosylated with a D-Mannose sugar.

Wherein S$^4$* represents L-serine glycosylated with a D-Lactose sugar.

Wherein N* represents L-asparagine glycosylated with a D-2-Acetylamino Glucose sugar.

Wherein S$^6$* represents L-serine glycosylated with a Galactose sugar.

In one embodiment, the peptide is
(SEQ ID NO. 14)
RXRRBRRXRS*FLRXRBRXR.

In one embodiment, the peptide is
(SEQ ID NO. 17)
RXRRBRRFS*RBRXR.

In one embodiment, the peptide is
(SEQ ID NO. 73)
RXRRBRRZS*RBRXR.

In one embodiment, the peptide is
(SEQ ID NO. 74)
RXRRBRRFS$^1$*RBRXR.

In one embodiment, the peptide is
(SEQ ID NO. 70)
RBRBRS*RBRBR.

In one embodiment, the peptide is
(SEQ ID NO. 71)
RXRXRS*RXRXR.

Suitably the peptide is capable of penetrating into cells and tissues, suitably into the nucleus of cells. Suitably into muscle tissues.

Suitably the peptide is capable of penetrating into cells of the central nervous system.

Suitably the peptide is capable of crossing the blood brain barrier, suitably into many compartments of the central nervous system.

Suitably the peptide is capable of crossing the blood brain barrier, suitably into the cortex, brainstem, cerebellum, cervical, thoracic, and lumber compartments of the central nervous system.

Optionally, the peptide may further be selected from any of the following sequences:

(SEQ ID NO. 116)
RXRRBRRZS* RXRBR (SEQ ID NO. 51)
RXRRBRRFS$^1$* RXRBR (SEQ ID NO. 111)
RXRRBRRFS$^2$* RXRBR (SEQ ID NO. 112)
RXRRBRRFS$^3$* RXRBR (SEQ ID NO. 157)
RXRRBRRFS$^4$* RXRBR (SEQ ID NO. 126)
RXRRBRRFN* RXRBR (SEQ ID NO. 158)
RXRRBRRFS$^6$* RXRBR (SEQ ID NO. 159)
RXRRBRRFS$^5$* RBRXR (SEQ ID NO. 160)
RXRRBRRF S$^5$* RXRBR (SEQ ID NO. 161)
RBRBRS*RBRRBR (SEQ ID NO. 162)
RXRRBRRS$^1$*RBRXR (SEQ ID NO. 163)
RXRRBRRS$^2$* RBRXR (SEQ ID NO. 164)
RXRRBRRS$^3$* RBRXR (SEQ ID NO. 165)
RXRRBRRS$^4$* RBRXR (SEQ ID NO. 166)
RXRRBRRN* RBRXR (SEQ ID NO. 167)
RXRRBRRS$^6$* RBRXR (SEQ ID NO. 168)
RXRRBRRS$^1$* RXRBR (SEQ ID NO. 169)
RXRRBRRS$^2$* RXRBR (SEQ ID NO. 170)
RXRRBRRS$^3$* RXRBR (SEQ ID NO. 171)
RXRRBRRS$^4$* RXRBR (SEQ ID NO. 172)
RXRRBRRN* RXRBR (SEQ ID NO. 173)
RXRRBRRS$^6$* RXRBR (SEQ ID NO. 174)
RXRRBRRS$^6$* RBRXR (SEQ ID NO. 175)
RXRRBRRS$^6$* RXRBR

Wherein S$^5$* represents L-serine glycosylated with a D-2-Acetylamino Glucose sugar.

Conjugates

The peptide of the invention may be covalently linked to a therapeutic molecule in order to provide a conjugate.

The therapeutic molecule may be any molecule for treatment of a disease, suitably any small molecule. The therapeutic molecule may be selected from: a nucleic acid, peptide nucleic acid, antisense oligonucleotide (such as PNA, PMO), short interfering RNA, micro RNA, peptide, cyclic peptide, protein, pharmaceutical or drug.

In one embodiment, the therapeutic molecule is an antisense oligonucleotide.

Suitably the antisense oligonucleotide is comprised of a phosphorodiamidate morpholino oligonucleotide (PMO).

Alternatively the oligonucleotide may be a modified PMO or any other charge-neutral oligonucleotide such as a peptide nucleic acid (PNA), a chemically modified PNA such as a gamma-PNA (Bahal, Nat. Comm. 2016), oligonucleotide phosphoramidate (where the non-bridging oxygen of the phosphate is substituted by an amine or alkylamine such as those described in WO2016028187A1, or any other partially or fully charge-neutralized oligonucleotide.

The therapeutic antisense oligonucleotide sequence may be selected from any that are available, for example antisense oligonucleotides for exon skipping in DMD are described in Yin, Mol. Ther. 2011; and Betts, MTNA, 2012).

In one embodiment, the therapeutic antisense oligonucleotide is complementary to the ISSN1 or IN7 sequence, suitable antisense oligonucleotides are described in Zhou, H G T, 2013; and Hammond et al, 2016; and Osman et al, HMG, 2014.

PMO oligonucleotides of any sequence may be purchased (for example from Gene Tools Inc, USA).

In one embodiment, the therapeutic molecule of the conjugate is an oligonucleotide complementary to the pre-mRNA of a gene target.

Suitably, the oligonucleotide complementary to the pre-mRNA of a gene target gives rise to a steric blocking event that alters the pre-mRNA leading to an altered mRNA and hence a protein of altered sequence.

Suitably the steric blocking event may be exon inclusion (or exon skipping).

Optionally, lysine residues may be added to one or both ends of a therapeutic molecule (such as a PMO or PNA) before attachment to the peptide to improve water solubility.

Suitably the therapeutic molecule has a molecular weight of less than 5,000 Da, suitably less than 3000 Da or suitably less than 1000 Da.

Suitably, the peptide is covalently linked to the therapeutic molecule at the C-terminus, but it alternatively may be linked at the N-terminus as described above.

Suitably, the peptide is covalently linked to the therapeutic molecule through a linker if required. The linker may act as a spacer to separate the peptide sequence from the therapeutic molecule.

The linker may be selected from any suitable sequence.

Suitably, the linker may be part of the peptide or the therapeutic molecule.

Suitable linkers include, for example, a C-terminal cysteine residue that permits formation of a disulphide, thioether or thiol-maleimide linkage, a C-terminal aldehyde to form an oxime, a click reaction or formation of a morpholino linkage with a basic amino acid on the peptide or a carboxylic acid moiety on the peptide covalently conjugated to an amino group to form a carboxamide linkage.

Suitably, the linker is between 1-5 amino acids in length.

Suitably the linker is selected from any of the following sequences: BC, XC, C, GGC, BBC, BXC, XBC, X, XX, B, BB, BX and XB.

Any B or X may be replaced by another amino acid, such as Gly, Ala or Pro or the side-chain of Glu or Asp, or any non-natural amino acid residue, for example, 4-aminobutyryl (Aib) or isonicopecotinyl.

In one embodiment, the linker is 3-alanine or glycine.

In one embodiment, the peptide is conjugated to the therapeutic molecule through a carboxamide linkage.

The linker of the conjugate may form part of the therapeutic molecule to which the peptide is attached. Alternatively, the attachment of the therapeutic molecule may be directly linked to the C-terminus of the peptide. Suitably, in such embodiments, no linker is required.

Alternatively, the peptide may be chemically conjugated to the therapeutic molecule. Chemical linkage may be via a disulphide, alkenyl, alkynyl, aryl, ether, thioether, triazole, amide, carboxamide, urea, thiourea, semicarbazide, carbazide, hydrazine, oxime, phosphate, phosphoramidate, thiophosphate, boranophosphate, iminophosphates, or thiol-maleimide linkage, for example.

Optionally, cysteine may be added at the N-terminus of a therapeutic molecule to allow for disulphide bond formation to the peptide, or the N-terminus may undergo bromoacetylation for thioether conjugation to the peptide.

Suitably the conjugate is capable of penetrating into cells and tissues, suitably into the nucleus of cells. Suitably into muscle tissues.

Suitably the conjugate is capable of penetrating into cells of the central nervous system.

Suitably the conjugate is capable of crossing the blood brain barrier, suitably into many compartments of the central nervous system.

Suitably the conjugate is capable of crossing the blood brain barrier, suitably into the cortex, brainstem, cerebellum, cervical, thoracic, and lumber compartments of the central nervous system.

Pharmaceutical Composition

The conjugate of the invention may formulated into a pharmaceutical composition.

Suitably, the pharmaceutical composition may further comprise a pharmaceutically acceptable diluent, adjuvant or carrier.

Suitable pharmaceutically acceptable diluents, adjuvants and carriers are well known in the art.

As used herein, the phrase "pharmaceutically acceptable" refers to those ligands, materials, formulations, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier", as used herein, refers to a pharmaceutically acceptable material, formulation or vehicle, such as a liquid or solid filler, diluent, excipient, solvent or encapsulating material, involved in carrying or transporting the conjugate from one organ or portion of the body, to another organ or portion of the body. Each carrier must be "acceptable" in the sense of being compatible with the other components of the composition e.g. the peptide and therapeutic molecule, and not injurious to the individual. Lyophilized compositions, which may be reconstituted and administered, are also within the scope of the present composition.

Pharmaceutically acceptable carriers may be, for example, excipients, vehicles, diluents, and combinations thereof. For example, where the compositions are to be administered orally, they may be formulated as tablets, capsules, granules, powders, or syrups; or for parenteral administration, they may be formulated as injections (intramuscular, subcutaneous, intramedullary, intrathecal, intraventricular, intravenous, intravitreal), drop infusion preparations, or suppositories. These compositions can be prepared by conventional means, and, if desired, the active compound (i.e. conjugate) may be mixed with any conventional additive, such as an excipient, a binder, a disintegrating agent, a lubricant, a corrigent, a solubilizing agent, a suspension aid, an emulsifying agent, a coating agent, or combinations thereof.

It should be understood that the pharmaceutical compositions of the present disclosure can further include additional known therapeutic agents, drugs, modifications of compounds into prodrugs, and the like for alleviating, mediating, preventing, and treating the diseases, disorders, and conditions described herein under medical use.

Medical Use

The conjugate comprising the peptide of the invention may be used as a medicament for the treatment of a disease.

The medicament may be in the form of a pharmaceutical composition as defined above.

A method of treatment of a patient or subject in need of treatment for a disease condition is also provided, the method comprising the step of administering a therapeutically effective amount of the conjugate to the patient or subject.

Suitably, the medical treatment requires delivery of the therapeutic molecule into a cell, suitably into the nucleus of the cell.

Diseases to be treated may include any disease where improved penetration of the cell and/or nuclear membrane by a therapeutic molecule may lead to an improved therapeutic effect.

Suitably, the conjugate is for use in the treatment of diseases of the central nervous system.

Conjugates comprising peptides of the invention are suitable for the treatment of genetic diseases of the central nervous system. In a suitable embodiment, there is provided a conjugate according to the second aspect for use in the treatment of genetic diseases of the central nervous system.

Suitably, the conjugate is for use in the treatment of diseases caused by splicing deficiencies. In such embodiments, the therapeutic molecule may comprise an oligonucleotide capable of preventing or correcting the splicing defect and/or increasing the production of correctly spliced mRNA molecules.

Suitably the conjugate is for use in the treatment of any of the following diseases: Duchenne Muscular Dystrophy (DMD), Bucher Muscular Dystrophy (BMD), Menkes disease, Beta-thalassemia, dementia, Parkinson's Disease, Spinal Muscular Atrophy (SMA), myotonic dystrophy (DM), Huntington's Disease, Hutchinson-Gilford Progeria Syndrome, Ataxia-telangiectasia, or cancer.

In one embodiment, the conjugate is for use in the treatment of SMA.

In one embodiment, there is provided a conjugate according to the second aspect for use in the treatment of SMA.

Suitably, in such an embodiment, the therapeutic molecule of the conjugate is operable to reduce transcription of the truncated form of the SMN2 gene and increase transcription of the full-length form of the SMN2 gene.

Suitably, the therapeutic molecule of the conjugate is operable to do so by increasing inclusion of exon 7 during SMN2 transcription.

Suitably, the therapeutic molecule of the conjugate is operable to increase expression of the SMN2 protein. Suitably the therapeutic molecule of the conjugate increases expression of the SMN2 protein by up to 3 times compared with untreated subjects.

Suitably, the patient or subject to be treated may be any animal or human. Suitably, the patient or subject may be a non-human mammal. Suitably the patient or subject may be male or female.

Suitably, the conjugate is for administration to a subject systemically for example by enteral, parenteral, intravenous, intra-arterial, intramuscular, intratumoural, oral or nasal routes.

In one embodiment, the conjugate is for administration to a subject intravenously.

Suitably, the conjugate is for administration to a subject in a "therapeutically effective amount", by which it is meant that the amount is sufficient to show benefit to the individual. The actual amount administered, and rate and time-course of administration, will depend on the nature and severity of the disease being treated. Decisions on dosage etcetera, are within the responsibility of general practitioners and other medical doctors. Examples of the techniques and protocols can be found in Remington's Pharmaceutical Sciences, 20th Edition, 2000, pub. Lippincott, Williams & Wilkins.

Suitably, the conjugate is for administration to a subject at a dose of between 0.01 mg/kg and 20 mg/kg, 0.05 mg/kg and 19 mg/kg, 0.1 mg/kg and 18 mg/kg, 0.5 mg/kg and 17 mg/kg, 1 mg/kg and 16 mg/kg, 2 mg/kg and 15 mg/kg, 5 mg/kg and 10 mg/kg, 10 mg/kg and 20 mg/kg, 12 mg/kg and 18 mg/kg, 13 mg/kg and 17 mg/kg, for example or any value therebetween.

Nucleic Acids and Hosts

Peptides of the invention may be produced by any standard protein synthesis method, for example chemical synthesis, semi-chemical synthesis or through the use of expression systems.

Accordingly, the present invention also relates to the nucleotide sequences comprising or consisting of the DNA coding for the peptides, expression systems e.g. vectors comprising said sequences accompanied by the necessary sequences for expression and control of expression, and host cells and host organisms transformed by said expression systems.

Accordingly, a nucleic acid encoding a peptide according to the present invention is also provided.

Suitably, the nucleic acids may be provided in isolated or purified form.

An expression vector comprising a nucleic acid encoding a peptide according to the present invention is also provided.

Suitably, the vector is a plasmid.

Suitably the vector comprises a regulatory sequence, e.g. promoter, operably linked to a nucleic acid encoding a peptide according to the present invention. Suitably, the expression vector is capable of expressing the peptide when transfected into a suitable cell, e.g. mammalian, bacterial or fungal cell.

A host cell comprising the expression vector of the invention is also provided.

Expression vectors may be selected depending on the host cell into which the nucleic acids of the invention may be inserted. Such transformation of the host cell involves conventional techniques such as those taught in Sambrook et al [Sambrook, J., Russell, D. (2001) Molecular Cloning: A Laboratory Manual, Cold Spring Harbor Laboratory Press, NY, USA]. Selection of suitable vectors is within the skills of the person knowledgeable in the field. Suitable vectors include plasmids, bacteriophages, cosmids, and viruses.

The peptides produced may be isolated and purified from the host cell by any suitable method e.g. precipitation or chromatographic separation e.g. affinity chromatography.

Suitable vectors, hosts and recombinant techniques are well known in the art.

In this specification the term "operably linked" may include the situation where a selected nucleotide sequence and regulatory nucleotide sequence are covalently linked in such a way as to place the expression of a nucleotide coding sequence under the control of the regulatory sequence, as such, the regulatory sequence is capable of effecting transcription of a nucleotide coding sequence which forms part or all of the selected nucleotide sequence. Where appropriate, the resulting transcript may then be translated into a desired peptide.

BRIEF DESCRIPTION OF THE DRAWINGS

Certain embodiments of the present invention will now be described with reference to the following figures and tables in which.

Figure 1:
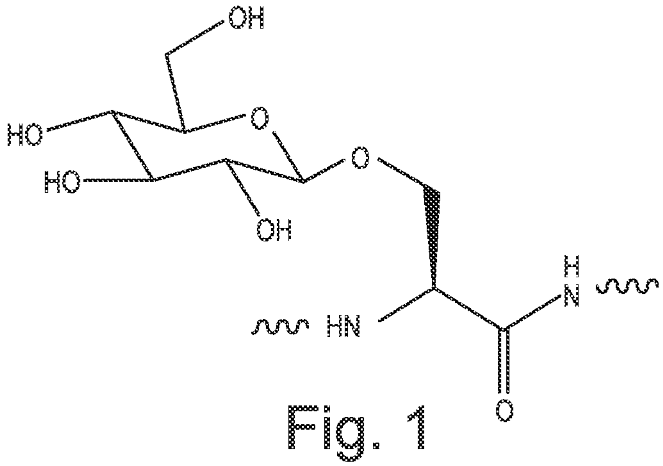
FIG. 1: Shows the structure of Beta D-glucosyl serine residue.

Table 1: Shows the sequences of the peptides tested in vivo incorporating SEQ ID NO.s 1-7 and 14 and 17 with additional N and C terminal modifications, including peptide and SEQ ID NO.s 1-7 of currently available peptides, and peptide and SEQ ID NO.s 14 and 17 of the invention;

Table 2: Shows the sequences of peptides screened in vitro in SMA patient fibroblasts incorporating SEQ ID NO.s 1-80 with additional N and C terminal modifications, including peptide and SEQ ID NO.s 1-7 of currently available peptides, and peptide and SEQ ID NO.s 8-80 of the invention;

Table 3: Shows quantitative PCR data for levels of full-length SMN2 transcripts generated in adult SMA mice treated with doses of 2×15 mg/kg of PMO conjugates with the peptides listed given approximately 48 hours apart. Tissues were harvested 7 days post final administration and RNA collected for qPCR analysis. Data represented as mean expression level (*P≤0.05; P≤0.005; *P≤0.0005; ****P≤0.00005 by Student's t test in comparison to saline treated controls). P values for liver samples all exceeded P≤0.00005 (not represented in table).

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or 27 process so disclosed, may be combined in any combination, except combinations where at least some of such features and/or steps are mutually exclusive.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The reader's attention is directed to all papers and documents which are filed concurrently with or previous to this specification in connection with this application and which are open to public inspection with this specification, and the contents of all such papers and documents are incorporated herein by reference.

EXAMPLES

1. Peptides Comprising a Beta D-Glucosyl Serine Residue.

The present inventors set out to find short peptides that, when conjugated to an oligonucleotide therapeutic, might lead to significant and effective cell penetration and activity in all or most spinal cord and brain compartments.

Surprisingly, the present inventors discovered that inclusion of a directly glycosylated amino acid (for example: S*, FIG. 1) into short arginine rich peptide carriers, and in addition systemic injection into adult SMA mice results in exon inclusion in 6 brain and spinal cord compartments as well in skeletal muscles. This is demonstrated in the present examples with the synthesis of a series of arginine rich peptides having one or more β-D-glucosyl serine residues, and in some cases additional hydrophobic domains.

The present inventors synthesised a series of candidate peptides named the 'D-PEP5' peptides. The first of which, peptide 14 (Table 1 and 2), comprises 10-Arg flanking arm domain sequences and an S* residue adjacent to a shortened 2-amino acid hydrophobic core of FL, and the second of which, peptide 17, comprises flanking 8-Arg arm domain sequences but has an S* residue adjacent to a single amino acid hydrophobic core of F (Table 1 and 2). A variety of currently available peptides were also synthesised for comparison with the inventive D-PEP5 peptides. These are numbered as peptides 1-7 in table 1 and incorporate the following peptide sequences:

(SEQ ID NO. 1)
RXRRBRRXRYQFLIRXRBRXR (SEQ ID NO. 2)
RXRRBRRXRQFLRXRBRXR (SEQ ID NO. 3)
RXRRBRRFQILYRBRXR (SEQ ID NO. 4)
RXRRBRRYQFLIRBRXR (SEQ ID NO. 5)
RXRRBRRQFLRBRXR (SEQ ID NO. 6)
RXRRBRRFLRBRXR (SEQ ID NO. 7)
RXRRBRFQILYRBRXR

2. Increase in FLSMN2 Expression in Skeletal Muscles, Brain Compartments and Spinal Cord Compartments by Intravenous Delivery of Peptide 17-PMO or Peptide 14-PMO in SMO Mice.

The inventors then tested the in vivo administration of peptides 17 and 14 and the currently available peptides 1-7 described above by conjugating the peptides to an antisense oligonucleotide therapeutic specifically a PMO. The antisense oligonucleotide was specifically directed at treating SMA by increasing full length SMN2 transcript production.

Smn1tm1Hung/wt; SMN2tg/tg and Smn1wt/wt; SMN2tg/tg mice were treated at 7-8 weeks of age with two administrations given two days (approximately 48 hours) apart of 15 mg/kg peptide 17-PMO, peptide 14-PMO conjugates or saline only (control). Tissues were harvested one week post administration. Quantitative PCR was performed on extracted RNA to analyse the amount of full-length SMN2 transcripts (in relation to total SMN2 transcripts), see FIG. 2. Each treatment groups was normalised to their saline controls, represented by the dashed line. Statistical significance determined by Student's t-test *p≤0.05, p≤0.005, *p≤0.0005, ****p≤0.00005.

Figure 2:
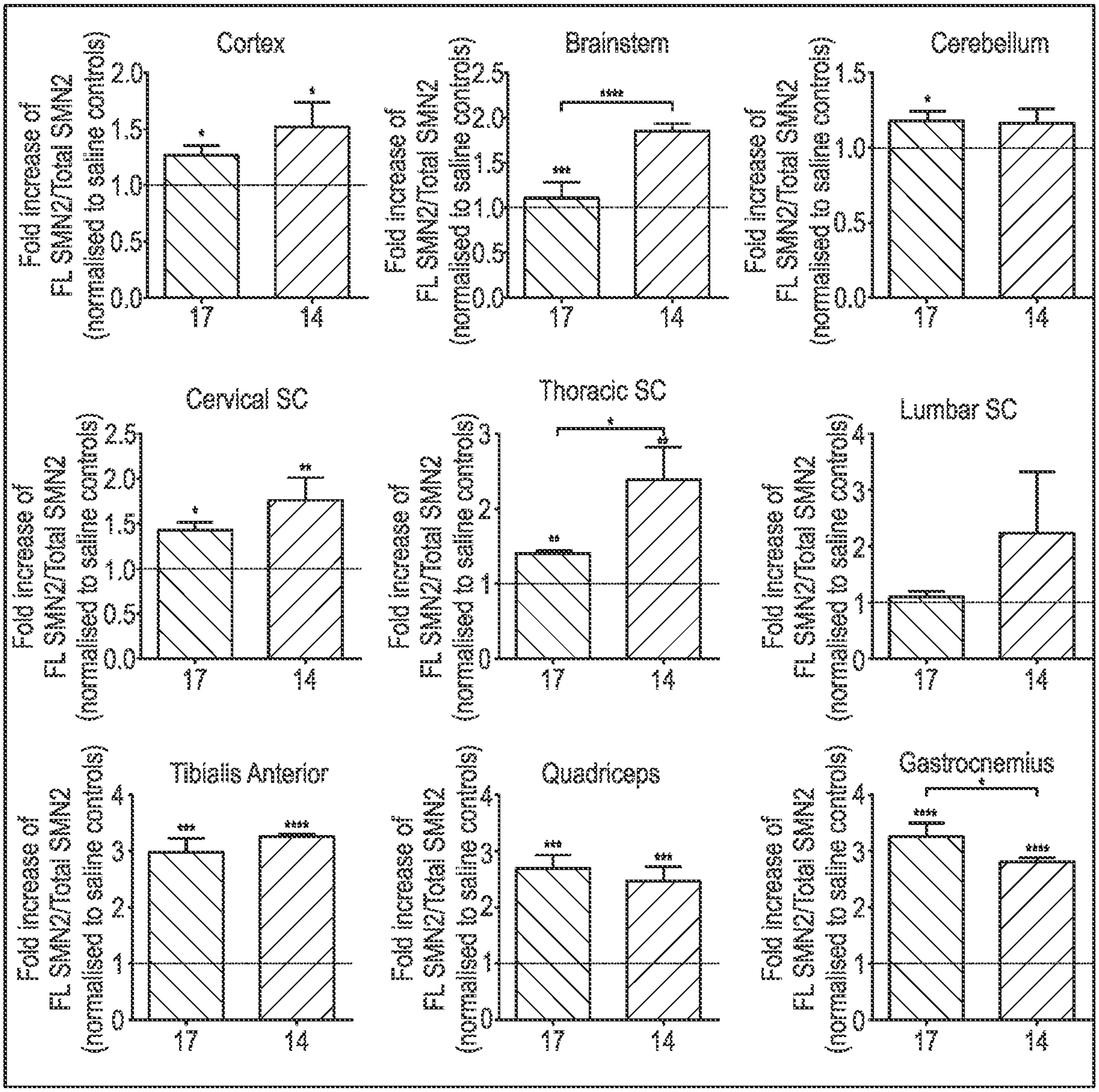
FIG. 2: Shows a series of graphs showing increase in full length SMN2 transcript expression analysed via qPCR in three skeletal muscles (tibialis anterior (TA), quadriceps (Quad) and gastrocnemius (Gastro)), three brain compartments (cortex, brainstem, and cerebellum) and three spinal cord compartments (cervical, thoracic, and lumbar) following intravenous delivery of peptide 17-PMO conjugate and peptide 14-PMO conjugate in SMA adult mice at a dose of 2×15 mg/kg given approximately 48 hours apart. Tissues were harvested 7 days post final administration. Expression levels shown are normalised to saline treated controls, represented by dashed line). Data represented as mean±SD (*P≤0.05; P≤0.005; *P≤0.0005; ****P≤0.00005 by Student's t test in comparison to saline treated controls)

Quantitative PCR analysis of brain, spinal cord and skeletal muscle tissues showed a significant increase in the amount of full-length SMN2 (FLSMN2) transcripts in several areas of the brain and spinal cord (FIG. 2). Treated skeletal muscles gave around a 3-fold increase in full-length SMN2 expression.

Quantitative data for levels of cell penetration of the peptides in vivo, measured by an increase in full-length SMN2 transcripts, are shown in Table 3 for the peptide 14 conjugate and the peptide 17 conjugate when compared with currently available peptide conjugates to the same antisense oligonucleotide. Data could not be obtained for TA skeletal muscle after treatment with peptide 6 conjugate in this experiment. However, the data demonstrate that cell penetration is increased in several compartments of the central nervous system and the skeletal muscle for peptide 14 and peptide 17 of the invention when compared with currently available peptides 1-7.

Specifically, peptide 6 can be compared with peptide 17 as both share a very similar sequence with the exception that peptide 17 of the invention has a glycosylated serine residue in place of a hydrophobic residue. Peptide 2 can be compared directly with peptide 14 as both share the same sequence with the exception that peptide 14 of the invention has a glycosylated serine residue in place of a glutamine residue and contains an additional linker beta-alanine. Peptide 17 shows increased cell penetration in the cortex, cerebellum, cervical, and thoracic compartments of the CNS, and increases in skeletal muscle penetration compared with peptide 6 of up to 60.2%. Peptide 14 shows increased cell penetration in the cortex, brainstem, cerebellum, thoracic and lumbar compartments of the CNS when compared with peptide 2 of up to 59.7%.

Figure 7:
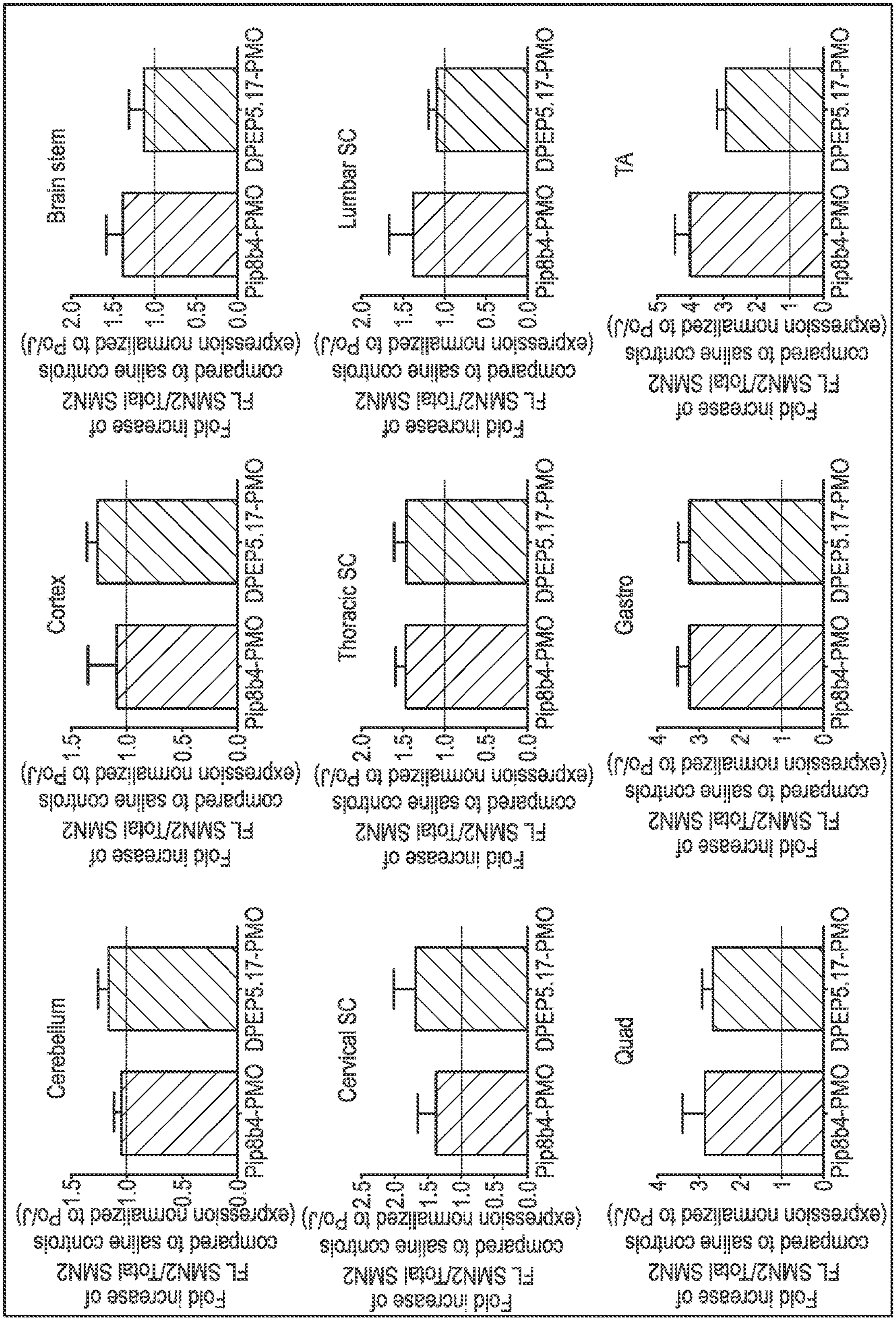
FIG. 7: Shows a series of graphs showing increase in full length SMN2 transcript expression analysed via qPCR in three skeletal muscles (tibialis anterior (TA), quadriceps (Quad) and gastrocnemius (Gastro)), three brain compartments (cortex, brainstem, and cerebellum) and three spinal cord compartments (cervical, thoracic, and lumbar) following intravenous delivery of peptide 17-PMO conjugate and currently available peptide 6-PMO conjugate. Expression levels shown are normalised to saline treated controls, represented by dashed line). Data represented as mean±SD (*P≤0.05; P≤0.005; *P≤0.0005; ****P≤0.00005 by Student's t test in comparison to saline treated controls)

Further data was obtained to show a direct comparison of peptide 6 which is a currently available carrier peptide (designated Pip8b4) with peptide 17; a carrier peptide of the invention. Two systemic intravenous doses of 15 mg/kg of peptide-PMO conjugates were administered 48 hours apart in adult intermediate SMA mice (non-symptomatic SMN2 transgenic mice) and critical central and peripheral tissues were harvested 7 days post-final administration similar to the method described above. Results are shown in FIG. 7. Levels of exon 7 included transcripts (FLSMN) were assayed via qPCR as explained above. The levels of full length transcript were increased by treatment with peptide 17 for each tissue, exceeding the 1 fold increase threshold of FLSMN in all tissues (central spinal cord and peripheral skeletal muscle and liver). Moreover, peptide 17 of the invention showed equivalent or improved activity in the critical central brain tissues of the cerebellum and cortex when compared with the closest currently available carrier peptide; peptide 6. This indicates that the peptides of the invention are more effective than those that are currently available. This further indicates that the inventive peptides are effective as a therapy.

3. Toxicology Profile of Glucosylated Peptide-PMO Conjugates

The inventors then further tested the toxicology of peptide 17 of the invention (designated DPEP5.17) in comparison with the currently available peptide; peptide 6 (designated Pip8b4).

Figure 8:
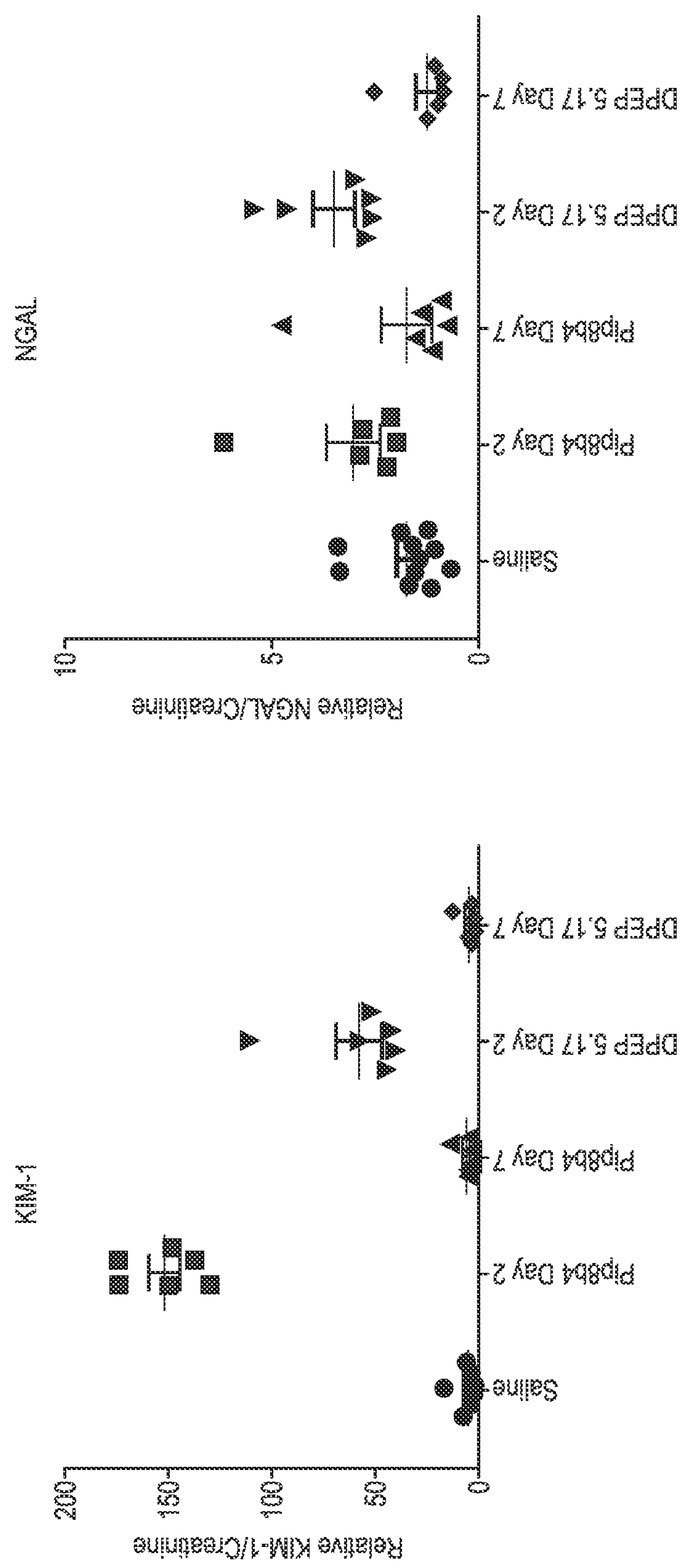
FIG. 8: Shows urinary KIM-1 and Lipocalin-2 (NGAL) levels normalised to creatinine, two and seven days post-administration of 25 mg/kg single dose of currently available peptide 6 conjugate (Pip8b4-PMO) or peptide 17 conjugate (DPEP 5.17-PMO)

Urinary and serum markers of kidney and liver toxicity were measured following a single dose administration of saline or the relevant peptide-PMO conjugate to 8 week old adult C57/BL10 female mice (N=6 per group). A bolus IV (tail vein) injection was administered and urine collected Day 2 and Day 7 after administration. Animals were then scarified prior to necropsy in which kidney, liver, diaphragm, heart, TA, gastric and serum were collected. Urine clinical indicators: KIM-1, NGAL were measured by ELISA (R&D cat #MKM100) with samples diluted to fit within standard curve. Values were normalised to urinary creatinine levels (Harwell) to account for urine protein concentration. Results are shown in FIG. 8.

Group 1—0.9% Saline
Group 2—25 mg/kg Pip8b4-PMO SMN
Group 3—25 mg/kg DPEP5.17-PMO SMN By 7 days post administration, the levels of both KIM-1 and NGAL were lower in mice which had received the inventive peptide 17 than those which had received peptide 6. Furthermore, 2 days after administration, the levels of the marker KIM-1 were far lower in mice which had received the inventive peptide 17 than those which had received peptide 6. This indicates that the peptides of the invention have a better toxicology profile than those that are currently available, and therefore a lower toxicity than the currently available peptides. This indicates that the inventive peptides are suitable for use as a therapy.

4. Cell Screening of Glucosylated Peptide-PMO Conjugates for Exon Inclusion in Human SMA Patient Fibroblast Cell Culture of Peptides 8-54.

In order to generate further peptide candidates containing a glycosylated Serine residue for in vivo evaluation, the inventors synthesized a range of similarly glycosylated peptides, conjugated them to the same PMO therapeutic and screened the resultant P-PMO conjugates in human SMA patient fibroblast cell culture, which assesses their ability to enter cell nuclei to give exon inclusion.

These further peptides are shown in Table 2, as peptides 8-80. Such a cellular screen provides candidates that are competent for entering cells and effecting SMN2 exon inclusion of an attached PMO. Some important conclusions could be reached as to what changes affected exon inclusion activity in cells. In addition, P-PMO conjugates were checked by MALDI-TOF spectrometry for their serum stability in mouse serum.

Figure 3:
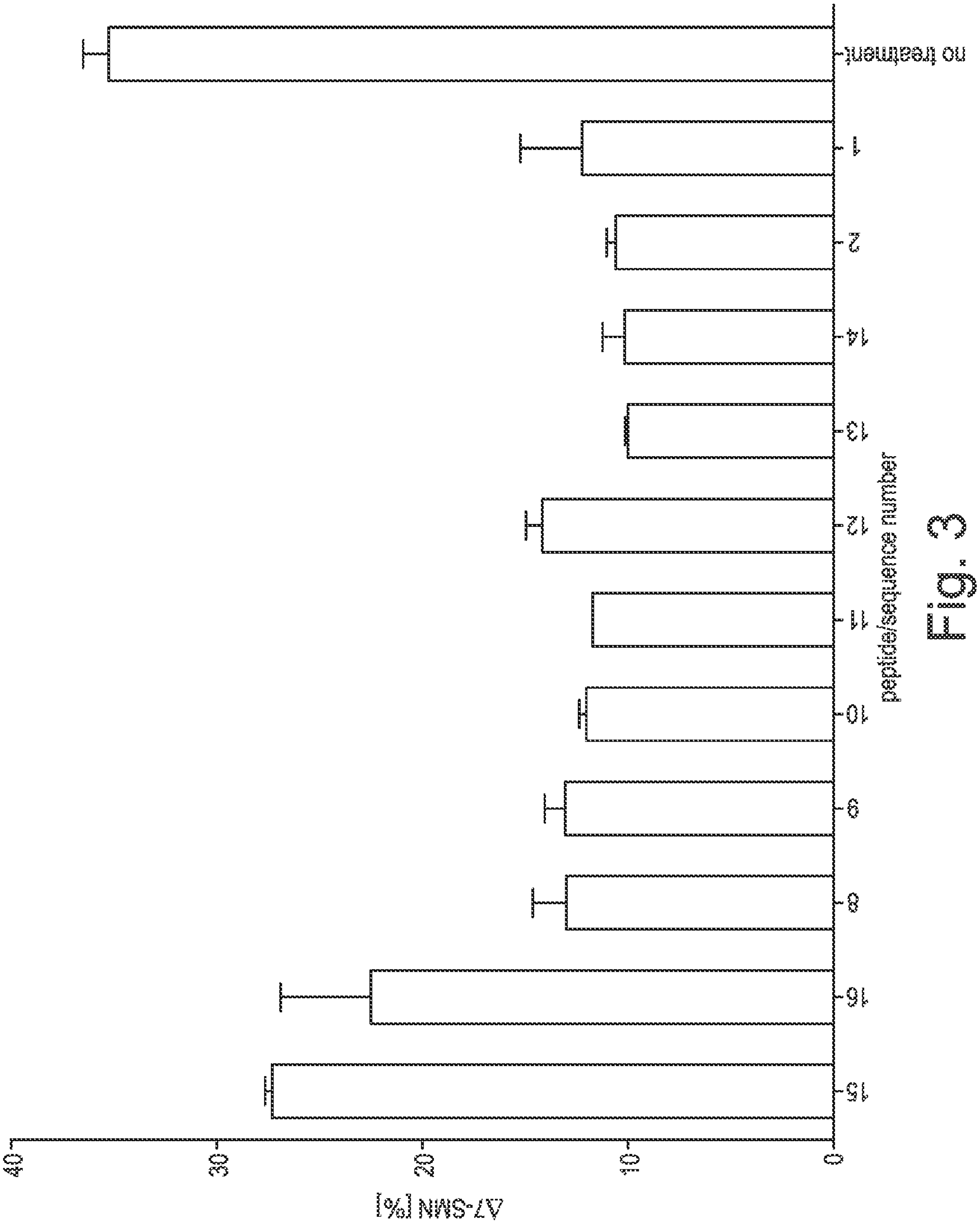
FIG. 3: Cell screening of glucosylated peptide-PMO conjugates for SMN2 exon 7 inclusion in human SMA patient fibroblast cell culture for peptides 1-16 by semi quantitative PCR at 50 nM concentration.
Figure 4:
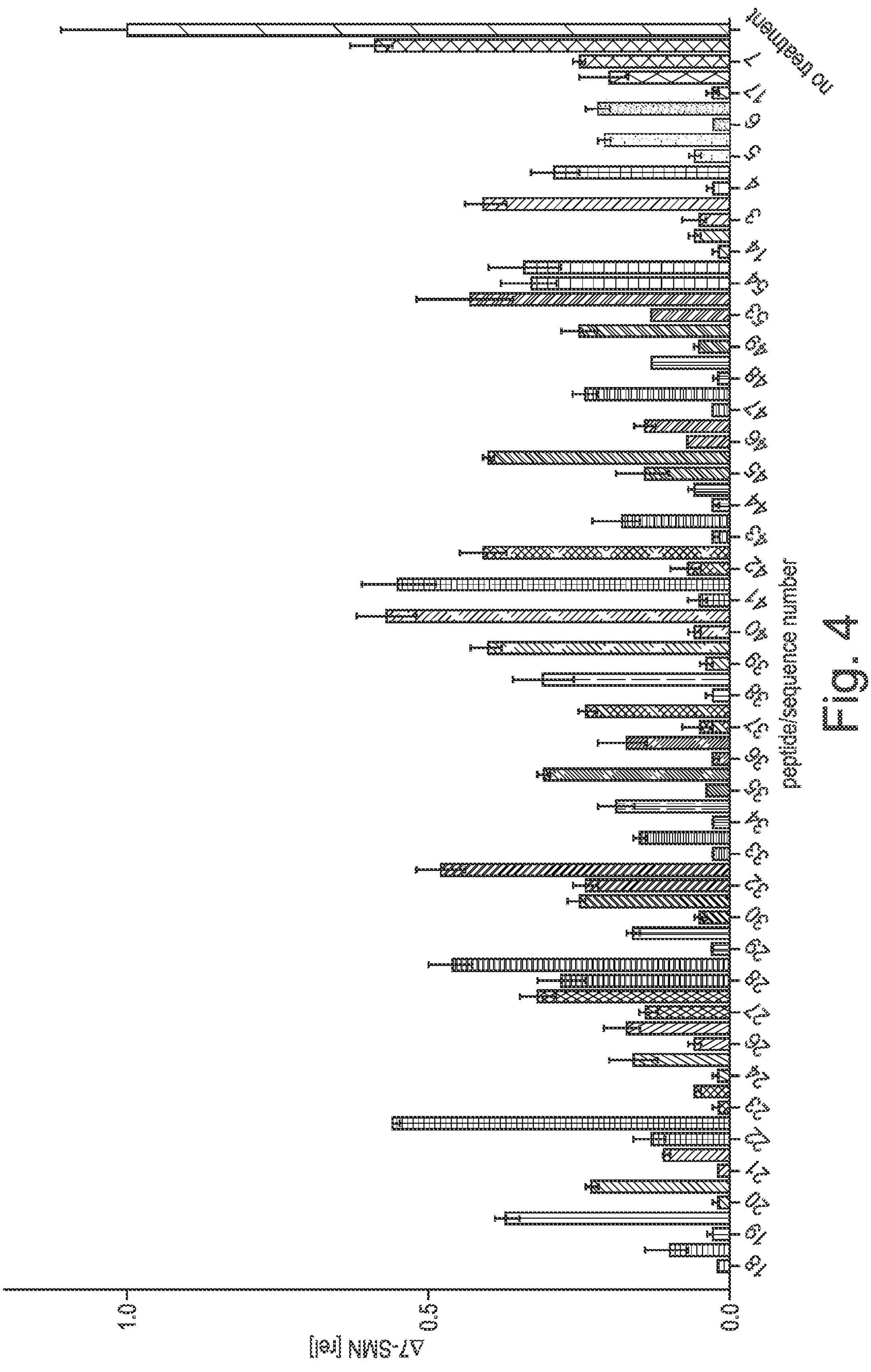
FIG. 4: Cell screening of glucosylated peptide-PMO conjugates for SMN2 exon 7 inclusion in human SMA patient fibroblast cell culture for peptides 3-54 by qPCR at different concentrations (667 nM and 2 μM)

In the first screen (FIG. 3, D-PEP5 peptides 8-16 and FIG. 4, D-PEP5 peptides 14, and 17-54), a study of 10-Arginine peptides related to the first DPEP5 peptide number 14 was undertaken. It was found that replacement of all X residues by B (peptide 18) had no significant effect on cell activity. Replacement of S*FL by S in the core region (peptide 44) had no significant effect on cell activity. Replacement by S*F resulted in only a slightly reduced activity (peptide 43). The key result is that a glycosylated residue and core domain sequence such as S*FL could be placed in a variety of positions and contexts in the sequence without a large loss in cell activity (peptides 33, 34, 36, and 37). S*FL placed close to the C-terminus (peptide 48) was almost as active as the first peptide, peptide 14.

It was found that exon inclusion activity is generally reduced as the number of Arginine residues is reduced in the peptide. For example, the 9-Arginine sequences peptide 24 and peptide 29 were less active than the first peptide 14, 8-Arginine sequences less active than these and the 7-Arginine peptide 26 slightly less active only.

5. Cell Screening of Glucosylated Peptide-PMO Conjugates for Exon Inclusion in Human SMA Patient Fibroblast Cell Culture of D-PEP5 Peptides 55-72

Figure 5:
FIG. 5: Cell screening of glucosylated peptide-PMO conjugates for SMN2 exon 7 inclusion in human SMA patient fibroblast cell culture for peptides 55-72 by qPCR at different concentrations (667 nM and 2 μM)

Following the screen of D-PEP5 peptides 8-54, a second screen in cells was carried out (FIG. 5) following synthesis of still further glucosylated D-PEP5 peptides 55-72 as shown in (Table 2). For the 8-Arginine peptides, there was no significant alteration in activity levels when FS* (peptides 56 and 57) was replaced by S* (peptides 58 and 59). Double S* (peptide 67) and Triple S* (peptide 68) peptides retained good activity in cells. Amongst the 6-Arginine peptides, by and large these had acceptable activity as PMO conjugates. However, P-PMO conjugates with peptide 70 and peptide 71 showed remarkably good activity.

6. Cell Screening of Glycosylated Peptide-PMO Conjugates for Exon Inclusion in Human SMA Patient Fibroblast Cell Culture of D-Pep5 Peptides 73-80.

Figure 6:
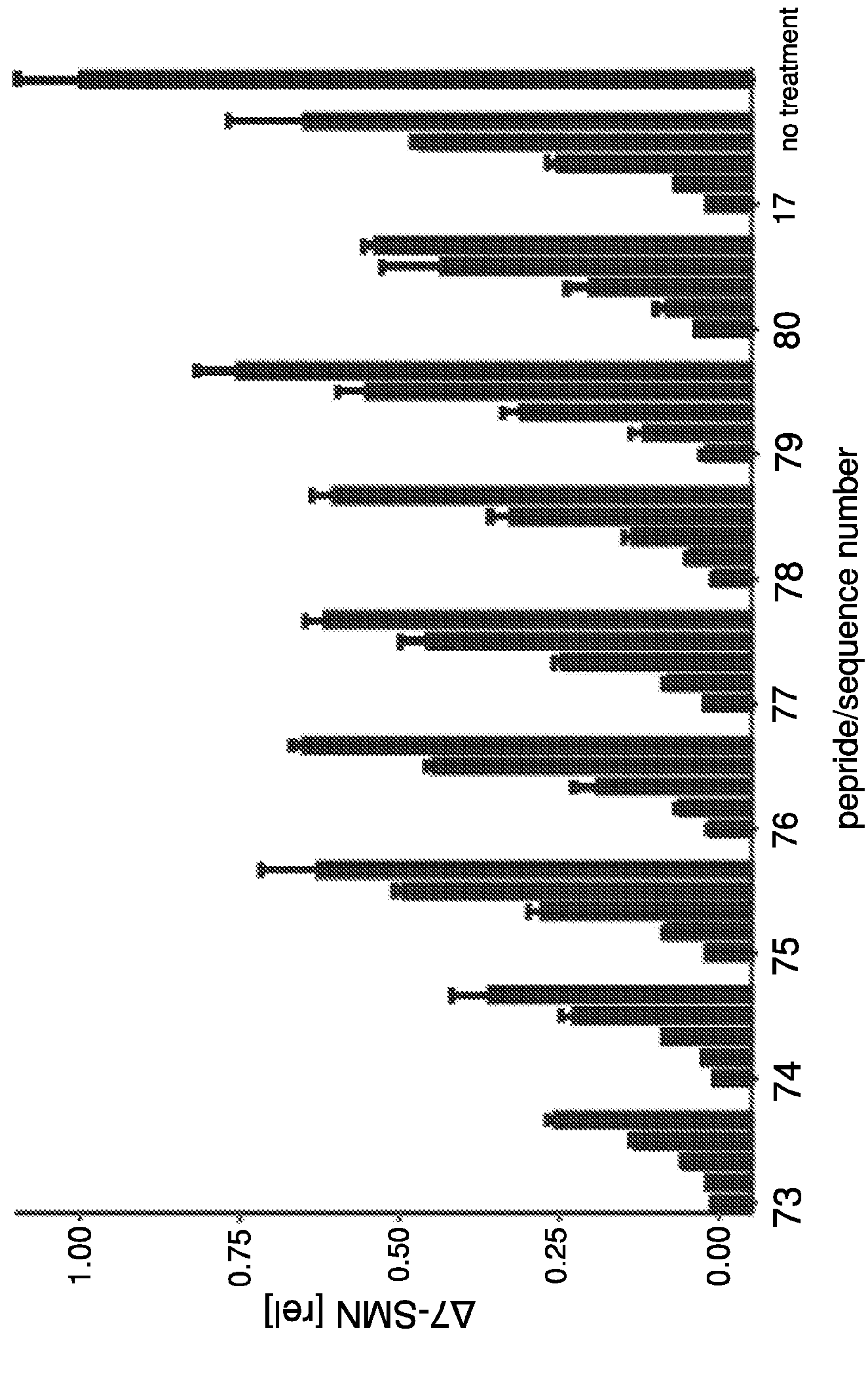
FIG. 6: Cell screening of glycosylated peptide-PMO conjugates for SMN2 exon 7 inclusion in human SMA patient fibroblast cell culture for peptides 73-80 at different concentrations (4 μM, 2 μM, 1 μM, 500 nM, 250 nM)

Following the screen of the D-PEP5 peptides 8-72 a third screen in cells was carried out (FIG. 6) following synthesis of still further glycosylated peptides 73-80 as shown in (Table 2). For the 8-Arginine peptides, there was no significant alteration in activity levels when S* was replaced by different glycosylated serine and asparagine moieties N*, and $S^{2}$*-$S^{6}$* (peptide 75 to peptide 79). Improved activity was seen for peptide 74 carrying a glycosylated unnatural D-serine residue and thereby preventing protease induced cleavage of the peptide. Further stabilisation of the peptide by introducing a unnatural amino acid (peptide 73, Z=Tic=1, 2,3,4-tetrahydroisoquinoline-3-carboxylic acid) within the hydrophobic core-region greatly improved alteration in activity levels and even showed good activity at low doses.

The three in vitro screens performed evaluate the ability of the inventive peptides to enter cells and effect SMN2 exon 7 inclusion in human SMA patient fibroblast cell culture and is a pre-requisite before in vivo evaluation.

In summary, the present inventors have synthesised and demonstrated the improved effectiveness of a series of peptides having one or more directly glucosylated amino acid residues present within an arginine rich structure in penetrating into compartments of the CNS and muscular system for use as carriers for therapeutic molecules with a lower toxicity.

Materials and Methods

Reagents and General Methods

9-Fluorenylmethoxycarbonyl (Fmoc) protected L-amino acids, and the Fmoc-β-Ala-OH preloaded Wang resin (0.19 mmol $g^{-1}$) were obtained from Merck (Hohenbrunn, Germany). HPLC grade acetonitrile, methanol and synthesis grade N-methyl-2-pyrrolidone (NMP) were from Fisher Scientific (Loughborough, UK). Peptide synthesis grade N,N-dimethylformamide (DMF), benzotriazole-1-yl-oxy-tris-pyrrolidino-phosphonium (PyBOP) and diethyl ether were obtained AGTC Bioproducts (Yorkshire, UK). Piperidine and trifluoroacetic acid (TFA) were obtained from Alfa Aesar (Heysham, England). PMO was purchased from Gene Tools Inc. (Philomath, USA). Fetal bovine serum, mouse serum and Superscript III Platinum One-Step qRT-PCR Kit and Platinum PCR SuperMix High Fidelity were obtained from Thermofisher Scientific (Waltham, US). iScript cDNA Synthesis Kit was obtained from Biorad (Hercules US). All other reagents were obtained from Sigma-Aldrich (St. Louis, MO, USA) unless otherwise stated. MALDI-TOF mass spectrometry was carried out using a Voyager DE Pro BioSpectrometry workstation. A stock solution of 10 mg $mL^{-1}$ of α-cyano-4-hydroxycinnamic acid or sinapinic acid in 60% acetonitrile in water containing 0.1% TFA was used as matrix. Fmoc-L-Ser($Ac_4$-β-D-Glc)-OH═S*, Fmoc-D-Ser($Ac_4$-β-D-Glc)-OH═$S^{1}$*, Fmoc-L-Ser($Ac_4$-β-L-Glc)-OH═$S^{2}$*, Fmoc-L-Ser($Ac_4$-β-D-Gal)-OH═$S^{6}$*, Fmoc-L-Ser($Ac_4$-α-D-Man)-OH=$S^{3}$*, 2-N-Fmoc-4-N-[$Ac_4$-β-D-Glc)-L-Asn-OH═N*, Fmoc-L-Ser(β-D-Lac($Ac)_7$)-OH═$S^{4}$*, were synthesized as previously described (15-18).

Synthesis of Peptides on 100 μMol Scale

Peptides were synthesized on a 100 μmol scale using a CEM Liberty™ microwave Peptide Synthesizer (Buckingham, UK) and Fmoc chemistry following manufacturer's recommendations. The side chain protecting groups used were labile to trifluoroacetic acid treatment and the peptide was synthesized using a 5-fold excess of Fmoc-protected amino acids (0.25 mmol) that were activated using PyBOP (5-fold excess) in the presence of DIPEA or with DIC|Oxyma. Piperidine (20% v/v in DMF) was used to remove N-Fmoc protecting groups. The coupling was carried out once at 75° C. for 5 min at 60-watt microwave power except for arginine and the glycosylated amino acid residues, which were coupled twice each.

Histidine and cysteine residues were coupled once at 50° C. for 5 min at 60-watt microwave power. Each deprotection reaction was carried out at 75° C. twice, once for 30 sec and then for 3 min at 35-watt microwave power. Once synthesis was complete, the resin was washed with DMF (3×50 mL) and the N-terminus of the solid phase bound peptide was acetylated with acetic anhydride in the presence of DIPEA. The peptide was cleaved from the solid support by treatment with a cleavage cocktail consisting of trifluoroacetic acid (TFA): 3,6-dioxa-1,8-octanedithiol (DODT): $H_2O$: triisopropylsilane (TIPS) (94%: 2.5%: 2.5%: 1%, 10 mL) or trifluoroacetic acid (TFA): $H_2O$: m-cresol: triisopropylsilane (TIPS) (94%: 2.5%: 2.5%: 1%, 1 mL) or trifluoroacetic acid (TFA): $H_2O$: triisopropylsilane (TIPS) (96.5%: 2.5%: 1%, 1 mL) for 2 h at room temperature for 2-3 h at room temperature. Excess TFA was removed by blowing N2 through the peptide solution. The cleaved peptide was precipitated via the addition of ice-cold diethyl ether and centrifuged at 3000 rpm for 5 min. The peptide pellet was washed in ice-cold diethyl ether thrice. The crude peptide was dissolved in water, analyzed and purified by RP-HPLC on Phenomenex Jupiter column (21.2×250 mm, C18, 10 μm) at a flow rate of 20 mL/min with the following gradient (A: 0.1% TFA, B: 90% $CH_3CN$, 0.1% TFA) 0-2 min 5% B 2-35 min 5%-60% B 35-40 min 60%-90% B used. The fractions containing the desired peptide were combined and lyophilized to give the product as a white solid.

Synthesis of a Library of Peptide Variants on 5 μMol Scale

Each peptide was prepared on a 5 μmal scale using an Intavis Parallel Peptide Synthesizer using Fmoc-Gly-HMP-Tentagel resin (0.2 mmol $g^{-1}$) or Fmoc-β-Ala-Wang Chemmatrix resin (0.3 mmol $g^{-1}$) by applying standard Fmoc chemistry and following manufacturer's recommendations. Double coupling steps were used with a PyBOP/NMM coupling mixture followed by acetic anhydride capping after each step. The peptides were cleaved from the solid support by treatment with a cleavage cocktail consisting of trifluoroacetic acid (TFA): 3,6-dioxa-1,8-octanedithiol (DODT): $H_2O$: triisopropylsilane (TIPS) (94%: 2.5%: 2.5%: 1%, 1 mL) or trifluoroacetic acid (TFA): $H_2O$: m-cresol: triisopropylsilane (TIPS) (94%: 2.5%: 2.5%: 1%, 1 mL) or trifluoroacetic acid (TFA): $H_2O$: triisopropylsilane (TIPS) (96.5%: 2.5%: 1%, 1 mL) for 2 h at room temperature. After peptide release, excess TFA was removed by blowing $N_2$ gas into the TFA solution. The crude peptide was precipitated by the addition of cold diethyl ether (12 mL) and centrifuged at 2500 rpm for 5 min. The crude peptide pellet was washed thrice by cold diethyl ether (3×12 mL). The crude peptide was dissolved in 1500 μL $H_2O$: $CH_3CN$ mixture and purified by RP-HPLC using a Phenomenex Jupiter column (10×250 mm, C18, 10 mm) at a flow rate 5 mL/min with the following gradient (A: 0.1% TFA, B: 90% $CH_3CN$, 0.1% TFA) 0-2 min 5% B 2-35 min 5%-60% B 35-40 min 60%-90% B. The fractions containing the desired peptide were combined and lyophilized to yield the peptide as a white solid (see Table 1 for yields).

Synthesis of PMO-Peptide Conjugates

The following PMO antisense sequences targeting the human SMN2-gene were used.

ISS-N1-20 mer: ATT CAC TTT CAT AAT GCT GG (SEQ ID NO.147)

ISS-N1-25 mer: GTA AGA TTC ACT TTC ATA ATG CTG G (SEQ ID NO.148)

The peptide was conjugated to the 3'-end of the PMO through its C-terminal carboxyl group. This was achieved using 2.5 and 2 equivalents of HBTU and HOAt in NMP respectively in the presence of 2.5 equivalents of DIPEA and 2.5 fold excess of peptide over PMO dissolved in DMSO was used.

| PMO | Peptide-COOH | HBTU | HOAt | DIPEA |
|---|---|---|---|---|
| 10 mM | 100 mM | 300 mM | 300 mM | |
| 1 eq. | 2.5 eq. | 5.75 eq. | 5.75 eq. | 5.75 eq. |
| 100 nmol | 250 nmol | 575 nmol | 575 nmol | 575 nmol |
| 10 μl | 2.5 μl | 1.92 μl | 1.92 μl | 0.11 μl |

To a solution of peptide (250 nmol) in N-methylpyrrolidone (NMP, 2.5 μL) were added HBTU (1.92 μL of 0.3 M in NMP), HOAt in (1.92 μL of 0.3 M NMP), DIPEA (0.1 μL) and PMO (10 μL of 10 mM in DMSO). The mixture was left for 2-3 h at 40° C. and the sugar protecting groups were globally deprotected by the addition of 10 μl hydrazine hydrate. After 10 min the deprotection reaction was quenched by the addition of ice cold 5% AcOH (1000 μL). This solution was then purified by Ion exchange chromatography using a Resource S HR-16|100 column at a flow rate 6 mL/min with the following gradient (A: 25 mM phosphate buffer pH 7 with 25% ACN, B: 25 mM phosphate buffer pH 7 with 25% $CH_3CN$ and 1M NaCl) 0-2 min 0% B 2-20 min 0%-75% B 20-23 min 100% B, 23-28 100% A. The fractions containing the desired compound were desalted (Amicon 15 Ultracel, MWCO 3 kDa, EMD Millipore) and lyophilized.

Mouse Serum Stability Experiments 10 nmol of lyophilized P-PMO was dissolved in 100 μl mouse serum and incubated at 37° C. for different time periods. Samples were diluted with 300 μl guanidinium-HCl solution (10 ml of 1M guanidinium-HCl containing 1 tablet complete mini protease inhibitor cocktail (Roche, Basel, Switzerland) and with 600 μl ice cold acetonitrile and centrifuged at 14.000 rpm for 3 min. The supernatant was collected and analysed by MALDI TOF MS and ion exchange chromatography.

Cell Culture

GM03813 patient fibroblast cells were cultured in T75 flasks at 37° C., under 5% $CO_2$ in Dulbecco's modified Eagle's medium (DMEM with Glutamax, Thermofisher) supplemented with 10% heat-inactivated fetal bovine serum (FBS Gold, PAA laboratories), 1% penicillin-streptomycin-neomycin antibiotic mixture (PSN, Gibco).

Cytotoxicity

GM03813 patient fibroblasts were seeded out at 1250 cells|well in 100 μl Dulbecco's modified Eagle's medium (DMEM) with GlutaMAX and 10% fetal bovine serum (FBS) (Life Technologies, Inc.) in 96 well plates, and incubated for 16 hours in a cell culture incubator (37° C., 5% $CO_2$, 100% rel. humidity). Afterwards the media was removed and cells were washed once with Opti-Mem and treated with different concentrations of PPMO in Opti-Mem in duplicate for 4 hours at 37° C. Subsequently the transfection mixture was replaced by normal culture media and cells were allowed to grow overnight. On the next day 20 μl of MTS Cell Viability assay (Promega) was added to the wells and incubated for 3 hours before measurement at 490 nm were taken. The cell viability percentage was determined by normalizing the average absorbance of triplicate samples to the mean of untreated samples.

qPCR Analysis of SMN2 Full Length and Δ7 mRNA in Cultured Cells

GM03813 (Coriell Institute) derived from SMA type I patient fibroblast were seeded out at 2500 cells/well in 100 μl Dulbecco's modified Eagle's medium (DMEM) with GlutaMAX and 5% fetal bovine serum (FBS) (Life Technologies, Inc.) in 96 well plates, and incubated for 16 h in a cell culture incubator (37° C., 5% $CO_2$, 100% rel. humidity). On the next day cells were then treated with 10 μl P-PMO at different concentrations (in water) in duplicate for 24 hours. After removal of the supernatant, cells were washed once with PBS-buffer and were lysed in lysis buffer (10 mM Tris, 3 mM $MgCl_2$, 1 mM $CaCl_2$), 1% Triton X-100, 200 u/ml DNase I and 200 u/ml Proteinase K) for 10 min. Afterwards the lysate were transferred into a 96-well plate (Eppendorf twintec) and incubated at 75° C. for 15 min and subsequently cooled to 4° C. and used immediately. The mRNA levels of SMN2 FL, SMN2 Δ7 and GAPDH were quantified using Taqman-based qRT-PCR (Superscript® III Platinium® One Step qRT-PCR, Thermo Fisher) and SMN2 specific Primers and probes (purchased from IDT Integrated DNA Technologies). (19) SMN2 FL and Δ7 mRNAs were normalized to GAPDH.

Endpoint qPCR Analysis of SMN2 Full Length and Δ7 mRNA in Cultured Cells

GM03813 (Coriell Institute) derived from SMA type I patient fibroblasts were seeded out at $1\times10^5$ cells/well in 2000 μl Dulbecco's modified Eagle's medium (DMEM) with GlutaMAX and 10% fetal bovine serum (FBS) (Life Technologies, Inc.) in 6 well plates, and incubated for 2 days (until cells reach a confluency greater than 90%) in a cell culture incubator (37° C., 5% $CO_2$, 100% rel. humidity). Afterwards cells were washed once with PBS and Opti-Mem and cells were then treated with 1000 μl of PPMO in Opti-Mem in duplicates for 4 h. The transfection medium was then replaced with DMEM supplemented with 10% fetal bovine serum and 1% PSN and the cells incubated for a further 20 hr at 37° C. Cells were washed with PBS and 0.5 mL of TRI RNA (Sigma) isolation reagent was added to each well. Cells were frozen at −80° C. for 1 h.

RNA Extraction and Nested RT-PCR Analysis

Total cellular RNA was extracted using TRI reagent with an extra further precipitation with ethanol. The purified RNA was quantified using a Nanodrop® ND-1000 (Thermo Scientific). The RNA (500 ng) was used as a template for 2 step RT-PCR using iScript cDNA Synthesis Kit (Biorad, Hercules US) and Platinum PCR SuperMix High Fidelity (Thermofisher Scientific (Waltham, US). Primers (Forward: 5'-CTC CCA TAT GTC CAG ATT CTC TT-3' (SEQ ID NO.149) and Reverse: 5'-CTA CAA CAC CCT TCT CAC AG-3' (SEQ ID NO.150) were used to amplify full-length (505 bp) and Δ7 SMN2 (451 bp) from cDNA. The products were amplified semi-quantitatively using 30 PCR cycles (94° C. for 30 s, 55° C. for 30 s and 72° C. for 30 s). All PCR products were checked by electrophoresis on 2% agarose gels.

Data Analysis

The images of agarose gels were taken on a Molecular Imager ChemiDoc™ XRS$^+$ imaging system (BioRad, UK) and the images were analysed using Image Lab (V4.1). Microsoft Origin was used to analyse and plot the exon-inclusion assay data, which were expressed as the percentage of Δ7 SMN2 transcript from at least three independent experiments.

Animal Models

Experiments were carried out in the Biomedical Sciences Unit, University of Oxford according to procedures authorized by the UK Home Office. Experiments were performed in SMA like mouse strain FVB.Cg-Smn1$^{tm1Hung}$Tg(SMN2) 2Hung/J, Jackson Laboratory stock number 5058 (28). The line was maintained and heterozygous mice (Smn1$^{tm1HUNG/wt}$; SMN2$^{tg/tg}$) were generated as previously described (21). Two doses of 15 mg/kg (given 2 days, about 48 hours apart) were diluted in 0.9% saline (Sigma) and administered via intravenous tail vein at a volume of 5 µl per gram body weight. Tail vein administrations were performed after warming mice at 32° C. Mice were then restrained in approved apparatus and peptide-PMO conjugates IV administered without anaesthetics. Administered mice were allowed to recover in heat box. Saline treated control animals were selected from littermates and handled in the same manner as the treated animals to control for potential changes in SMN expression due to stress. Tissues were harvested 7 days post final-administration. The tissues harvested included: liver, quadriceps, gastric, TA, brain, brainstem, cerebellum, and spinal cord. Spinal cord was divided into cervical, thoracic and lumbar regions. Tissues were snap frozen in liquid nitrogen and stored at −80° C.

RNA Extraction and cDNA Synthesis

RNA extraction from tissues was carried out using TRIZOL extraction, however another suitable product is Qiagen RNeasy® Mini Kit (Qiagen #74104), following manufacturer's instructions. One microgram of RNA template was used in a 20 µl reverse transcription reaction using ABI High Capacity cDNA Reverse Transcription Kits (Invitrogen, Carlsbad, CA).

SMN mRNA QPCR

RNA extraction from harvested tissues was carried out using TRIZOL extraction, however another suitable product is Qiagen RNeasy® Mini Kit. One microgram of RNA template was used in a 20 µl reverse transcription reaction using ABI High Capacity cDNA Reverse Transcription Kits (Invitrogen, Carlsbad, CA). Synthesized cDNA was diluted 1:5 with ddH2O and used at 20 ng per 20 µl QPCR reaction using Power SYBR® Green Master Mix (Life Technologies). Real time QPCR is performed and analysed on Applied Biosystems® StepOnePlus™ real-time PCR system (Life Technologies). Full length SMN2 transcript (FLSMN2) was amplified using gene-specific primers Exon 6 Fwd: 5'-GCT TTG GGA AGT ATG TTA ATT TCA-3' (SEQ ID NO.151), Exons 7-8 Rev: 5'-CTA TGC CAG CAT TTC TCC TTA ATT-3' (SEQ ID NO.152). SMN2 transcripts representing both FL and Δ7 mRNA were amplified using gene specific primers (Exon 2a Fwd: 5'-GCG ATG ATT CTG ACA TTT GG-3' (SEQ ID NO.153), Exon 2b Rev: 5'-GGA AGC TGC AGT ATT CTT CT-3' (SEQ ID NO.154). Cycle conditions: 95° C. for 10 minutes holding stage, followed by 40 cycles of 15 seconds at 95° C. and 1 minute at 60° C. The melt curve was determined from 60° C. to 95° C. in 0.6° C. steps. Transcripts were normalized to Polymerase (RNA) II polypeptide J (PolJ) levels. PolJ Forward: 5'-ACCACACTCTGGGGAACATC-3' (SEQ ID NO.155); PolJ Reverse: 5'-CTCGCTGATGAGGTCTGTGA-3' (SEQ ID NO.156). ΔΔCt was calculated as the difference between the ΔCt values, determined with the equation (PCR efficiency)$^{-Ct}$. The PCR efficiency was determined by LinRegPCR software (22,23). One-way ANOVA followed by Tukey's multiple comparisons test was performed using GraphPad Prism version 6.05 for Windows (Graph Pad Software, La Jolla California USA, www.graphpad.com).

REFERENCES

1. Singh, N. K., Singh, N. N., Androphy, E. J. and Singh, R. N. (2006) Splicing of a critical exon of human Survival Motor Neuron is regulated by a unique silencer element located in the last intron. *Mol. Cell Biol.,* 26, 1333-1346.
2. Hua, Y., Vickers, T. A., Baker, B. F., Bennett, C. F. and Krainer, A. R. (2007) Enhancement of SMN2 Exon 7 inclusion by antisense oligonucleotides targeting the exon. *PLoS Biology,* 5, e73.
3. Disterer, P., Kryczka, A., Liu, Y., Badi, Y. E., Wong, J. J., Owen, J. S. and Khoo, B. (2014) Development of therapeutic splice-switching oligonucleotides. *Human Gene Therapy,* 25, 587-598.
4. Hua, Y., Sahashi, K., Rigo, F., Hung, G., G., H., Bennett, C. F. and Krainer, A. R. (2011) Peripheral SMN restoration is essential for long-term rescue of a severe spinal muscular atrophy mouse model. *Nature,* Δ78, 123-126.
5. Zhou, H., Janghra, N., Mitrpant, C., Dickinson, R. L., Anthony, K., Price, L., Eperon, I. C., Wilton, S. D., Morgan, J. and Muntoni, F. (2013) A novel morpholino oligomer targeting ISSN-1 improves rescue of severe spinal muscular atrophy transgenic mice. *Human Gene Therapy,* 24, 331-342.
6. Farkhani, S. M., Valizadeh, A., Karami, H., Mohammadi, S., Sohrabi, N. and Badrzadeh, F. (2014) Cell penetrating peptides: efficient vectors for delivery of nanoparticles, nanocarriers, therapeutic and diagnostic molecules. *Peptides,* 57, 78-94.
7. Kang, T., Gao, X. and Chen, J. (2014) Harnessing the capacity of cell-penetrating peptides for drug delivery to the central nervous system. *Curr. Pharm. Biotechnol.,* 15, 220-230.
8. Pardridge, W. M. (2012) Drug transport across the blood-brain barrier. *J. Cereb. Blood Flow Metab.,* 32, 1959-1972.
9. Jearawiriyapaisarn, N., Moulton, H. M., Buckley, B., Roberts, J., Sazani, P., Fucharoen, S., Iversen, P. L. and Kole, R. (2008) Sustained dystrophin expression induced by peptide-conjugated morpholino oligomers in the muscles of mdx mice. *Mol. Ther.,* 16, 1624-1629.
10. Wu, B., Moulton, H. M., Iversen, P. L., Juang, J., Li, J., Spurney, C. F., Sali, A., Guerron, A. D., Nagaraju, K., Doran, T. et al. (2008) Effective rescue of dystrophin improves cardiac function in dystrophin-deficient mice by a modifies morpholino oligomer. *Proc. Natl. Acad. Sci. USA,* 105, 14814-14819.
11. Yin, H., Moulton, H. M., Seow, Y., Boyd, C., Boutilier, J., Iversen, P. and Wood, M. J. A. (2008) Cell-penetrating peptide-conjugated antisense oligonucleotides restore systemic muscle and cardiac dystrophin expression and function. *Human Molecular Genetics,* 17, 3909-3918.
12. Ivanova, G. D., Arzumanov, A., Abes, R., Yin, H., Wood, M. J. A., Lebleu, B. and Gait, M. J. (2008) Improved cell-penetrating peptide-PNA conjugates for splicing redirection in HeLa cells and exon skipping in mdx mouse muscle. *Nucleic Acids Res.,* 36, 6418-6428.
13. Yin, H., Moulton, H. M., Betts, C., Merritt, T., Seow, Y., Ashraf, S., Wang, Q., Boutilier, J. and Wood, M. J. A. (2010) Functional rescue of dystrophin-deficient mdx mice by a chimeric peptide-PMO. *Mol. Ther.,* 18, 1822-1827.
14. Hammond, S. M., Hazell, G., Shabanpoor, F., Saleh, A. F., Bowerman, M., Sleigh, J., Meijboom, K., Tabot, K., Gait, M. J. and Wood, M. J. A. (2016) Systemic peptide-mediated oligonucleotide therapy improves long-term survival in spinal muscular atrophy *Proc. Nat. Acad. Sci. USA,* 113, doi: 10.1073/pnas.1605731113.

15. Arsequell, G., Sárries, N. and Valencia, G. (1995) Synthesis of glycosylated hydroxyproline building blocks. *Tetrahedron Lett.,* 36, 7323-7326.
16. Elofsson, M., Walse, B. and J., K. (1991) Building blocks for glycopeptide synthesis: glycosylation of 3-mercaptopropionic acid and Fmoc amino acids with unprotected carboxyl groups. *Tetrahedron Lett.,* 32, 7613-7616.
17. Lefever, M. R., Szabó, L. Z., Anglin, B., Ferracane, M., Hogan, J., Cooney, L. and Polt, R. (2012) Glycosylation of α-amino acids by sugar acetate donors with InBr3. Minimally competent Lewis acids. *Carbohydrate Res.,* 351, 121-125.
18. Salvador, L. A., Elofsson, M. and Kihlberg, J. (1995) Preparation of building blocks for glycopeptide synthesis by glycosylation of Fmoc amino acids having unprotected carboxyl groups. *Tetrahedron,* 51, 5643-5656.
19. Naryshkin, N. A., Weetall, M., Dakka, A., Narasimhan, J., Zhao, X., Feng, Z., Ling, K. K., Karp, G. M., Qi, H., Woll, M. G. et al. (2014) Motor neuron disease. SMN2 splicing modifiers improve motor function and longevity in mice with spinal muscular atrophy. *Science,* 345, 688-693.
20. Hsieh-Li, H. M., Chang, J.-G., Jong, Y.-J., Wu, M.-H., Wang, N. M., Tsai, C. H. and Li, H. (2000) A mouse model for spinal muscular atrophy. *Nature Genetics,* 24, 66-70.
21. Gogliotti, R. G., Hammond, S. M., Lutz, C. and DiDonato, C. J. (2010) Molecular and phenotypic reassessment of an infrequently used mouse model for spinal muscular atrophy. *Biochem. Biophys. Res. Commun.,* 391, 517-522.
22. Ramakers, C., Ruijter, J. M., Lekanne Deprez, R. H. and Moorman, A. F. M. (2003) Assumption-free analysis of quantitative real-time polymerase chain reaction (PCR) data. *Neuroscience Letters,* 339, 62-66.
23. Ruijter, J. M., Ramakers, C., Hoogaars, W. M. H., Karlen, Y., Bakker, O., van den Hoff, M. J. B. and Moorman, A. F. M. (2009) Amplification efficiency: linking baseline and bias in the analysis of quantitative PCR data *Nucleic Acids Res.,* 37, e45.

TABLE 1

| Peptide number incorporating corresponding SEQ ID. NO. | Sequence |
|---|---|
| 1 | Ac-RXRRBRRXRYQFLIRXRBRXR-B |
| 2 | Ac-RXRRBRRXRQFLRXRBRXR-B |
| 3 | Ac-RXRRBRRFQILYRBRXR-B |
| 4 | Ac-RXRRBRRYQFLIRBRXR-B |
| 5 | Ac-RXRRBRRQFLRBRXR-B |
| 6 | Ac-RXRRBRRFLRBRXR-B |
| 7 | Ac-RXRRBRFQILYRBRXR-B |
| 14 | Ac-RXRRBRRXRS*FLRXRBRXR-BB |
| 17 | Ac-RXRRBRR FS*RBRXR-B |

TABLE 2

| Peptide number incorporating corresponding SEQ ID. NO. | Sequence |
|---|---|
| 1 | Ac-RXRRBRRXRYQFLIRXRBRXR-B |
| 2 | Ac-RXRRBRRXRQFLRXRBRXR-B |
| 3 | Ac-RXRRBRRFQILYRBRXR-B |
| 4 | Ac-RXRRBRRYQFLIRBRXR-B |
| 5 | Ac-RXRRBRRQFLRBRXR-B |
| 6 | Ac-RXRRBRRFLRBRXR-B |
| 7 | Ac-RXRRBRFQILYRBRXR-B |
| 8 | Ac-RXRRBRRXRQFLRXRBRXRS*-B |
| 9 | Ac-RXRRBRRXRQFLRXRS*RXR-B |
| 10 | Ac-RXRRS*RRXRQFLRXRBRXR-B |
| 11 | Ac-S*RXRRBRRXR QFL RXRBRXR-B |
| 12 | Ac-RXRRBRRXR S*QFLS*RXRBRXR-B |
| 13 | Ac-RXRRBRRXR S*QFLRXRBRXR-B |
| 14 | Ac-RXRRBRRXR S*FLRXRBRXR-BB |
| 15 | (Ac-S*BRKBRKRBBR)2K-B |
| 16 | Ac-GFTGPLS*BRKBRKRBBR)2K-B |
| 17 | Ac-RXRRBRR FS*RBRXR-B |
| 18 | Ac-RBRRBRRBR S*FL RBRBRBR-G |
| 19 | Ac-RGRRGRRGR S*FL RGRGRGR-G |
| 20 | Ac-RPRRPRRPR S*FL RPRPRPR-G |
| 21 | Ac-R**Hyp**RR**Hyp**RR**Hyp**RS*FLR**Hyp** R**Hyp**R**Hyp**R-G<br>**Hyp** = hydroxy-proline |
| 22 | Ac-RARRARRAR S*FL RARARAR-G |
| 23 | Ac-R**Cy**RR**Cy**RR**Cy**RS*FLR **Cy**R **Cy**R **Cy**R-G<br>**Cy** = 1-(amino) cyclohexanecarboxylic acid |
| 24 | Ac-RRBRRBRS*FLRBRBRBR-G |
| 25 | Ac-RBRRBRS*FLRBRBRBR-G |
| 26 | Ac-RRBRS*FLRBRBRBR-G |
| 27 | Ac-RBRS*FLRBRBRBR-G |
| 28 | Ac-RS*FLRBRBRBR-G |
| 29 | Ac-RBRRBRRBRS*FLRBRBR-G |
| 30 | Ac-RBRRBRRBRS*FLRBR-G |
| 31 | Ac-RBRRBRRBRS*FLR-G |
| 32 | Ac-RBRRBRRBRS*FL-G |
| 33 | Ac-RBRRBRRBRS*FLRBRBRR-G |
| 34 | Ac-RBRRBRRBRS*FLRBRRR-G |
| 35 | Ac-RBRRBRRBRS*FLRRRR-G |

TABLE 2-continued

| Peptide number incorporating corresponding SEQ ID. NO. | Sequence |
|---|---|
| 36 | Ac-RBRRBRRRS*FLRBRBRBR-G |
| 37 | Ac-RBRRRRRS*FLRBRBRBR-G |
| 38 | Ac-RRRRRRS*FLRBRBRBR-G |
| 39 | Ac-RBRRBRRRS*FLRRBRR-G |
| 40 | Ac-RBRRRRRS*FLRRRR-G |
| 41 | Ac-RRRRRRS*FLRRRR-G |
| 42 | Ac-RGRRS*GRRGRS*FLRGGRBRGGR-G |
| 43 | Ac-RXRRBRRXRS*FRXRBRXR-G |
| 44 | Ac-RXRRBRRXRS*RXRBRXR-G |
| 45 | Ac-RXRRBRRS*FQILYRBRXR-G |
| 46 | Ac-RXRRBRRS*FLRBRXR-G |
| 47 | Ac-RXRRBRRXRS*FLRXRBRXRS*FL-G |
| 48 | Ac-RXRRBRRXRRXRBRXRS*FL-G |
| 49 | Ac-RXRRS*RRXRS*FLRXRS*RXR-G |
| 50 | Ac-RXRRBRRXRS*FQRXRBRXR-G |
| 52 | Ac-RXRRBRRXRS*WFRXRBRXR-G |
| 53 | Ac-RXRRBRRXRS*QFRXRBRXR-G |
| 54 | Ac-RXRRBRRXRS*FQRXRBS*YQFLIRXR-G |
| 55 | Ac-RXRRBRRS*RBRXR-G |
| 56 | Ac-RXRRFS*RRBRBRXR-G |
| 57 | Ac-R FS*RRBRRBRBRXR-G |
| 58 | Ac-RXRRS*RRBRBRXR-G |
| 59 | Ac-RS*RRBRRBRBRXR-G |
| 60 | Ac-RXRRBRRBRS*RXR-G |
| 61 | Ac-RXRRBRRBRBRS*R-G |
| 62 | Ac-RXRRBRFS*RBR-G |

TABLE 2-continued

| Peptide number incorporating corresponding SEQ ID. NO. | Sequence |
|---|---|
| 63 | Ac-RXRRBRS*RBR-G |
| 64 | Ac-RXRBRRS*RBR-G |
| 65 | Ac-RRBRRS*RBR-G |
| 66 | Ac-HXHRBRRXRS*RXHBHXR-G |
| 67 | Ac-RXRRBRRS*S*RBRXR-G |
| 68 | Ac-RXRRBRRS*S*S* RBRXR-G |
| 69 | Ac-RXRRS*RRS*RS*RXR-G |
| 70 | Ac-RBRBRS*RBRBR-G |
| 71 | Ac-RXRXRS*RXRXR-G |
| 72 | Ac-RXRRBS*BRBRBR-G |
| 73 | Ac-RXRRBRRZS*RBRXR-B (Z = Tic = 1,2,3,4-tetrahydroisoquinoline-3-carboxylic acid) |
| 74 | Ac-RXRRBRRFS$^1$*RBRXR-B, S$^1$* = D-Ser[D-Glc] |
| 75 | Ac-RXRRBRRFS$^2$*RBRXR-B, S$^2$* = L-Ser[L-Glc] |
| 76 | Ac-RXRRBRRFS$^3$*RBRXR-B, S$^3$* = (L-Ser[D-Man] |
| 77 | Ac-RXRRBRRFS$^4$*RBRXR-B, S$^4$* = L-Ser[D-Lac] |
| 78 | Ac-RXRRBRRFN*RBRXR-B, N* = L-Asn[D-GlcNac] |
| 79 | Ac-RXRRBRRFS$^6$*RBRXR-B, S$^6$* = L-Ser[Gal]* |
| 80 | Ac-RAzRRAzRRZS*RAzRAzR-B (Z = Tic = 1,2,3,4-tetrahydroisoquinoline-3-carboxylic acid, Az = 3-azetidine-carboxylic acid) |

TABLE 3

| | Peptide No. | | | | | | | | |
|---|---|---|---|---|---|---|---|---|---|
| | 1 | 2 | 3 | 4 | 5 | 6 | 7 | 17 | 14 |
| Central Nervous System | | | | | | | | | |
| Cortex | 1.29** | 1.16* | 0.93 | 1.1 | 1.11 | 1.13 | 1.01 | 1.27* | 1.50* |
| Brainstem | 1.48*** | 1.36*** | 0.86 | 0.98 | 1.22 | 1.38** | 1.11 | 1.2 | 1.97*** |
| Cerebellum | 1.25* | 1.15* | 1.025 | 0.96 | 1 | 1.05 | 0.97 | 1.19* | 1.26 |
| Cervical | 1.50*** | 1.78** | 0.92 | 1.14* | 1.24* | 0.88** | 1.26 | 1.41* | 1.23** |
| Thoracic | 1.45*** | 1.49* | 1 | 1.12 | 1.23 | 1.37* | 1.33 | 1.39** | 2.38** |
| Lumbar | 1.28*** | 1.48** | 1.1 | 1 | 1.25* | 1.23* | 0.97 | 1.1 | 2.23 |

TABLE 3-continued

| | Peptide No. | | | | | | | | |
|---|---|---|---|---|---|---|---|---|---|
| | 1 | 2 | 3 | 4 | 5 | 6 | 7 | 17 | 14 |
| Skeletal Muscle | | | | | | | | | |
| TA | 3.30*** | 3.45**** | 3.95*** | 4.23**** | 2.80**** | | 3.34**** | 3.00*** | 3.24**** |
| Quad | 3.37*** | 2.52**** | 3.35**** | 2.70**** | 2.46**** | 2.89*** | 2.80**** | 2.68*** | 2.45*** |
| Gastroc | 3.03*** | 2.98**** | 3.4 | 3.64**** | 2.49**** | 3.22**** | 2.92**** | 3.25**** | 2.82**** |
| Off Target | | | | | | | | | |
| Liver | 2.81 | 2.91 | 4.57 | 3.26 | 2.73 | 2.78 | 3.19 | 3.78 | 3.45 |

The invention claimed is:

1. A peptide comprising a sequence selected from the following sequences:

```
                              (SEQ ID NO. 8)
RXRRBRRXRQFLRXRBRXRS*,

                              (SEQ ID NO. 11)
S*RXRRBRRXRQFLRXRBRXR,

                              (SEQ ID NO. 14)
RXRRBRRXRS*FLRXRBRXR,

                              (SEQ ID NO. 47)
RXRRBRRXRS*FLRXRBRXRS*FL,

                              (SEQ ID NO. 50)
RXRRBRRXRS*FQRXRBRXR,

                              (SEQ ID NO. 52)
RXRRBRRXRS*WFRXRBRXR,
and

                              (SEQ ID NO. 53)
RXRRBRRXRS*QFRXRBRXR,
```

wherein X is aminohexanoic acid, B is beta-alanine, and wherein S* represents L-serine glycosylated with D-Glucose sugar.

2. A conjugate comprising the peptide according to claim 1 covalently linked to a therapeutic molecule.

3. The conjugate of claim 2, wherein the therapeutic molecule is selected from: a nucleic acid, peptide nucleic acid, antisense oligonucleotide, short interfering RNA, micro RNA, peptide, cyclic peptide, protein, pharmaceutical and drug.

4. A peptide selected from the following sequences: RXRRBRRXRS*FLRXRBRXR (SEQ ID NO.14), RXRRBRRFS*RBRXR (SEQ ID NO.17), RXRRBRRZS*RBRXR (SEQ ID NO.73), RXRRBRRFS11*RBRXR (SEQ ID NO.74), RBRBRS*RBRBR (SEQ ID NO.70) and RXRXRS*RXRXR (SEQ ID NO.71), wherein X is aminohexanoic acid, B is beta-alanine, Z is 1,2,3,4-tetrahydroisoquinoline-3-carboxylic acid, S* represents L-serine glycosylated with D-Glucose sugar, and $S^1$* represents D-serine glycosylated with D-Glucose sugar.

5. A conjugate comprising the peptide according to claim 4 covalently linked to a therapeutic molecule.

6. The conjugate of claim 5, wherein the therapeutic molecule is selected from: a nucleic acid, peptide nucleic acid, antisense oligonucleotide, short interfering RNA, micro RNA, peptide, cyclic peptide, protein, pharmaceutical and drug.

7. A peptide comprising a sequence selected from the following sequences:

```
                              (SEQ ID NO. 12)
RXRRBRRXRS*QFLS*RXRBRXR,

                              (SEQ ID NO. 13)
RXRRBRRXRS*QFLRXRBRXR,

                              (SEQ ID NO. 43)
RXRRBRRXRS*FRXRBRXR,
and

                              (SEQ ID NO. 44)
RXRRBRRXRS*RXRBRXR,
```

wherein X is aminohexanoic acid, B is beta-alanine and S* represents L-serine glycosylated with D-Glucose sugar.

8. A conjugate comprising the peptide according to claim 7 covalently linked to a therapeutic molecule.

9. The conjugate of claim 8, wherein the therapeutic molecule is selected from: a nucleic acid, peptide nucleic acid, antisense oligonucleotide, short interfering RNA, micro RNA, peptide, cyclic peptide, protein, pharmaceutical and drug.

10. A peptide comprising a sequence selected from the following sequences:

(SEQ ID NO. 51)
RXRRBRRFS$^1$*RXRBR, (SEQ ID NO. 111)
RXRRBRRFS$^2$*RXRBR, (SEQ ID NO. 112)
RXRRBRRFS$^3$*RXRBR, (SEQ ID NO. 116)
RXRRBRRZS*RXRBR, (SEQ ID NO. 157)
RXRRBRRFS$^4$*RXRBR, (SEQ ID NO. 158)
RXRRBRRFS$^6$*RXRBR, (SEQ ID NO. 160)
RXRRBRRFS$^5$*RXRBR, (SEQ ID NO. 168)
RXRRBRRS$^1$*RXRBR, (SEQ ID NO. 169)
RXRRBRRS$^2$*RXRBR, (SEQ ID NO. 170)
RXRRBRRS$^3$*RXRBR, (SEQ ID NO. 171)
RXRRBRRS$^4$*RXRBR, (SEQ ID NO. 172)
RXRRBRRN*RXRBR, (SEQ ID NO. 173)
RXRRBRRS$^6$*RXRBR,
and (SEQ ID NO. 175)
RXRRBRRS$^5$*RXRBR, wherein X is aminohexanoic acid, B is beta-alanine, Z is 1,2,3,4-tetrahydroisoquinoline-3-carboxylic acid, S* represents L-serine glycosylated with D-Glucose sugar, $S^1$* represents D-serine glycosylated with D-Glucose sugar, $S^2$* represents L-serine glycosylated with an L-Glucose sugar, $S^3$* represents L-serine glycosylated with a D-Mannose sugar, $S^4$* represents L-serine glycosylated with a D-Lactose sugar, N* represents L-asparagine glycosylated with a D-2-Acetylamino Glucose sugar, $S^5$* represents L-serine glycosylated with a D-2-Acetylamino Glucose sugar, and $S^6$* represents L-serine glycosylated with a Galactose sugar.

11. A conjugate comprising the peptide according to claim 10 covalently linked to a therapeutic molecule.

12. The conjugate of claim 11, wherein the therapeutic molecule is selected from: a nucleic acid, peptide nucleic acid, antisense oligonucleotide, short interfering RNA, micro RNA, peptide, cyclic peptide, protein, pharmaceutical and drug.

13. A peptide comprising a sequence selected from the following sequences:

RXRRBRRFS*RBRXR, (SEQ ID NO. 17)

RXRRBRRS*FQILYRBRXR, (SEQ ID NO. 45)

RXRRBRRS*FLRBRXR, (SEQ ID NO. 46)

RXRRBRRS*RBRXR, (SEQ ID NO. 55)

RXRRBRRS*S*RBRXR, (SEQ ID NO. 67)

RXRRBRRS*S*S*RBRXR, (SEQ ID NO. 68)

RXRRBRRZS*RBRXR, (SEQ ID NO. 73)

RXRRBRRFS$^1$*RBRXR, (SEQ ID NO. 74)

RXRRBRRFS$^2$*RBRXR, (SEQ ID NO. 75)

RXRRBRRFS$^3$*RBRXR, (SEQ ID NO. 76)

RXRRBRRFS$^4$*RBRXR, (SEQ ID NO. 77)

RXRRBRRFN*RBRXR, (SEQ ID NO. 78)

RXRRBRRFS$^6$*RBRXR, (SEQ ID NO. 79)

RXRRBRRFS$^5$*RBRXR, (SEQ ID NO. 159)
and

RXRRBRRS$^1$*RBRXR, (SEQ ID NO. 162)

wherein X is aminohexanoic acid, B is beta-alanine, Z is 1,2,3,4-tetrahydroisoquinoline-3-carboxylic acid, S* represents L-serine glycosylated with D-Glucose sugar, S'* represents D-serine glycosylated with D-Glucose sugar, S$^2$* represents L-serine glycosylated with an L-Glucose sugar, S$^3$* represents L-serine glycosylated with a D-Mannose sugar, S$^4$* represents L-serine glycosylated with a D-Lactose sugar, N* represents L-asparagine glycosylated with a D-2-Acetylamino Glucose sugar, S$^5$* represents L-serine glycosylated with a D-2-Acetylamino Glucose sugar, and S$^6$* represents L-serine glycosylated with a Galactose sugar.

14. A conjugate comprising the peptide according to claim 13 covalently linked to a therapeutic molecule.

15. The conjugate of claim 14, wherein the therapeutic molecule is selected from: a nucleic acid, peptide nucleic acid, antisense oligonucleotide, short interfering RNA, micro RNA, peptide, cyclic peptide, protein, pharmaceutical and drug.

16. A peptide comprising a sequence selected from the following sequences:

RBRRBRRBRS*FLRBRBRBR, (SEQ ID NO. 18)

RBRRBRRBRS*FLRBRBR, (SEQ ID NO. 29)

RBRRBRRBRS*FLRBR, (SEQ ID NO. 30)

RBRRBRRBRS*FLR, (SEQ ID NO. 31)

RBRRBRRBRS*FL, (SEQ ID NO. 32)

RBRRBRRBRS*FLRBRBRR, (SEQ ID NO. 33)

RBRRBRRBRS*FLRBRRR, (SEQ ID NO. 34)
and

RBRRBRRBRS*FLRRRR, (SEQ ID NO. 35)

wherein B is beta-alanine and S* represents L-serine glycosylated with D-Glucose sugar.

17. A conjugate comprising the peptide according to claim 16 covalently linked to a therapeutic molecule.

18. The conjugate of claim 17, wherein the therapeutic molecule is selected from: a nucleic acid, peptide nucleic acid, antisense oligonucleotide, short interfering RNA, micro RNA, peptide, cyclic peptide, protein, pharmaceutical and drug.

19. A peptide comprising a sequence selected from the following sequences:

RRBRRBRS*FLRBRBRBR, (SEQ ID NO. 24)

RBRRBRS*FLRBRBRBR, (SEQ ID NO. 25)

RRBRS*FLRBRBRBR, (SEQ ID NO. 26)

RBRS*FLRBRBRBR, (SEQ ID NO. 27)

RS*FLRBRBRBR, (SEQ ID NO. 28)

RBRRBRRRS*FLRBRBRBR, (SEQ ID NO. 36)

RBRRRRRS*FLRBRBRBR, (SEQ ID NO. 37)
and

RRRRRRS*FLRBRBRBR, (SEQ ID NO. 38)

wherein B is beta-alanine and S* represents L-serine glycosylated with D-Glucose sugar.

20. A conjugate comprising the peptide according to claim 19 covalently linked to a therapeutic molecule.

21. The conjugate of claim 20, wherein the therapeutic molecule is selected from: a nucleic acid, peptide nucleic acid, antisense oligonucleotide, short interfering RNA, micro RNA, peptide, cyclic peptide, protein, pharmaceutical and drug.

* * * * *